US009200322B2

(12) United States Patent
Barr et al.

(10) Patent No.: US 9,200,322 B2
(45) Date of Patent: Dec. 1, 2015

(54) BIOMARKERS FOR ACUTE ISCHEMIC STROKE

(75) Inventors: Taura L. Barr, Waynesburg, PA (US); Maria Del Mar Matarin, Kent (GB); Steven Jay Warach, West Lake Hills, TX (US); Andrew Barry Singleton, Poolesville, MD (US); Yvette P. Conley, North Huntingdon, PA (US)

(73) Assignees: The United States of America, as Represented by the Secretary, Department of Health and Human Services, Washington, DC (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/580,571

(22) PCT Filed: Feb. 22, 2011

(86) PCT No.: PCT/US2011/025748
§ 371 (c)(1),
(2), (4) Date: Mar. 11, 2013

(87) PCT Pub. No.: WO2011/106322
PCT Pub. Date: Sep. 1, 2011

(65) Prior Publication Data
US 2013/0189243 A1    Jul. 25, 2013

Related U.S. Application Data

(60) Provisional application No. 61/307,233, filed on Feb. 23, 2010.

(51) Int. Cl.
| | | |
|---|---|---|
| A61K 38/49 | (2006.01) | |
| G01N 33/68 | (2006.01) | |
| C12Q 1/68 | (2006.01) | |
| A61B 5/00 | (2006.01) | |
| A61B 5/055 | (2006.01) | |
| A61B 6/00 | (2006.01) | |

(52) U.S. Cl.
CPC ............ *C12Q 1/6876* (2013.01); *A61B 5/0042* (2013.01); *A61B 5/055* (2013.01); *A61B 6/501* (2013.01); *C12Q 1/6883* (2013.01); *G01N 33/6893* (2013.01); *C12Q 2600/112* (2013.01)

(58) Field of Classification Search
None
See application file for complete search history.

(56) References Cited

U.S. PATENT DOCUMENTS

2008/0057590 A1\*  3/2008  Urdea et al. ............... 436/71
2008/0220013 A1\*  9/2008  Hochstrasser et al. ..... 424/198.1

FOREIGN PATENT DOCUMENTS

WO    2005116268 A2    12/2005

OTHER PUBLICATIONS

Padma, V., Fisher, M., and Moonis, M. "Thrombolytic therapy for acute ischemic stroke: 3 h and beyond", Expert Review of Neurotherapeutics 2005, vol. 5, pp. 223-233.\*
Affymetrix, Inc., "An Analysis of Blood Processing Methods to Prepare Sample for GeneChip® Expression Profiling", Part No. 701488 Rev. 2; Santa Clara, CA 2003; pp. 1-15.\*
J. Ilzecka et al., "Acute phase proteins: alpha-1-acid glycoprotein (AGP) an alpha-1 antichymotrypsin (ACT) in serum of pati9ents with cerebral ischemic stroke", Neur. Neurochir. Pol., 32(3), pp. 495-502 (1998).
A. Flex et al., "Proinflammatory Genetic Profiles in Subjects with History of Ischemic Stroke", Stroke, vol. 35, pp. 2270-2275 (2004).
W. Whiteley et al., "Blood Biomarkers in the Diagnosis of Ischemic Stroke: A Systematic Review", Stoke, vol. 39, pp. 2902-2909 (2008).
Y. Tang et al., "Gene expression in blood changes rapidly in neutrophils and monocytes after ischemic stroke in humans: a microarray study", Journal of Cerebral Blood Flow & Metabolism, vol. 26, pp. 1089-1102 (2006).
D.F. Moore et al., "Using peripheral blood mononuclear cells to determine a gene expression profile of acute ischemic stroke: A pilot investigation", Stroke, vol. 111, pp. 212-221 (2005).
T. Thom et al. "Heart disease and stroke statistics—2006 update: A report from the american heart association statistics committee and stroke statistics subcommittee", Circulation. 2006;113:e85-151.
Hemmen TM, Meyer BC, McClean TL, Lyden PD. Identification of nonischemic 15 stroke mimics among 411 code strokes at the University of California, San Diego, stroke center. J Stroke Cerebrovasc Dis. 2008;17:23-25.
Tajouri L, Fernandez F, Griffiths LR. Gene expression studies in multiple sclerosis. Curr Genomics. 2007;8:181-189.
Scherzer CR, Eklund AC, Morse LJ, Liao Z, Locascio JJ, Fefer D, Schwarzschild 20 MA, Schlossmacher MG, Hauser MA, Vance JM, Sudarsky LR, Standaert DG, Growdon JH, Jensen RV, Gullans SR. Molecular markers of early parkinson's disease based on gene expression in blood. Proc Natl Acad Sci U S A. 2007;104:955-960.
Maes OC, Xu S, Yu B, Chertkow HM, Wang E, Schipper HM. Transcriptional profiling of alzheimer blood mononuclear cells by microarray. Neurobiol Aging. 25 2007;28:1795-1809.
Bittner M, Meltzer P, Chen Y, Jiang Y, Seftor E, Hendrix M, Radmacher M, Simon R, Yakhini Z, Ben-Dor A, Sampas N, Dougherty E, Wang E, Marincola F, Gooden C, Lueders J, Glatfelter A, Pollock P, Carpten J, Gillanders E, Leja D, Dietrich K, Beaudry C, Berens M, Alberts D, Sondak V. Molecular classification of cutaneous malignant melanoma by gene expression profiling. Nature. 2000;406:536-40.
Jones MH, Virtanen C, Honjoh D, Miyoshi T, Satoh Y, Okumura S, Nakagawa K, Nomura H, Ishikawa Y. Two prognostically significant subtypes of high-grade lung neuroendocrine tumours independent of small-cell and large-cell neuroendocrine carcinomas identified by gene expression profiles. Lancet. 2004;363:775-781.

(Continued)

*Primary Examiner* — Allison Fox
*Assistant Examiner* — Michelle F Paguio Frising
(74) *Attorney, Agent, or Firm* — Locke Lord LLP; Bryan D. Zerhusen

(57) ABSTRACT

The present invention provides methods and compositions for the diagnosis of acute ischemic stroke. The invention further provides methods and compositions for distinguishing acute ischemic stroke from other forms of stroke and TIAs and "stroke mimic" events. Moreover, methods and compositions are provided to facilitate the treatment of acute ischemic stroke patients.

27 Claims, 30 Drawing Sheets

(56) References Cited

OTHER PUBLICATIONS

Chang JC, Wooten EC, Tsimelzon A, Hilsenbeck SG, Gutierrez MC, Elledge R, Mohsin S, Osborne CK, Chamness GC, Allred DC, O'Connell P. Gene expression profiling for the prediction of therapeutic response to docetaxel in patients with breast cancer. Lancet. 2003;362:362-369.

Grond-Ginsbach C, Hummel M, Wiest T, Horstmann S, Pfleger K, Hergenhahn M, Hollstein M, Mansmann U, Grau AJ, Wagner S. Gene expression in human peripheral blood mononuclear cells upon acute ischemic stroke. J Neurol. 2008;255:723-731.

Moore DF, Li H, Jeffries N, Wright V, Cooper RA, Jr., Elkahloun A, Gelderman MP, Zudaire E, Blevins G, Yu H, Goldin E, Baird AE. Using peripheral blood mononuclear to cells to determine a gene expression profile of acute ischemic stroke: A pilot investigation. Circulation. 2005;111:212-221.

Tang Y, Xu H, Du X, Lit L, Walker W, Lu A, Ran R, Gregg JP, Reilly M, Pancioli A, Khoury JC, Sauerbeck LR, Carrozzella JA, Spilker J, Clark J, Wagner KR, Jauch EC, Chang DJ, Verro P, Broderick JP, Sharp FR. Gene expression in blood changes rapidly in neutrophils and monocytes after ischemic stroke in humans: A microarray study. J Cereb Blood Flow Metab. 2006;26:1089-1102.

Sharp FR, Xu H, Lit L, Walker W, Pinter J, Apperson M, Verro P. Genomic profiles of stroke in blood. Stroke. 2007;38:691-693.

Kidwell CS, Warach S. Acute ischemic cerebrovascular syndrome: Diagnostic criteria. Stroke. 2003;34:2995-2998.

D., NC. Expression profiling of whole blood specimens on illumina beadchips. Expression analysis tech note; www.Expressionanalysis.Com. Oct. 2007.

Barr TL, Latour LL, Lee KY, Schaewe TJ, Luby M, Chang GS, El-Zammar Z, Alam S, Hallenbeck JM, Kidwell CS, Warach S. Blood-brain barrier disruption in humans is independently associated with increased matrix metalloproteinase-9. Stroke. 2009.

Fernandez EJ, Lolis E. Structure, function, and inhibition of chemokines. Annu Rev Pharmacol Toxicol. 2002;42:469-499.

Brea D, Sobrino T, Blanco M, Cristobo I, Rodriguez-Gonzalez R, Rodriguez•Yanez M, Moldes 0, Agulla J, Leira R, Castillo J. Temporal profile and clinical significance of serum neuronspecific enolase and s100 in ischemic and hemorrhagic stroke. Clin Chem Lab Med. 2009;47:1513-1518.

Takami S, Minami M, Nagata I, Namura S, Satoh M. Chemokine receptor antagonist peptide, viral mip-ii, protects the brain against focal cerebral ischemia in mice. J Cereb Blood Flow Metab. 2001;21:1430-1435.

Stamatovic SM, Shakui P, Keep RF, Moore BB, Kunkel SL, Van Rooijen N, 15 Andjelkovic AV. Monocyte chemoattractant protein-1 regulation of blood-brain barrier permeability. J Cereb Blood Flow Metab. 2005;25:593-606.

Ceradini DJ, Kulkarni AR, Callaghan MJ, Tepper OM, Bastidas N, Kleinman ME, Capla JM, Galiano RD, Levine JP, Gurtner GC. Progenitor cell trafficking is regulated by hypoxic gradients through hif-1 induction of sdf-1. Nat Med. 2004;10:858-864.

Yamaguchi J, Kusano KF, Masuo 0, Kawamoto A, Silver M, Murasawa S,Bosch-Marce M, Masuda H, Losordo DW, Isner JM, Asahara T. Stromal cell-derived factor-1 effects on ex vivo expanded endothelial progenitor cell recruitment for ischemic neovascularization. Circulation. 2003;107:1322-1328.

Offner H, Subramanian S, Parker SM, Afentoulis ME, Vandenbark AA, Hurn PD. Experimental stroke induces massive, rapid activation of the peripheral immune system. J Cereb Blood Flow Metab. 2006;26:654-665.

Yan J, Greer JM, Etherington K, Cadigan GP, Cavanagh H, Henderson RD, O'Sullivan JD, Pandian JD, Read SJ, McCombe PA. Immune activation in the peripheral blood of patients with acute ischemic stroke. J Neuroimmunol. 2009;206:112-117.

Vorisek I, Hajek M, Tintera J, Nicolay K, Sykova E. Water adc, extracellular space volume, and tortuosity in the rat cortex after traumatic injury. Magn Reson Med. 2002;48:994-1003.

Carmichael ST, Archibeque I, Luke L, Nolan T, Momiy J, Li S. Growth?associated gene expression after stroke: Evidence for a growth-promoting region in per•infarct cortex. Exp Neurol. 2005;193:291-311.

Toeda K, Nakamura K, Hirohata S, Hatipoglu OF, Demircan K, Yamawaki H, Ogawa H, Kusachi S, Shiratori Y, Ninomiya Y. Versican is induced in infiltrating monocytes in myocardial infarction. Mol Cell Biochem. 2005;280:47-56.

Brown MD, Sacks DB. Iqgapl in cellular signaling: Bridging the gap. Trends Cell Biol. 2006;16:242-249.

Fukata M, Nakagawa M, Kaibuchi K. Roles of rho-family gtpases in cell polarisation and directional migration. Curr Opin Cell Biol. 2003;15:590-597.

Miao L, Calvert JW, Tang J, Parent AD, Zhang JH. Age-related rhoa expression in blood vessels of rats. Mech Ageing Dev. 2001;122:1757-1770.

Carbajal JM, Schaeffer RC, Jr. Rhoa inactivation enhances endothelial barrier function. Am J Physiol. 1999;277:C955-964.

Hordijk PL, Anthony E, Mul FP, Rientsma R, Oomen LC, Roos D. Vascular•endothelialcadherin modulates endothelial monolayer permeability. J Cell Sci. 1999;112 ( Pt 12):1915-1923.

Hochepied T, Berger FG, Baumann H, Libert C. Alpha(1)-acid glycoprotein: An 30 acute phase protein with inflammatory and immunomodulating properties. Cytokine Growth Factor Rev. 2003;14:25-34.

Fournier T, Medjoubi NN, Porquet D. Alpha-l-acid glycoprotein. Biochim Biophys Acta. 2000;1482:157-171.

Marsh BJ, Stevens SL, Hunter B, Stenzel-Poore MP. Inflammation and the emerging role of the toll-like receptor system in acute brain ischemia. Stroke. 2009;40:S34•37.

Medzhitov R. Toll-like receptors and innate immunity. Nat Rev Immunol. 5 2001;1:135-145.

Bianchi ME. Damps, pamps and alarmins: All we need to know about danger. J Leukoc Biol. 2007;81:1-5.

Salminen A, Huuskonen J, Ojala J, Kauppinen A, Kaarniranta K, Suuronen T. Activation of innate immunity system during aging: Nf-kb signaling is the molecular culprit of inflamm-aging. Ageing Res Rev. 2008;7:83-105.

Csiszar A, Wang M, Lakatta EG, Ungvari Z. Inflammation and endothelial dysfunction during aging: Role of nf-kappab. J Appl Physiol. 2008;105:1333-1341.

Letiembre M, Hao W, Liu Y, Walter S, Mihaljevic I, Rivest S, Hartmann T, Fassbender K. Innate immune receptor expression in normal brain aging. Neuroscience. 2007;146:248-254.

Fulop T, Larbi A, Douziech N, Fortin C, Guerard KP, Lesur 0, Khalil A, Dupuis G. Signal transduction and functional changes in neutrophils with aging. Aging Cell. 2004;3:217-226.

Kilic U, Kilic E, Matter CM, Bassctti CL, Hermann DM. Tlr-4 deficiency protects against focal cerebral ischemia and axotomy-induced neurodegeneration. Neurobiol Dis. 25 2008;31:33-40.

Ziegler G, Harhausen D, Schepers C, Hoffmann 0, Rohr C, Prinz V, Konig J, Lehrach H, Nietfeld W, Trendelenburg G. Tlr2 has a detrimental role in mouse transient focal cerebral ischemia. Biochem Biophys Res Commun. 2007;359:574-579.

Caso JR, Pradillo JM, Hurtado 0, Lorenzo P, Moro MA, Lizasoain I. Toll-like receptor 4 is involved in brain damage and inflammation after experimental stroke. Circulation. 2007;115:1599-1608.

Caso JR, Pradillo JM, Hurtado 0, Leza JC, Moro MA, Lizasoain I. Toll-like receptor 4 is involved in subacute stress-induced neuroinflammation and in the worsening of experimental stroke. Stroke. 2008;39:1314-1320.

Yang QW, Li JC, Lu FL, Wen AQ, Xiang J, Zhang LL, Huang ZY, Wang JZ. Upregulated expression of toll-like receptor 4 in monocytes correlates with severity of acute cerebral infarction. J Cereb Blood Flow Metab. 2008;28:1588-1596.

Urra X, Cervera A, Obach V, Climent N, Planas AM, Chamorro A. Monocytes are major players in the prognosis and risk of infection after acute stroke. Stroke. 2009;40:1262-1268.

Basso G, Case C, Dell'Orto M. Diagnosis and genetic subtypes of leukemia combining gene expression and flow cytometry. Blood Cells, Molecules, and Diseases. 5 2007;39:164-168.

(56) References Cited

OTHER PUBLICATIONS

Andersson A, Ritz C, Lindgren D, Eden P, Lassen C, Heldrup J, Olofsson T, Rade J, Fontes M, Porwit-MacDonald A, Behrendtz M, Hoglund M, Johansson B, Fioretos T, Microarray-based classification of a consecutive series of 121 childhood acute leukemias: Prediction of leukeminc and gentic subtype as well as of minimal residual disease status. Luekemia 2007;21:1198-1203.
Cardoso F, Van't-Verr L, Rutgers E, Loi S, Mook S, Piccart-Gebhart M. Clinical application of the 70-gene profile: The mindact trial. Journal of Clinical Oncology. 2008;26:729-735.
Sharp FR, Xu H, Lit L, Walker W, Apperson M, Gilbert DL, Glauser TA, Wong 15 B, Hershey A, Liu DZ, Pinter J, Zhan X, Liu X, Ran R. The future of genomic profiling of neurological diseases using blood. Arch Neurol. 2006;63:1529-1536.
Whiteley W, Tseng MC, Sandercock P. Blood biomarkers in the diagnosis of ischemic stroke, A Systematic review. Stroke. 2008.
Stone GP, Memaugh R, Haselton FR. Virus detection using filament-coupled antibodies. Biotechnol Bioeng. 2005;91:699-706.
Easton JD, Saver JL, Albers GW, Alberts MJ, Chaturvedi S, Feldman E, Hatsukami TS, Higashida RT, Johnston SC, Kidwell CS, Lutsep HL, Miller E, Sacco RL. Definition and evaluation of transient ischemic attack: A scientific statement for healthcare professionals from the american heart association/american stroke association stroke council; council on cardiovascular surgery and anesthesia; council on cardiovascular radiology and intervention; council on cardiovascular nursing; and the interdisciplinary council on peripheral vascular disease. The american academy of neurology affirms the value of this statement as an educational tool for neurologists. Stroke 2009, vol. 40, pp. 2276-2293.
Laskowitz DT, Kasner SE, Saver J, Remmel KS, Jauch EC, Clinical usefulness of a biomarkerbased diagnostic test for acute stroke: The biomarker rapid assessment in ischemic injury (brain) study, Stroke, 2009: 40:77-85.
Takami S, Minami M, Nagata I,, Namura S, Satoh M., Chemokine receptor antagonist peptide, viral mip-ii, protects the brain against focal cerebral ischemia in mice., J. Cereb Blood Flow Metab., 2001; 21:1430-1435.
Beggah AT, Dours-Zimmermann MT, Barras FM, Brosius A., Zimmermann DR, Zurn AD, Lesion-induced differential expression and cell association of neurocan, brevican, versican v1 and v2 in the mouse dorsal root entry zone, Neuroscience, 2005; 133:749-762.
Wojciak-Stothard B, Ridley AJ, Rho gtpases and the regulation of endothelial permeability, Vascal Pharmacol, 2002; 39:187-199.
Rubartelli A, Lotze MT, Inside, outside, upside down: Damage-associated molecular-pattern molecules (damps) and redox., Trends Immunol., 2007; 28:429-436.
Chalela JA, Kidwell CS, Nentwich LM, Luby M, Butman JA, Demchuk AM, Hill MD, Patronas N, Latour L, Warach S., Magnetic resonance imaging and computed tomography in emergency assessment of patients with suspected acute stroke: A prospective comparison, Lancet. 2007; 369:293-298.
Rosamond W, Flegal K, Furie K, Go A, Greenlund K, Haase N, Hailpern SM, Ho M Howard V, Kissela B, Kittner S, Lloyd-Jones D, McDermott M, Meigs J, Moy C, Nichol G, O'Donnell C, Roger V, Sorlie P, Steinberger J, Thom T, Wilson M, Hong Y., Heart disease and stroke statistics—2008 update: A report from the american heart association statistics committee and stroke statistics subcommittee, Circulation, 2008; 117:e25-146.
Reeves MJ, Arora S, Broderick JP, Frankel M, Heinrich JP, Hickenbottom S, Karp H, LaBresh KA, Malarcher A, Mensah G, Moomaw CJ, Schwamm L, Weiss P., Acute stroke care in the US: Results from 4 pilot prototypes of the Paul Coverdell National Acute Stroke Registry, Stroke, 2005; 36:1232-1240.
Tang Y, Xu H, Du X, Lit L, Walker W, Lu A, Ran R, Gregg JP, Reilly M, Pancioli A, Khoury JC, Sauerbeck LR, Sarrozella JA, Spilker J, Clark J, Wagner KR, Jauch EC, Chang DJ, Verro P, Broderick JP, Sharp FR., Gene expression in blood changes rapidly in neutrophils and monocytes after ischemic stroke in humans: A microarray study., J. Cereb Blood Flow Metab., 2006; 26:1089-1102.
Montaner J, Perea-Gainza M, Delgado P, Ribo M, Chacon P, Rosell A, Quintana M, Palacios ME, Molina CA, Alvarez-Sabin J., Etiologic diagnosis of ischemic stroke subtypes with plasma biomarkers., Stroke, 2008; 39:2280-2287.
Kidwell CS, Warach S., Acute ischemic cerebrovascular syndrome: Diagnostic criteria., Stroke, 2003; 34:2995-2998.
Meschia JF, Lojacono MA, Miller MJ, Brott TG, Atkinson EJ, O'Brien PC., Reliability of the questionnaire for verifying stroke-free status., Verebrovasc Dis., 2004; 17:218-223.
Griffiths RA, Good WR, Watson NP, O'Donnell HF, Fell PJ, Shakespear JM., Normal erythrocyte sedimentation rate in the elderly., Br. Med. J. (Clin Res. Ed)., 1984; 289:724-725.
Bonita R, Beaglehole R., Recovery of motor function after stroke., Stroke, 1988; 19:1497-1500.
Wilson JT, Pettigrew LE, Teasdale GM., Structured interviews for the glasgow outcome scale and the extended glasgow outcome scale: Guidelines for their use., J. Neurotrauma, 1998; 15:573-585.
Spertus JA, Winder JA, Dewhurst TA, Deyo RA, Prodzinski J, McDonnell M, Fihn SD., Development and evaluation of the seattle angina questionnaire: A new functional status measure for coronary artery disease., J. Am Coll. Cardiol., 1995; 25:333-341.
Bushel PR, Wolfinger RD, Gibson G., Simultaneous clustering of gene expression data with clinical chemistry and pathological evaluations reveals phenotypic prototypes., BMC Syst Biol., 2007; 1:15.
Perez JM, Hasleton FR, Wright DW., Viral detection using DNA functionalized gold filaments., The Analyst, 2009; 134:1548-1553.
Tsourkas A, Behlke MA, Rose SD, Bao G., Hybridization kinetics and thermodynamics of molecular beacons., Nucleic Acids Res., 2003; 31:1319-1330.
Bonnet G, Tyagi S, Libchaber A, Kramer FR., Thermodynamic basis of the enhanced specificity of structured DNA probes., Proc Natl Acad Sci USA, 1999; 96:6171-6176.
Zheng PS, Wen J, ang LC, Sheng W, Viloria-Petit A, Wang Y, Wu Y, Kerbel RS, Yang BB. Versican/pg-m g3 domain promotes tumor growth and angiogenesis. FASEB J. 2004; 18:754-756.
Leonardo CC, Eakin AK, Ajmo JM, Gottschall PE. Versican and brevican are expressed with distinct pathology in neonatal hypoxic-ischemic injury. J. Neurosci Res. 2008; 86:1106-1114.
Miao L, Calvert JW, Tang J, Parent AD, Zhang JH. Age-related rhoa expression in blood vessels of rats. Mech. Ageing Dev. 2001; 122:1757-1770.
Fulop T, Larbi A, Douziech N, Fortin C, Guerard KP, Lesur O, Khalil A, Dupuis G. Dignal transduction and functional changes in neutrophils with aging. Aging Cell. 2004; 3:217-226.

\* cited by examiner

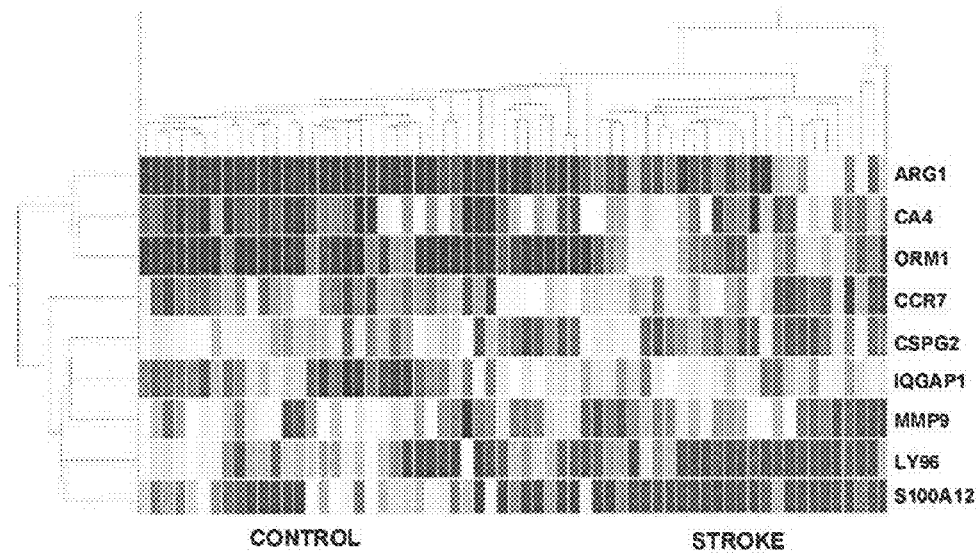

| Gene | p-value | Fold change | Regulation | Description |
|---|---|---|---|---|
| ARG1 | 2.84E-07 | 3.175 | Up | Arginase-1 |
| CA4 | 2.0E-04 | 2.122 | Up | Carbonic anhydrase-4 |
| CCR7 | 4.37E-05 | 2.094 | Down | Chemokine CC Motif Receptor 7 |
| CSPG2 | 3.45E-05 | 2.087 | Up | Chondroitin sulfate proteoglycan 2 |
| IQGAP1 | 7.97E-07 | 2.031 | Up | IQ motif-containing GTPase-activating protein 1 |
| LY96 | 0.001 | 2.159 | Up | Lymphocyte antigen 96; MD2 protein |
| MMP9 | 1.11E-05 | 2.644 | Up | Matrix metalloproteinase 9; gelatinase B |
| ORM1 | 0.006 | 2.246 | Up | Orosomucoid 1; alpha 1 acid glycoprotein |
| S100A12 | 3.87E-04 | 2.354 | Up | S100 calcium binding protein A12; calgranulin C |

Figure 1

Homo sapiens chemokine (C-C motif) receptor 7 (CCR7), mRNA
NCBI Reference Sequence: NM_001838.2 (SEQ ID NO: 1)

```
   1 agacaggggt agtgcgaggc cgggcacagc cttcctgtgt ggttttaccg cccagagagc
  61 gtcatggacc tggggaaacc aatgaaaagc gtgctggtgg tggctctcct tgtcatttc
 121 caggtatgcc tgtgtcaaga tgaggtcacg gacgattaca tcggagacaa caccacagtg
 181 gactacactt tgttcgagtc tttgtgctcc aagaaggacg tgcggaactt taaagcctgg
 241 ttcctcccta tcatgtactc catcatttgt ttcgtgggcc tactgggcaa tgggctggtc
 301 gtgttgacct atatctattt caagaggctc aagaccatga ccgatacccta cctgctcaac
 361 ctggcggtgg cagacatcct cttcctcctg acccttcct tctgggccta cagcgcggcc
 421 aagtcctggg tcttcggtgt ccactttgc aagctcatct ttgccatcta caagatgagc
 481 ttcttcagtg gcatgctcct acttctttgc atcagcattg accgctacgt ggccatcgtc
 541 caggctgtct cagctcaccg ccaccgtgcc cgcgtccttc tcatcagcaa gctgtcctgt
 601 gtgggcatct ggatactagc cacagtgctc tccatcccag agctcctgta cagtgacctc
 661 cagaggagca gcagtgagca gcgatgcga tgctctctca tcacagagca tgtggaggcc
 721 tttatcacca tccaggtggc ccagatggtg atcggctttc tggtcccct gctggccatg
 781 agcttctgtt accttgtcat catccgcacc ctgctccagg cacgcaactt tgagcgcaac
 841 aaggccatca aggtgatcat cgctgtggtc gtggtcttca tagtcttcca gctgccctac
 901 aatggggtgg tcctggccca gacggtggcc aacttcaaca tcaccagtag cacctgtgag
 961 ctcagtaagc aactcaacat cgcctacgac gtcacctaca gcctggcctg cgtccgctgc
1021 tgcgtcaacc ctttcttgta cgccttcatc ggcgtcaagt tccgcaacga tctcttcaag
1081 ctcttcaagg acctgggctg cctcagccag gagcagctcc ggcagtggtc ttcctgtcgg
1141 cacatccggc gctcctccat gagtgtggag gccgagacca ccaccacctt ctccccatag
1201 gcgactcttc tgcctggact agagggacct ctcccagggt ccctgggggtg gggataggga
1261 gcagatgcaa tgactcagga catccccccg ccaaaagctg ctcagggaaa agcagctctc
1321 ccctcagagt gcaagcccct gctccagaag atagcttcac cccaatccca gctacctcaa
1381 ccaatgccaa aaaagacag ggctgataag ctaacaccag acagacaaca ctgggaaaca
1441 gaggctattg tcccctaaac caaaaactga aagtgaaagt ccagaaactg ttcccacctg
1501 ctggagtgaa ggggccaagg agggtgagtg caaggggcgt gggagtggcc tgaagagtcc
1561 tctgaatgaa ccttctggcc tcccacagac tcaaatgctc agaccagctc ttccgaaaac
1621 caggcctat ctccaagacc agagatagtg gggagacttc ttggcttggt gaggaaaagc
1681 ggacatcagc tggtcaaaca aactctctga accctccct ccatcgtttt cttcactgtc
1741 ctccaagcca gcgggaatgg cagctgccac gccgccctaa aagcacactc atcccctcac
1801 ttgccgcgtc gccctcccag gctctcaaca ggggagagtg tggtgtttcc tgcaggccag
1861 gccagctgcc tccgcgtgat caaagccaca ctctgggctc cagagtgggg atgacatgca
1921 ctcagctctt ggctccactg ggatgggagg agaggacaag ggaaatgtca ggggcggga
1981 gggtgacagt ggccgcccaa ggcccacgag cttgttcttt gttctttgtc acagggactg
2041 aaaacctctc tcatgttct gctttcgatt cgttaagaga gcaacatttt acccacacac
2101 agataaagtt tcccttgag gaaacaacag ctttaaaaga aaagaaaaa aaaagtcttt
2161 ggtaaatggc aaaaaaaaaa aaaaaaaa
```

Figure 4A

Chemokine (C-C motif) receptor 7 precursor [Homo sapiens]
ACCESSION NP_001829 (SEQ ID NO: 2)

```
  1 MDLGKPMKSV LVVALLVIFQ VCLCQDEVTD DYIGDNTTVD YTLFESLCSK KDVRNFKAWF
 61 LPIMYSIICF VGLLGNGLVV LTYIYFKRLK TMTDTYLLNL AVADILFLLT LPFWAYSAAK
121 SWVFGVHFCK LIFAIYKMSF FSGMLLLLCI SIDRYVAIVQ AVSAHRHRAR VLLISKLSCV
181 GIWILATVLS IPELLYSDLQ RSSSEQAMRC SLITEHVEAF ITIQVAQMVI GFLVPLLAMS
241 FCYLVIIRTL LQAPNFERNK AIKVIIAVVV VFIVFQLPYN GVVLAQTVAN FNITSSTCEL
301 SKQLNIAYDV TYSLACVRCC VNPFLYAFIG VKFRNDLFKL FKDLGCLSQE QLRQWSSCRH
361 IRRSSMSVEA ETTTTFSP
```

Figure 4B

Homo sapiens versican (VCAN), mRNA; CSPG2
NCBI Reference Sequence: NM_004385.2 (SEQ ID NO: 3)

```
   1 gctgccccga gccttctgg ggaagaactc caggcgtgcg gacgcaacag ccgagaacat
  61 taggtgttgt ggacaggagc tgggaccaag atcttcggcc agccccgcat cctcccgcat
 121 cttccagcac cgtcccgcac cctccgcatc cttccccggg ccaccacgct tctatgtga
 181 cccgcctggg caacgccgaa cccagtcgcg cagcgctgca gtgaattttc cccccaaact
 241 gcaataagcc gccttccaag gccaagatgt tcataaatat aaagagcatc ttatggatgt
 301 gttcaacctt aatagtaacc catgcgctac ataaagtcaa agtgggaaaa agcccaccgg
 361 tgaggggctc cctctctgga aaagtcagcc tacctgtca ttttcaacg atgcctactt
 421 tgccacccag ttacaacacc agtgaatttc tccgcatcaa atggtctaag attgaagtgg
 481 acaaaaatgg aaaagatttg aaagagacta ctgtccttgt ggcccaaaat ggaaatatca
 541 agattggtca ggactacaaa gggagagtgt ctgtgcccac acatcccgag gctgtgggcg
 601 atgcctccct cactgtggtc aagctgctgg caagtgatgc gggtctttac cgctgtgacg
 661 tcatgtacgg gattgaagac acacaagaca cggtgtcact gactgtggat gggggttgtgt
 721 ttcactacag ggcggcaacc agcaggtaca cactgaattt tgaggctgct cagaaggctt
 781 gtttggacgt tggggcagtc atagcaactc cagagcagct cttgctgcc tatgaagatg
 841 gatttgagca gtgtgacgca ggctggctgg ctgatcagac tgtcagatat cccatccggg
 901 ctcccagagt aggctgttat ggagataaga tgggaaaggc aggagtcagg acttatggat
 961 tccgttctcc ccaggaaact tacgatgtgt attgttatgt ggatcatctg gatggtgatg
1021 tgttccacct cactgtcccc agtaaattca ccttcgagga ggctgcaaaa gagtgtgaaa
1081 accaggatgc caggctggca acagtggggg aactccaggc ggcatggagg aacggctttg
1141 accagtgcga ttacgggtgg ctgtcggatg ccagcgtgcg ccaccctgtg actgtggcca
1201 gggcccagtg tggaggtggt ctacttgggg tgagaaccct gtatcgtttt gagaaccaga
1261 caggcttccc tccccctgat agcagatttg atgcctactg cttttaaacct aaagaggcta
1321 caaccatcga tttgagtatc ctcgcagaaa ctgcatcacc cagtttatcc aaagaaccac
1381 aaatggtttc tgatagaact acaccaatca tcccttagt tgatgaatta cctgtcattc
1441 caacagagtt ccctcccgtg ggaaatattg tcagttttga acagaaagcc acagtccaac
1501 ctcaggctat cacagatagt ttagccacca aattaccac acctactggc agtaccaaga
1561 agccctggga tatggatgac tactcacctt ctgcttcagg acctcttgga agctagaca
1621 tatcagaaat taaggaagaa gtgctccaga gtacaactgg cgtctctcat tatgctacgg
1681 attcatggga tgtgtcgtg gaagataaac aaacacaaga atcggttaca cagattgaac
1741 aaatagaagt gggtccttg gtaacatcta tggaaatctt aaagcacatt ccttccaagg
1801 aattccctgt aactgaaaca ccattggtaa ctgcaagaat gatcctggaa tccaaaactg
1861 aaaagaaaat ggtaagcact gtttctgaat tggtaaccac aggtcactat ggattcacct
1921 tgggagaaga ggatgatgaa gacagaacac ttacagttgg atctgatgag agcacccttga
1981 tctttgacca aattcctgaa gtcattacgg tgtcaaagac ttcagaagac accatccaca
2041 ctcatttaga agacttggag tcagtctcag catccacaac tgtttcccct ttaattatgc
2101 ctgataataa tggatcatcc atggatgact gggaagagag acaaactagt ggtaggataa
2161 cggaagagtt tcttggcaaa tatctgtcta ctacaccttt tccatcacag catcgtacag
2221 aaatagaatt gtttccttat tctggtgata aaatattagt agagggaatt tccacagtta
2281 tttatccttc tctacaaaca gaaatgacac atagaagaga aagaacagaa acactaatac
2341 cagagatgag aacagatact tatacagatg aaatacaaga agatcact aaaagtccat
2401 ttatgggaaa aacagaagaa gaagtcttct ctgggatgaa actctctaca tctctctcag
```

Figure 5A

```
2461 agccaattca tgttacagag tcttctgtgg aaatgaccaa gtcttttgat ttcccaacat
2521 tgataacaaa gttaagtgca gagccaacag aagtaagaga tatggaggaa gactttacag
2581 caactccagg tactacaaaa tatgatgaaa atattacaac agtgcttttg gccatggta
2641 ctttaagtgt tgaagcagcc actgtatcaa aatggtcatg ggatgaagat aatacaacat
2701 ccaagccttt agagtctaca gaaccttcag cctcttcaaa attgccccct gccttactca
2761 caactgtggg gatgaatgga aaggataaag acatcccaag tttcactgaa gatggagcag
2821 atgaatttac tcttattcca gatagtactc aaaagcagtt agaggaggtt actgatgaag
2881 acatagcagc ccatggaaaa ttcacaatta gatttcagcc aactacatca actggtattg
2941 cagaaaagtc aactttgaga gattctacaa ctgaagaaaa agttccacct atcacaagca
3001 ctgaaggcca agtttatgca accatggaag gaagtgcttt gggtgaagta gaagatgtgg
3061 acctctctaa gccagtatct actgttcccc aatttgcaca cacttcagag gtggaaggat
3121 tagcatttgt tagttatagt agcacccaag agcctactac ttatgtagac tcttcccata
3181 ccattcctct ttctgtaatt cccaagacag actggggagt gttagtacct tctgttccat
3241 cagaagatga agttctaggt gaaccctctc aagacatact tgtcattgat cagactcgcc
3301 ttgaagcgac tatttctcca gaaactatga gaacaacaaa aatcacagag ggaacaactc
3361 aggaagaatt cccttggaaa gaacagactg cagagaaacc agttcctgct ctcagttcta
3421 cagcttggac tccaaggag gcagtaacac cactggatga acaagaggc gatggatcag
3481 catatacagt ctctgaagat gaattgttga caggttctga gagggtccca gtttagaaa
3541 caactccagt tggaaaaatt gatcacagtg tgtcttatcc accaggtgct gtaactgagc
3601 acaaagtgaa aacagatgaa gtggtaacac taacaccacg cattgggcca aaagtatctt
3661 taagtccagg gcctgaacaa aaatatgaaa cagaaggtag tagtacaaca ggatttacat
3721 catctttgag tccttttagt acccacatta cccagcttat ggaagaaacc actactgaga
3781 aaacatccct agaggatatt gatttaggct caggattatt tgaaaagccc aaagccacag
3841 aactcataga attttcaaca atcaaagtca cagttccaag tgatattacc actgccttca
3901 gttcagtaga cagacttcac acaacttcag cattcaagcc atcttccgcg atctacaaga
3961 aaccacctct catcgacagg gaacctggtg aagaaacaac cagtgacatg gtaatcattg
4021 gagaatcaac atctcatgtt cctcccacta cccttgaaga tattgtagcc aaggaaacag
4081 aaaccgatat tgatagagag tatttcacga cttcaagtcc tcctgctaca cagccaacaa
4141 gaccacccac tgtggaagac aaagaggcct ttggacctca ggcgcttttct acgccacagc
4201 cccagcaag cacaaaattt caccctgaca ttaatgttta tattattgag gtcagagaaa
4261 ataagacagg tcgaatgagt gattgagtg taattggtca tccaatagat tcagaatcta
4321 aagaagatga accttgtagt gaagaaacag atccagtgca tgatctaatg gctgaaattg
4381 tacctgaatt ccctgacata attgaaatag acctataccc cagtgaagaa aatgaagaag
4441 aagaagaaga gtgtgcaaat gctactgatg tgacaaccac cccatctgtg cagtacataa
4501 atgggaagca tctcgttacc actgtgccca aggacccaga agctgcagaa gctaggcgtg
4561 gccagtttga aagtgttgca ccttctcaga atttctcgga cagctctgaa agtgatactc
4621 atccatttgt aatagccaaa acggaattgt ctactgctgt gcaacctaat gaatctacag
4681 aaacaactga gtctcttgaa gttacatgga gcctgagac ttaccctgaa acatcagaac
4741 atttttcagg tggtgagcct gatgttttcc ccacagtcc attccatgag gaatttgaaa
4801 gtggaacagc caaaaaaggg gcagaatcag tcacagagag agatactgaa gttggtcatc
4861 aggcacatga acatactgaa cctgtatctc tgttcctga agagtcttca ggagagattg
4921 ccattgacca agaatctcag aaaatagcct ttgcaagggc tacagaagta acatttggtg
4981 aagaggtaga aaaaagtact tctgtcacat acactcccac tatagttcca agttctgcat
5041 cagcatatgt ttcagaggaa gaagcagtta ccctaatagg aaatccttgg ccagatgacc
```

Figure 5A (con't)

5101 tgttgtctac caaagaaagc tgggtagaag caactcctag acaagttgta gagctctcag
5161 ggagttcttc gattccaatt acagaaggct ctggagaagc agaagaagat gaagatacaa
5221 tgttcaccat ggtaactgat ttatcacaga gaaatactac tgatacactc attactttag
5281 acactagcag gataatcaca gaaagcttt ttgaggttcc tgcaaccacc atttatccag
5341 tttctgaaca accttctgca aaagtggtgc ctaccaagtt tgtaagtgaa acagacactt
5401 ctgagtggat tccagtacc actgttgagg aaaagaaaag gaaggaggag gagggaacta
5461 caggtacggc ttctacattt gaggtatatt catctacaca gagatcggat caattaattt
5521 tacccttga attagaaagt ccaaatgtag ctacatctag tgattcaggt accaggaaaa
5581 gtttatgtc cttgacaaca ccaacacagt ctgaaaggga aatgacagat tctactcctg
5641 tctttacaga aacaaataca ttagaaaatt tgggggcaca gaccactgag cacagcagta
5701 tccatcaacc tggggttcag gaagggctga ccactctccc acgtagtcct gcctctgtct
5761 ttatggagca gggctctgga gaagctgctg ccgaccaga aaccaccact gtttcttcat
5821 tttcattaaa cgtagagtat gcaattcaag ccgaaaagga agtagctggc actttgtctc
5881 cgcatgtgga aactacattc tccactgagc caacaggact ggttttgagt acagtaatgg
5941 acagagtagt tgctgaaaat ataacccaaa catccaggga aatagtgatt tcagagcgat
6001 taggagaacc aaattatggg gcagaaataa ggggctttc cacaggttt cctttggagg
6061 aagatttcag tggtgacttt agagaatact caacagtgtc tcatcccata gcaaaagaag
6121 aaacggtaat gatggaaggc tctggagatg cagcatttag ggacacccag acttcaccat
6181 ctacagtacc tacttcagtt cacatcagtc acatatctga ctcagaagga cccagtagca
6241 ccatggtcag cacttcagcc ttccctgggg aagagtttac atcctcagct gagggctcag
6301 gtgagcaact ggtcacagtc agcagctctg ttgttccagt gcttccagt gctgtgcaaa
6361 agtttctgg tacagcttcc tccattatcg acgaaggatt gggagaagtg ggtactgtca
6421 atgaaattga tagaagatcc accatttac caacagcaga gtggaaggt acgaaagctc
6481 cagtagagaa ggaggaagta aaggtcagtg gcacagtttc aacaaacttt cccaaaacta
6541 tagagccagc caaattatgg tctaggcaag aagtcaaccc tgtaagacaa gaaattgaaa
6601 gtgaaacaac atcagaggaa caaattcaag aagaaaagtc attgaatcc cctcaaaact
6661 ctcctgcaac agaacaaaca atctttgatt cacagacatt tactgaaact gaactcaaaa
6721 ccacagatta ttctgtacta acaacaaaga aaacttacag tgatgataaa gaaatgaagg
6781 aggaagacac ttctttagtt aacatgtcta ctccagatcc agatgcaaat ggcttggaat
6841 cttacacaac tctccctgaa gctactgaaa agtcacattt ttcttagct actgcattag
6901 taactgaatc tataccagct gaacatgtag tcacagattc accaatcaaa aaggaagaaa
6961 gtacaaaaca ttttccgaaa ggcatggaca caacaattca agagtcagat actgagctct
7021 tattctctgg actgggatca ggagaagaag tttacctac tctaccaaca gagtcagtga
7081 attttactga agtggaacaa atcaataaca cattatatcc ccacacttct caagtggaaa
7141 gtacctcaag tgacaaaatt gaagacttta acagaatgga aaatgtggca aaagaagttg
7201 gaccactcgt atctcaaaca gacatctttg aaggtagtgg gtcagtaacc agcacaacat
7261 taatagaaat tttaagtgac actggagcag aaggacccac ggtggcacct ctccctttct
7321 ccacggacat cggacatcct caaaatcaga ctgtcaggtg gcagaagaa atccagacta
7381 gtagaccaca aaccataact gaacaagact ctaacaagaa ttcttcaaca gcagaaatta
7441 acgaaacaac aacctcatct actgattttc tggctagagc ttatggtttt gaaatggcca
7501 aagaatttgt tacatcagca ccaaaaccat tgactgta ttatgaacct tctggagaag
7561 gatctggaga agtggatatt gttgatcat ttcacactcc tgcaactact caggcaacca
7621 gacaagaaag cagcaccaca ttgttctcg atgggtccct ggaaaaacat cctgaggtgc
7681 caagcgctaa agctgttact gctgatggat tcccaacagt ttcagtgatg ctgcctcttc

Figure 5A (con't)

```
7741 attcagagca gaacaaaagc tccctgatc caactagcac actgtcaaat acagtgtcat
7801 atgagaggtc cacagacggt agtttccaag accgtttcag ggaattcgag gattccacct
7861 taaaacctaa cagaaaaaaa cccactgaaa atattatcat agacctggac aaagaggaca
7921 aggatttaat attgacaatt acagagagta ccatccttga aattctacct gagctgacat
7981 cggataaaaa tactatcata gatattgatc atactaaacc tgtgtatgaa gacattcttg
8041 gaatgcaaac agatatagat acagaggtac catcagaacc acatgacagt aatgatgaaa
8101 gtaatgatga cagcactcaa gttcaagaga tctatgaggc agctgtcaac ctttctttaa
8161 ctgaggaaac atttgagggc tctgctgatg ttctggctag ctacactcag gcaacacatg
8221 atgaatcaat gacttatgaa gatagaagcc aactagatca catgggcttt cacttcacaa
8281 ctgggatccc tgctcctagc acagaaacag aattagacgt tttacttccc acggcaacat
8341 ccctgccaat tcctcgtaag tctgccacag ttattccaga gattgaagga ataaaaagctg
8401 aagcaaaagc cctggatgac atgtttgaat caagcacttt gtctgatggt caagctattg
8461 cagaccaaag tgaaataata ccaacattgg gccaatttga aaggactcag gaggagtatg
8521 aagacaaaaa acatgctggt cctctttttc agccagaatt ctcttcagga gctgaggagg
8581 cattagtaga ccatactccc tatctaagta ttgctactac ccaacttatg gatcagagtg
8641 taacgagagt gcctgatgtg atggaaggat ccaatccccc atattcact gatacaacat
8701 tagcagtttc aacatttgcg aagttgtctt ctcagacacc atcatctccc ctcactatct
8761 actcaggcag tgaagcctct ggacacacag agatccccca gcccagtgct ctgccaggaa
8821 tagacgtcgg ctcatctgta atgtccccac aggattcttt taaggaaatt catgtaaata
8881 ttgaagcaac tttcaaacca tcaagtgagg aataccttca cataactgag cctccctctt
8941 tatctcctga cacaaaatta gaaccttcag aagatgatgg taaacctgag ttattagaag
9001 aaatggaagc ttctcccaca gaacttattg ctgtggaagg aactgagatt ctccaagatt
9061 tccaaaacaa aaccgatggt caagtttctg gagaagcaat caagatgttt cccaccatta
9121 aaacacctga ggctggaact gttattacaa ctgccgatga aattgaatta gaaggtgcta
9181 cacagtggcc acactctact tctgcttctg ccacctatgg ggtcgaggca ggtgtggtgc
9241 cttggctaag tccacagact tctgagaggc ccacgctttc ttcttctcca gaaataaacc
9301 ctgaaactca agcagcttta atcagagggc aggattccac gatagcagca tcagaacagc
9361 aagtggcagc gagaattctt gattccaatg atcaggcaac agtaaaccct gtggaattta
9421 atactgaggt tgcaacacca ccattttccc ttctggagac ttctaatgaa acagatttcc
9481 tgattggcat taatgaagag tcagtggaag gcacggcaat ctatttacca ggacctgatc
9541 gctgcaaaat gaacccgtgc cttaacggag gcacctgtta tcctactgaa acttcctacg
9601 tatgcacctg tgtgccagga tacagcggag accagtgtga acttgatttt gatgaatgtc
9661 actctaatcc ctgtcgtaat ggagccactt gtgttgatgg ttttaacaca ttcaggtgcc
9721 tctgccttcc aagttatgtt ggtgcacttt gtgagcaaga tacgagaca tgtgactatg
9781 gctggcacaa attccaaggg cagtgctaca aatactttgc ccatcgacgc acatgggatg
9841 cagctgaacg ggaatgccgt ctgcagggtg cccatctcac aagcatcctg tctcacgaag
9901 aacaaatgtt tgttaatcgt gtgggccatg attatcagtg gataggcctc aatgacaaga
9961 tgtttgagca tgacttccgt tggactgatg gcagcacact gcaatacgag aattggagac
10021 ccaaccagcc agacacagctc ttttctgctg gagaagactg tgttgtaatc atttggcatg
10081 agaatggcca gtggaatgat gttccctgca attaccatct cacctatacg tgcaagaaag
10141 gaacagttgc ttgcggccag ccccctgttg tagaaaatgc aagacctttg gaaagatga
10201 aacctcgtta tgaaatcaac tccctgatta gataccactg caaagatggt ttcattcaac
10261 gtcaccttcc aactatccgg tgcttaggaa atggaagatg ggctatacct aaaattacct
```

Figure 5A (con't)

```
10321 gcatgaaccc atctgcatac caaaggactt attctatgaa atactttaaa aattcctcat
10381 cagcaaagga caattcaata aatacatcca aacatgatca tcgttggagc cggaggtggc
10441 aggagtcgag gcgctgatcc ctaaaatggc gaacatgtgt tttcatcatt tcagccaaag
10501 tcctaacttc ctgtgccttt cctatcacct cgagaagtaa ttatcagttg gtttggattt
10561 ttggaccacc gttcagtcat tttgggttgc cgtgctccca aaacatttta aatgaaagta
10621 ttggcattca aaaagacagc agacaaaatg aaagaaaatg agagcagaaa gtaagcattt
10681 ccagcctatc taatttcttt agttttctat ttgcctccag tgcagtccat ttcctaatgt
10741 ataccagcct actgtactat ttaaaatgct caatttcagc accgatggcc atgtaaataa
10801 gatgatttaa tgttgatttt aatcctgtat ataaaataaa aagtcacaat gagtttgggc
10861 atatttaatg atgattatgg agccttagag gtctttaatc attggttcgg ctgcttttat
10921 gtagtttagg ctggaaaatgg tttcacttgc tctttgactg tcagcaagac tgaagatggc
10981 ttttcctgga cagctagaaa acacaaaatc ttgtaggtca ttgcacctat ctcagccata
11041 ggtgcagttt gcttctacat gatgctaaag gctgcgaatg ggatcctgat ggaactaagg
11101 actccaatgt cgaactcttc tttgctgcat tcctttttct tcacttacaa gaaaggcctg
11161 aatggaggac ttttctgtaa ccagg
```

Figure 5A (con't)

Human CSPG2 amino acid sequence GenPept Accession No. NP_004376 (SEQ ID NO: 4)

```
   1 LHKVKVGKSP PVRGSLSGKV SLPCHFSTMP TLPPSYNTSE FLRIKWSKIE VDKNGKDLKE
  61 TTVLVAQNGN IKIGQDYKGR VSVPTHPEAV GDASLTVVKL LASDAGLYRC DVMYGIEDTQ
 121 DTVSLTVDGV VFHYRAATSR YTLNFEAAQK ACLDVGAVIA TPEQLFAAYE DGFEQCDAGW
 181 LADQTVRYPI RAPRVGCYGD KMGKAGVRTY GFRSPQETYD VYCYVDHLDG DVFHLTVPSK
 241 FTFEEAAKEC ENQDARLATV GELQAAWRNG FDQCDYGWLS DASVRHPVTV ARAQCGGGLL
 301 GVRTLYRFEN QTGFFPPDSR FDAYCFKPKE ATTIDLSILA ETASPSLSKE FQMVSDRTTP
 361 IIPLVDELPV IPTEFPPVGN IVSFEQKATV QPQAITDSLA TKLPTPTGST KKPWDMDDYS
 421 PSASGPLGKL DISEIKEEVL QSTTGVSHYA TDSWDGVVED KQTQESVTQI EQIEVGPLVT
 481 SMEILKHIPS KEFPVTETPL VTARMILESK TEKKMVSTVS ELVTTCHYGF TLGEEDDEDR
 541 TLTVGSDEST LIFDQIPEVI TVSKTSEDTI HTHLEDLESV SASTTVSPLI MPDNNGSSMD
 601 DWEERQTSGR ITEEFLGKYL STTPFPSQHR TEIELSFYSG DKILVEGIST VIYPSLQTEM
 661 THRKERTETL IPEMRTDTYT DEIQEEITKS PFMGKTEEEV FSGMKLSTSL SEPIHVTESS
 721 VEMTKSFDFP TLITKLSAEP TEVRDMEEDF TATPGTTKYD ENITTVLLAH GTLSVEAATV
 781 SKWSWDEDNT TSKPLESTEP GASSKLPPAL LTTVGMNGKD KDIPSFTEDG ADEFTLIPDS
 841 TQKQLEEVTD EDIAAHGKFT IRFQPTTSTG IAEKSTLRDS TTEEKVPPIT STEGQVYATM
 901 PGSALGEVED VDLSKPVSTV PQFAHTSEVE GLAFVSYSST QEPTTYVDSS RTIPLSVIPK
 961 TDWGVLVPSV PSEDEVLGEP SQDILVIEQT RLEATISPET MRTTKITEGT TQEEFPWKEQ
1021 TAEKPVPALS STAWTPKEAV TPLDEQEGDG SAYTVSEDEL LTGSERVPVL ETTPVGKIDH
1081 SVSYPPGAVT EHKVRTDEVV TLTPRIGPKV SLSPGPEQKY ETEGSSTTGF TSSLSPFSTH
1141 ITQLMEETTT EKTSLEDIDL GSGLFEKPKA TELIEFSTIK VTVPSDITTA FSSVDRLHTT
1201 SAFKPSSAIT KKPPLIDREP GEETISDMVI IGESTSHVPP TTLEDIVAKE TETDIDREYF
1261 TTSSPPATQP TRPPTVEDKE AFGPQALSTP QPPASTKFHP DINVYIIEVR ENKTGRMSDL
1321 SVIGHPIDSE SKEDEPCSEE TDPVHDLMAE ILPEFPDIIE IDLYHSEENE EEEEECANAT
1381 DVTTTPSVQY INGKHLVTTV PKDPEAESAR RGQFESVAPS QNFSDSSESD TRPFVIAKTE
1441 LSTAVQPNES TETTESLEVT WKPETYPETS EHFSGGEPDV FPTVPFHEEF ESGTAKKGAE
1501 SVTERDTEVG HQAHERTEPV SLFEEESSGE IAIDQESQKI AFARATEVTF GEEVEKSTSV
1561 TYTPTIVPSS ASAYVSEEEA VTLIGNPWPD DLLSTKESWV EATPRQVVEL SGSSSIPITE
1621 GSGEAEEDED TMPTMVTDLS QRNTTDFLIT LDTSRIITES FFEVPATTIY PVSEQPSAKV
1681 VPTKFVSETD TSEWISSTTV EEKRRKEEEC TTGTASTFEV YSSTQRSDQL ILPFELESPN
1741 VATSSDSGTK KSFMSLTTFT QSEREMTDST PVFTETNTLE NLGAQTTEHS SIHQPGVQEG
1801 LTTLFRSPAS VFMEQGSCEA AAPPETITVS SFSLNVEYAI QAEKEVACTL SPHVETTFST
1861 EPTGLVLSTV MDRVVAENIT QTSREIVISE RLGEPNYGAE IRGFSTGFPL EEDFSGDFRE
1921 YSTVSHPIAK EETVRMECSG DAAFRDTQTS PSTVPTSVRI SHISDSECPS STMVSTSAFP
1981 WEEFTSSAEG SGEQLVTVSS SVVPVLPSAV QKFSGTASSI IDEGLGEVGT VNEIDRRSTI
2041 LFTAEVGTRK APVEKEEVKV SGTVSTNFPQ TIEPAKLWSR QEVNPVRQEI ESETTSEEQI
2101 QEEKSFESPQ NSPATEQTIF DSQTFTETEL KTTDYSVLTT KKTYSDDKEM KEEDTSLVNM
2161 STPDPDANGL ESYTTLPEAT EKSHFFLATA LVTESIPAEH VVTDSPIKKE ESTKHFPKGM
2221 RPTIQESDTE LLFSGLGSGE EVLPTLPTES VNFTEVEQIR NTLYPHTSQV ESTSSDKIED
2281 FNRMENVAKE VGPLVSQTDI FEGSGSVTST TLIEILSDTG AEGPTVAPLP FSTDIGHPQR
2341 QTVRWAEEIQ TSRPQTITEQ DSNKNSSTAE INETTTSSTD FLARAYGFEM AKEFVTSAPK
2401 PSDLYYEPSG EGSGEVDIVD SFRTSATTQA TRQESSTTFV DDGSLERHPE VFSAKAVTAD
2461 GFPTVSVMLF LHSEQNKSSP DPTSTLSNTV SYERSTDGSF QDRFREFEDS TLKPNRKKPT
2521 ENIIIDLDKE DKDLILTITE STILEILPEL TSDKNTIIDI DHTKPVYEDI LGMQTDIDTE
2581 VPSEPHDSND ESNDDSTQVQ EIYEAAVNLS LTEETFEGSA DVLASYTQAT HDESMTYEDR
2641 SQLDHMGFHF TTGIPAPSTE TELDVLLPTA TSLFIPRKSA TVIPEIBGIK AEAKALDDMF
2701 ESSTLSDGQA IADQSEIIPT LGQFERTQEE YEDKKHAGPS FQPEFSSGAE EALVDHTPYL
2761 SIATTHLMDQ SVTEVPDVME GSNPPYYFDT TLAVSTFAKL SSQTPSSPLT IYSGSEASGH
2821 TEIPQPSALP GIDVGSSVMS PQDSFKEIHV NIEATFKPSS EEYLHITEFP SLSPDTKLEP
2881 SEDDGKPELL EEMEASFTEL IAVEGTEILQ DFQNKTDGQV SGEAIKMFFT IKTPEAGTVI
2941 TTADEIELEG ATQWPHSTSA SATYGVEAGV VPWLSPQTSF RPTLSSSPEI NPETQAALIR
```

Figure 5B

```
3001 GQDSTIAASE QQVAARILDS NDQATVNPVE FNTEVATPPF SLLETSNETD FLIGINEESV
3061 EGTAIYLPGP DRCKMNPCLN GGTCYPTETS YVCTCVPGYS GDQCELDFDE CHSNPCRNGA
3121 TCVDGFNTFR CLCLPSYVGA LCEQDTETCD YGWHKFQGQC YKYFAHRRTW DAAERECRLQ
3181 GAHLTSILSH EEQMFVNRVG HDYQWIGLND KMFEHDFRWT DGSTLQYENW RPNQPDSFFS
3241 AGEDCVVIIW RENGQWNDVP CNYHLTYTCK KGTVACGQPP VVENAKTFGK MKPRYEINSL
3301 IRYHCKDGFT QRHLPTIRCL GNGRWAIPKI TCMNPSAYQR TYSMKYFKNS SSAKDNSINT
3361 SKHDHRWSRR WQESRR
//
```

Figure 5B (con't)

Homo sapiens IQ motif containing GTPase activating protein 1 (IQGAP1), mRNA
NCBI Reference Sequence: NM_003870.3 (SEQ ID NO: 5)

```
   1 ggaccccggc aagcccgcgc acttggcagg agctgtagct accgccgtcc gcgcctccaa
  61 ggtttcacgg cttcctcagc agagactcgg gctcgtccgc catgtccgcc gcagacgagg
 121 ttgacgggct gggcgtggcc cggccgcact atggctctgt cctggataat gaaagaactta
 181 ctgcagagga gatggatgaa aggagacgtc agaacgtggc ttatgagtac ctttgtcatt
 241 tggaagaagc gaagaggtgg atggaagcat gcctagggga agatctgcct cccaccacag
 301 aactggagga ggggcttagg aatgggggtct accttgccaa actggggaac ttcttctctc
 361 ccaaagtagt gtccctgaaa aaatctatg atcgagaaca gaccagatac aaggcgactg
 421 gcctccactt tagacacact gataatgtga ttcagtggtt gaatgccatg gatgagattg
 481 gattgcctaa gatttttac ccagaaacta cagatatcta tgatcgaaag aacatgccaa
 541 gatgtatcta ctgtatccat gcactcagtt tgtacctgtt caagctaggc ctggccctc
 601 agattcaaga cctatatgga aaggttgact tcacagaaga agaaatcaac aacatgaaga
 661 ctgagttgga gaagtatggc atccagatgc ctgcctttag caagattggg ggcatcttgg
 721 ctaatgaact gtcagtggat gaagccgcat acatgctgc tgttattgct attaatgaag
 781 ctattgaccg tagaattcca gccgacacat tgcagctttg aaaaatccg aatgccatgc
 841 ttgtaaatct tgaagagccc ttggcatcca cttaccagga tatactttac caggctaagc
 901 aggacaaaat gacaaatgct aaaaacagga cagaaaactc agagagagaa agagatgttt
 961 atgaggagct gctcacgcaa gctgaaattc aaggcaatat aaacaaagtc aatacatttt
1021 ctgcattagc aaatatcgac ctggctttag aacaaggaga tgcactggcc ttgttcaggg
1081 ctctgcagtc accagcctg gggcttcgag gactgcagca acagaatagc gactggtact
1141 tgaagcagct cctgagtgat aaacagcaga agagacagag tggtcagact gacccccctgc
1201 agaaggagga gctgcagtct ggagtggatg ctgcaaacag tgctgcccag caatatcaga
1261 gaagattggc agcagtagca ctgattaatg ctgcaatcca gaagggtgtt gctgagaaga
1321 ctgttttgga actgatgaat cccgaagccc agctgcccca ggtgtatcca tttgccgccg
1381 atctctatca gaaggagctg gctaccctgc agcgacaaag tcctgaacat aatctcaccc
1441 acccagagct ctctgtcgca gtggagatgt tgtcatcggt ggccctgatc aacaggggcat
1501 tggaatcagg agatgtgaat acagtgtgga agcaattgag cagttcagtt actggtctta
1561 ccaatattga ggaagaaaac tgtcagaggt atctcgatga gttgatgaaa ctgaaggctc
1621 aggcacatgc agagaataat gaattcatta catggaatga tatccaagct tgcgtggacc
1681 atgtgaacct ggtggtgcaa gaggaacatg agaggatttt agccattggt taattaatg
1741 aagccctgga tgaaggtgat gcccaaaaga ctctgcaggc cctacagatt cctgcagcta
1801 aacttgaggg agtccttgca gaagtggccc agcattacca agacacgctg attagagcga
1861 agagagagaa agcccaggaa atccaggatg agtcagctgt gttatggtt gatgaaatc
1921 aaggtggaat ctggcagtcc aacaaagaca cccaagaagc acagaagttt gccttaggaa
1981 tcttgccat taatgaggca gtagaaagtg gtgatgttgg caaaacactg agtgccttc
2041 gctcccctga tgttggcttg tatgagtca tccctgagtg tggtgaaact taccacagtg
2101 atcttgctga agccaagaag aaaaaactgg cagtaggaga taataacagc aagtgggtga
2161 agcactgggt aaaaggtgga tattattatt accacaatct ggagacccag gaaggaggat
2221 gggatgaacc tccaaatttt gtgcaaaatt ctatgcagct ttctcgggag gagatccaga
2281 gttctatctc tggggtgact gccgcatata acgagaaca gctgtggctg gccaatgaag
2341 gcctgatcac caggctgcag gctcgctgcc gtggatactt agttcgacag gaattccgat
2401 ccaggatgaa tttcctgaag aaacaaatcc ctgccatcac ctgcattcag tcacagtgga
```

Figure 6A 2461 gaggatacaa gcagaagaag gcatatcaag atcggttagc ttacctgcgc tcccacaaag
2521 atgaagttgt aaagattcag tccctggcaa ggatgcacca agctcgaaag cgctatcgag
2581 atcgcctgca gtacttccgg gaccatataa atgacattat caaaatccag gcttttattc
2641 gggcaaacaa agctcgggat gactacaaga ctctcatcaa tgctgaggat cctcctatgg
2701 ttgtggtccg aaaatttgtc cacctgctgg accaaagtga ccaggatttt caggaggagc
2761 ttgacccttat gaagatgcgg gaagaggtta tcaccctcat tcgttctaac cagcagctgg
2821 agaatgacct caatctcatg gatatcaaaa ttggactgct agtgaaaaat aagattacgt
2881 tgcaggatgt ggtttcccac agtaaaaaac ttaccaaaaa aaataaggaa cagttgtctg
2941 atatgatgat gataaataaa cagaagggag gtctcaaggc tttgagcaag gagaagagag
3001 agaagttgga agcttaccag cacctgtttt attattgca aaccaatccc acctatctgg
3061 ccaagctcat ttttcagatg ccccagaaca agtccaccaa gttcatggac tctgtaatct
3121 tcacactcta caactacgcg tccaaccagc gagaggagta cctgctcctg cggctctta
3181 agacagcact ccaagaggaa atcaagtcga aggtagatca gattcaagag attgtgacag
3241 gaaatcctac ggttattaaa atggttgtaa gttcaaccg tggtgcccgt ggccagaatg
3301 ccctgagaca gatcttggcc ccagtcgtga aggaaattat ggatgacaaa tctctcaaca
3361 tcaaaactga ccctgtggat atttacaaat cttgggttaa tcagatggag tctcagacag
3421 gagaggcaag caaactgccc tatgatgtga cccctgagca ggcgctagct catgaagaag
3481 tgaagacacg gctagacagc tccatcagga acatgcgggc tgtgacagac aagtttctct
3541 cagccattgt cagctctgtg gacaaaatcc cttatgggat gcgcttcatt gccaaagtgc
3601 tgaaggactc gttgcatgag aagttccctg atgctggtga ggatgagctg ctgaagatta
3661 ttggtaactt gctttattat cgatacatga atccagccat tgttgctcct gatgcctttg
3721 acatcattga cctgtcagca ggaggccagc ttaccacaga ccaacgccga aatctgggct
3781 ccattgcaaa aatgcttcag catgctgctt ccaataagat gttctgggga gataatgccc
3841 acttaagcat cattaatgaa tatctttccc agtcctacca gaaattcaga cggttttcc
3901 aaactgcttg tgatgtccca gagcttcagg ataaatttaa tgtggatgag tactctgatt
3961 tagtaaccct caccaaacca gtaatctaca tttccattgg tgaaatcatc aacacccaca
4021 ctctcctgtt ggatcaccag gatgccattg ctccggagca caatgatcca atccacgaac
4081 tgctggacga cctcggcgag gtgccccacca tcgagtccct gataggggaa agctctggca
4141 atttaaatga cccaaataag gaggcactgg ctaagacgga agtgtctctc acctgacca
4201 acaagttcga cgtgcctgga gatgagaatg cagaaatgga tgctcgaacc atcttactga
4261 atacaaaacg tttaattgtg gatgtcatcc ggttccagcc aggagagacc ttgactgaaa
4321 tcctagaaac accagccacc agtgaacagg aagcagaaca tcagagagcc atgcagagac
4381 gtgctatccg tgatgccaaa acacctgaca agatgaaaaa gtcaaaatct gtaaaggaag
4441 acagcaacct cactcttcaa gagaagaaag agaagatcca gacaggttta aagaagctaa
4501 cagagcttgg aaccgtggac ccaaagaaca aataccagga actgatcaac gacattgcca
4561 gggatattcg gaatcagcgg aggtaccgac agaggagaaa ggccgaacta gtgaaactgc
4621 aacagacata cgctgctctg aactctaagg ccacctttta tgggagcag gtggattact
4681 ataaaagcta tatcaaaacc tgcttggata cttagccag caagggcaaa gtctccaaaa
4741 agcctaggga aatgaaagga aagaaaagca aaaagattc tctgaaatat acagcagcaa
4801 gactacatga aaaaggagtt cttctggaaa ttgaggacct gcaagtgaat cagtttaaaa
4861 atgttatatt tgaaatcagt ccaacagaag aagttggaga cttcgaagtg aaagccaaat
4921 tcatgggagt tcaaatggag acttttatgt tacattatca ggacctgctg cagctacagt
4981 atgaaggagt tgcagtcatg aaattattg atagagctaa agtaaatgtc aacctcctga
5041 tcttccttct caacaaaaag ttctacggga agtaattgat cgtttgctgc cagcccagaa

Figure 6A (con't)

```
5101 ggatgaagga aagaagcacc tcacagctcc tttctaggtc cttctttcct cattggaagc
5161 aaagacctag ccaacaacag cacctcaatc tgatacactc ccgatgccac attttaact
5221 cctctcgctc tgatgggaca tttgttaccc tttttcata gtgaaatgt gtttcaggct
5281 tagtctgacc tttctggttt cttcattttc ttccattact taggaaagag tggaaactcc
5341 actaaaattt ctctgtgttg ttacagtctt agaggttgca gtactatatt gtaagctttg
5401 gtgtttgttt aattagcaat agggatggta ggattcaaat gtgtgtcatt tagaagtgga
5461 agctattagc accaatgaca taaatacata caagacacac aactaaaatg tcatgttatt
5521 aacagttatt aggttgtcat ttaaaaataa agttccttta tatttctgtc ccatcaggaa
5581 aactgaagga tatggggaat cattggttat cttccattgt gttttctttt atggacagga
5641 gctaatggaa gtgacagtca tgttcaaagg aagcatttct agaaaaaagg agataatgtt
5701 tttaaatttc attatcaaac ttgggcaatt ctgtttgtgt aactcccga ctagtggatg
5761 ggagagtccc attgctaaaa ttcagctact cagataaatt cagaatgggt caaggcacct
5821 gcctgttttt gttggtgcac agagattgac ttgattcaga gagacaattc actccatccc
5881 tatggcagag gaatgggtta gccctaatgt agaatgtcat tgttttaaa actgttttat
5941 atcttaagag tgccttatta agtatagat gtatgtctta aaatgtgggt gataggaatt
6001 ttaaagattt atataatgca tcaaaagcct tagaataaga aaagcttttt ttaaattgct
6061 ttatctgtat atctgaactc ttgaaacttt tagctaaaac actaggattt atctgcagtg
6121 ttcagggaga taattctgcc tttaattgtc taaaacaaaa acaaaaccag ccaacctatg
6181 ttacacgtga gattaaaacc aatttttttcc ccatttttttc tcctttttc tcttgctgcc
6241 cacatttgtgc ctttatttta tgagccccag ttttctgggc ttagtttaaa aaaaaaatca
6301 agtctaaaca ttgcatttag aaagcttttg ttcttggata aaaagtcata cactttaaaa
6361 aaaaaaaaaa cttttttccag gaaaatatat tgaaatcatg ctgctgagcc tctatttct
6421 ttctttgatg ttttgattca gtattctttt atcataaatt tttagcattt aaaaattcac
6481 tgatgtacat taagccaata aactgcttta atgaataaca aactatgtag tgtgtccta
6541 ttataaatgc attggagaag tattttatg agactcttta ctcaggtgca tggttacagc
6601 ccacagggag gcatggagtg ccatggaagg attcgccact acccagacct tgttttttgt
6661 tgtattttgg aagacaggtt ttttaaagaa acatttttct cagattaaaa gatgatgcta
6721 ttacaactag cattgcctca aaaactggga ccaaccaaag tgtgtcaacc ctgtttcctt
6781 aaaagaggct atgaatccca aaggccacat ccaagacagg caataatgag cagagtttac
6841 agctccttta ataaaatgtg tcagtaattt taaggtttat agtccctca acacaattgc
6901 taatgcagaa tagtgtaaaa tgcgcttcaa gaatgttgat gatgatgata tagaattgtg
6961 gctttagtag cacagaggat gcccccaacaa actcatggcg ttgaaaccac acagttctca
7021 ttactgttat ttattagctg tagcattctc tgtctcctct ctctcctcct ttgacctttct
7081 cctcgaccag ccatcatgac atttaccatg aatttacttc ctcccaagag tttggactgc
7141 ccgtcagatt gttgctgcac atagttgcct ttgtatctct gtatgaaata aaaggtcatt
7201 tgttcatgtt aaaaaaaaa
```

Figure 6A (con't)

NCBI Reference Sequence: NP_003861.1
IQ motif containing GTPase activating protein 1 [Homo sapiens] (SEQ ID NO: 6)

```
   1  MSAADEVDGL  GVARPRYGSV  LDNERLTAEE  MDERRRQNVA  YEYLCHLEEA  KRWMEACLGE
  61  DLPPTTELEE  GLRNGVYLAK  LGNFFSPKVV  SLKKIYDREQ  TRYKATGLHF  RHTDNVIQWL
 121  NAMDEIGLPK  IFYPETTDIY  DRKNMPRCIY  CIHALSLYLF  KLGLAPQIQD  LYGKVDFTEE
 181  EINNMKTELE  KYGIQMPAFS  KIGGILANEL  SVDEAALHAA  VIAINEAIDR  RIPADTFAAL
 241  KNPNAMLVNL  EEPLASTYQD  ILYQAKQDKM  TRAKNRIERS  ERERDVYEEL  LTQAEIQGNI
 301  NKVNTFSALA  NIDLALEQGD  ALALFRALQS  PALGLRGLQQ  QNSDWYLKQL  LSDKQQKRQS
 361  GQTDPLQKEE  LQSGVDAANS  AAQQYQRRIA  AVALINAAIQ  KGVAERTVLE  LMNPEAQLPQ
 421  VYPFAADLYQ  KELATLQSQS  PEHNLTHPEL  SVAVEMLSSV  ALINKALESG  DVNTVWKQLS
 481  SSVTGLTNIE  EENCQRYLDE  LMKLAAQASA  ENNEFITWND  IQACVDRVNL  VVQEEHERIL
 541  AIGLINEALD  EGDAQKTLQA  LQIPAAKLEG  VLAEVAQHYQ  DLLTRAKRER  AQEIQDESAV
 601  LWLDEIQGGI  WQSNKDTQEA  QKFALGIFAI  NEAVESGDVG  KILSALRSPD  VGLYGVIPEC
 661  GETYHSDLAE  AKKKLAVGD   NNSKWVRHWV  KGGYYYHNL   ETQEGGWDEF  PNFVQNSMQL
 721  SREEIQSSIS  GVTAAYNREQ  LWLANEGLIT  RLQARCRGYL  VRQEFRSRMN  FLKKQIPAIT
 781  CIQSQWRGYK  QKKAYQDRLA  YLRSHKDEVV  KIQSLARMRQ  ARKRYRDRLQ  YFRDHINDII
 841  KIQAFIRANK  ARDDYKTLIN  AEDPPMVVVR  KFVHLLDQSD  QDFQEELDLM  KMREEVITLI
 901  RSNQQLENDL  NLMDIKIGLL  VKNKITLQDV  VSRSKKLTKK  NKEQLSDMMM  INKQKGGLKA
 961  LSKEKREKLE  AYQHLFYLLQ  TNPTYLAKLI  FQMPQNKSTK  FMDSVIFTLY  NYASNQREEY
1021  LLLRLFKTAL  QEEIKSKVIQ  IQEIVTGNPT  VIKMVVSFNR  GARGQNALRQ  ILAPVVKEIM
1081  DDKSLNIKTD  PVDIYKSWVN  QMESQTGEAS  KLPYDVTPEQ  ALAHEEVKTR  LDSSIRNMRA
1141  VTDKFLSAIV  SSVDKIPYGM  RFIAKVLKDS  LHEKFPDAGE  DELLKIIGNL  LYYRYMNPAI
1201  VAPDAFDYID  LSAGGQLTTD  QRRNLGSIAK  MLQHAASNKM  FLGDNAHLSI  INEYLSQSYQ
1261  KFRRFPQTAC  DVPELQDKFN  VDEYSDLVTL  TRPVIYISIG  EIINTHTLLL  DHQDAIAPEH
1321  NDPIHELLDD  LGEVPTIESL  IGESSGNLND  PNKEALAKTE  VSLTLTNKFD  VPGDENAEMD
1381  ARTILLNTKR  LIVDVIRFQF  GETLTEILET  PATSEQEAEH  QRAMQRRAIR  DAKTPDKMKK
1441  SKSVKEDSNL  TLQEEKEKIQ  TGLRKLTELG  TVDPKNRYQE  LINDIARDIR  NQRRYRQRRK
1501  AELVKLQQTY  AALNSKATFY  GEQVDYYKSY  IKTCLDNLAS  KGKVSKKPRE  MKGKKSKKIS
1561  LKYTAARLHE  KGVLLEIEDL  QVNQFKNVIF  EISPTEEVGD  FEVKAKFMGV  QMETFMLHYQ
1621  DLLQLQYEGV  AVMKLFDRAK  VNVNLLIFLL  NKKFYGK
```

Figure 6B

NCBI Reference Sequence: NM_000607.2
Homo sapiens orosomucoid 1 (ORM1), mRNA (SEQ ID NO: 7)

```
  1 acagagtaaa cttttgctgg gctccaagtg accgcccata gtttattata aaggtgactg
 61 caccctgcag ccaccagcac tgcctggctc cacgtgcctc ctggtctcag tatggcgctg
121 tcctgggttc ttacagtcct gagcctccta cctctgctgg aagcccagat cccattgtgt
181 gccaacctag tacggtgcc catcaccaac gccaccctgg acggatcac tggcaagtgg
241 ttttatatcg catcggcctt tcgaaacgag gagtacaata gtcggttca ggagatccaa
301 gcaaccttct tttacttcac ccccaacaag acagaggaca cgatctttct cagagagtac
361 cagaccgac aggaccagtg catctataac accacctacc tgaatgtcca gggggaaaat
421 ggaccatct ccagatacgt gggaggccaa gagcatttcg ctcacttgct gatcctcagg
481 gacaccaaga cctacatgct tgctttgac gtgaacgatg agaagaactg ggggctgtct
541 gtctatgctg acaagccaga gacgaccaag gagcaactgg agagttcta cgaagctctc
601 gactgcttgc gcattccaa gtcagatgtc gtgtacaccg attggaaaaa ggataagtgt
661 gagccactgg agagcagca cgagaaggag aggaaacagg aggaggggga atcctagcag
721 gacacagcct tggatcagga cagagacttg ggggccatcc tgcccctcca accgacatg
781 tgtacctcag cttttccct cacttgcatc aataaagctt ctgtgtttgg aacagctaaa
841 aaaaaa
```

Figure 7A

NCBI Reference Sequence: NP_000598.2
orosomucoid 1 precursor [Homo sapiens] (SEQ ID NO: 8)

```
  1 MALSWVLTVL SLLPLLEAQI PLCANLVPVP ITNATLDRIT GKWFYIASAF RNEEYNKSVQ
 61 EIQATFFYFT PNKTEDTIFL REYQTRQDQC IYNTTYLNVQ RENGTISRYV GGQEHFAHLL
121 ILRDTKTYML AFDVNDEKNW GLSVYADKPE TTKEQLGEFY EALDCLRIPK SDVVYTDWKK
181 DKCEPLEKQH EKERKQEEGE S
```

Figure 7B

Homo sapiens arginase, liver (ARG1), mRNA
NCBI Reference Sequence: NM_000045.2 (SEQ ID NO: 9)

```
   1 tgtcactgag ggttgactga ctggagagct caagtgcagc aaagagaagt gtcagagcat
  61 gagcgccaag tccagaacca tagggattat tggagctcct ttctcaaagg gacagccacg
 121 aggaggggtg gaagaaggcc ctacagtatt gagaaaggct ggtctgcttg agaaacttaa
 181 agaacaagag tgtgatgtga aggattatgg ggacctgccc tttgctgaca tccctaatga
 241 cagtcccttt caaattgtga agaatccaag gtctgtggga aaagcaagcg agcagctggc
 301 tggcaaggtg gcagaagtca agaagaacgg aagaatcagc ctggtgctgg gcggagacca
 361 cagtttggca attggaagca tctctggcca tgccagggtc caccctgatc ttggagtcat
 421 ctgggtggat gctcacactg atatcaacac tccactgaca accacaagtg gaaacttgca
 481 tggacaacct gtatctttcc tcctgaagga actaaaagga aagattcccg atgtgccagg
 541 attctcctgg gtgactccct gtatatctgc caaggatatt gtgtatattg gcttgagaga
 601 cgtggaccct ggggaacact acattttgaa aactctaggc attaaatact ttcaatgac
 661 tgaagtggac agactaggaa ttggcaaggt gatggaagaa acactcagct atctactagg
 721 aagaaagaaa aggccaattc atctaagttt tgatgttgac ggactggacc catctttcac
 781 accagctact ggcacaccag tcgtgggagg tctgacatac agagaaggtc tctacatcac
 841 agaagaaatc tacaaaacag ggctactctc aggattagat ataatggaag tgaacccatc
 901 cctggggaag acaccagaag aagtaactcg aacagtgaac acagcagttg caataacctt
 961 ggcttgtttc ggacttgctc gggagggtaa tcacaagcct attgactacc ttaacccacc
1021 taagtaaatg tggaaacatc cgatataaat ctcatagtta atggcataat tagaaagcta
1081 atcattttct taagcataga gttatccttc taaagacttg ttctttcaga aaaatgtttt
1141 tccaattagt ataaactcta caaattccct cttggtgtaa aattcaagat gtggaaattc
1201 taacttttt gaaatttaaa agcttatatt ttctaacttg gcaaaagact tatccttaga
1261 aagagaagtg tacattgatt tccaattaaa aatttgctgg cattaaaaat aagcacactt
1321 acataagccc ccatacatag agtgggactc ttggaatcag gagacaaagc taccacatgt
1381 ggaaaggtac tatgtgtcca tgtcattcaa aaaatgtgat tttttataat aaactcttta
1441 taacaag
//
```

Figure 8A

NCBI Reference Sequence: NP_000036.2
arginase 1 [Homo sapiens]  (SEQ ID NO: 10)

```
  1 MSAKSRTIGI IGAPFSKGQP RGGVEEGPTV LRKAGLLEKL KEQECDVKDY GDLPFADIPN
 61 DSPFQIVKNP RSVGKASEQL AGKVAEVKKN GRISLVLGGD HSLAIGSISG HARVHPDLGV
121 IWVDAHTDIN TPLTTTSGNL HGQPVSFLLK ELKGKIPDVP GFSWVTPCIS AKDIVYIGLR
181 DVDPGEHYIL KTLGIKYFSM TEVDRLGIGK VMEETLSYLL GRKKRPIHLS FDVDGLDPSF
241 TPATGTPVVG GLTYREGLYI TEEIYKTGLL SGLDIMEVNP SLGKTPEEVT RTVNTAVAIT
301 LACFGLAREG NHKPIDYLNP PK
```

Figure 8B

Homo sapiens lymphocyte antigen 96 (LY96), mRNA
NCBI Reference Sequence: NM_015364.3 (SEQ ID NO: 11)

```
  1 agttaaatct tttctgctta ctgaaaagga agagtctgat gattagttac tgatcctctt
 61 tgcatttgta aagctttgga gatattgaat catgttacca tttctgtttt tttccaccct
121 gttttcttcc atatttactg aagctcagaa gcagtattgg gtctgaaat catccgatgc
181 aagtatttca tacacctact gtgataaaat gcaatacca attcaatta atgttaacc
241 ctgtatagaa ttgaaaagat ccaaaggatt attgcacatt ttcacattc caaggagaga
301 tttaaagcaa ttatatttca atctctatat aactgtcaac acaatgaatc ttccaaagcg
361 caaagaagtt atttgccgag gatctgatga cgattactct ttttgcagag ctctgaaggt
421 agagactgtg aatacaacaa tatcattctc cttcaaggga ataaaatttt ctaagggaaa
481 atacaaatgt gttgttgaag ctatttctgg gagcccagaa gaaatgctct tttgcttgga
541 gtttgtcatc ctacaccaac ctaattcaaa ttagaataaa ttgagtattt aaaaaaaaaa
601 aaaaaaaaa aaaaaaaaa
//
```

Figure 9A

Homo sapiens matrix metallopeptidase 9 (gelatinase B, 92kDa gelatinase, 92kDa type IV collagenase) (MMP9), mRNA (NCBI Reference Sequence: NM_004994.2) (SEQ ID NO: 12)

```
   1 agacacctct gccctcacca tgagcctctg gcagccctg gtcctggtgc tcctggtgct
  61 gggctgctgc tttgctgccc ccagacagcg ccagtccacc cttgtgctct tccctggaga
 121 cctgagaacc aatctcaccg acaggcagct ggcagaggaa tacctgtacc gctatggtta
 181 cactcgggtg gcagagatgc gtggagagtc gaaatctctg gggcctgcgc tgctgcttct
 241 ccagaagcaa ctgtccctgc ccgagaccgg tgagctggat agcgccacgc tgaaggccat
 301 gcgaacccca cggtgcgggg tccagacct gggcagattc caaaccttg agggcgacct
 361 caagtggcac caccacaaca tcacctattg gatccaaaac tactcggaag acttgccgcg
 421 ggcggtgatt gacgacgcct ttgcccgcgc cttcgcactg tgagcgcgg tgacgccgct
 481 caccttcact cgcgtgtaca gccgggacgc agacatcgtc atccagtttg gtgtcgcgga
 541 gcacggagac gggtatccct tcgacgggaa ggacgggctc ctggcacacg cctttcctcc
 601 tggccccggc attcagggag acgcccattt cgacgatgac gagttgtggt ccctgggcaa
 661 gggcgtcgtg gttccaactc ggtttggaaa cgcagatggc gcggcctgcc acttcccctt
 721 catcttcgag ggccgctcct actctgcctg caccaccgac ggtcgctccg acggcttgcc
 781 ctggtgcagt accacggcca actacgacac cgacgaccgg tttggcttct gccccagcga
 841 gagactctac acccaggacg gcaatgctga tgggaaaccc tgccagttc cattcatctt
 901 ccaaggccaa tcctactccg cctgcaccac ggacggtcgc tccgacggct accgctggtg
 961 cgccaccacc gccaactacg accgggacaa gctcttcggc ttctgccgcga cccgagctga
1021 ctcgacggtg atggggggca actcggcggg ggagctgtgc gtcttccctt tcacttcct
1081 gggtaaggag tactcgacct gtaccagcga gggccgcgga gatgggcgcc tctggtgcgc
1141 taccacctcg aactttgaca gcgacaagaa gtggggcttc tgccccgacc aaggatacag
1201 tttgttcctc gtggcggcgc atgagttcgg ccacgcgctg gcttagatc attcctcagt
1261 gccggaggcg ctcatgtacc ctatgtaccg cttcactgag gggccccct tgcataagga
1321 cgacgtgaat ggcatccggc acctctatgg tcctcgccct gaacctgagc cacggcctcc
1381 aaccaccacc acaccgcagc ccacggctcc ccgacggtc tgcccacg gaccccccac
1441 tgtccaccc tcagagcgcc ccacagctgg cccacaggt ccccctcag ctggccccac
1501 aggtccccc actgctggcc cttctacggc cactactgtg cctttgagtc cggtggacga
1561 tgcctgcaac gtgaacatct tcgacgccat cgcggagatt gggaaccagc tgtatttgtt
1621 caaggatggg aagtactggc gattctctga gggcagggg agccggccgc agggcccctt
1681 ccttatcgcc gacaagtggc ccgcgctgcc ccgcaagctg gactcggtct tgaggagcg
1741 gctctccaag aagcttttct tcttctctgg gcgccaggtg tgggtgtaca caggcgcgtc
1801 ggtgctgggc ccgaggcgtc tggacaagct gggcctggga gccgacgtgg cccaggtgac
1861 cggggccctc cggagtggca gggggaagat gctgctgttc agcgggcgc gcctctggag
1921 gttcgacgtg aaggcgcaga tggtggatcc ccggagcgcc agcgaggtgg accggatgtt
1981 ccccgggtgt cctttggaca cgcacgacgt cttccagtac cgagagaaag cctatttctg
2041 ccaggaccgc ttctactggc gcgtgagttc ccggagtgag ttgaaccagg tggaccaagt
2101 gggctacgtg acctatgaca tcctgcagtg ccctgaggac tagggctccc gtcctgcttt
2161 ggcagtgcca tgtaaatccc cactgggacc aaccctgggg aaggagccag tttgccggat
2221 acaaactggt attctgttct ggaggaaagg gaggagtgga ggtgggctgg gccctctctt
2281 ctcaccttg tttttgttg gagtgtttct aataaacttg gattctctaa cctttaaaaa
2341 aaaaaaaaaa aaaaaaaaaa aaaaaaaaaa aaaaaaaaaa aaaaaa
```

Figure 9B

NCBI Reference Sequence: NP_004985.2
matrix metalloproteinase 9 preproprotein [Homo sapiens] (SEQ ID NO: 13)

```
  1 MSLWQPLVLV LLVLGCCFAA PRQRQSTLVL FPGDLRTNLT DRQLAEEYLY RYGYTRVAEM
 61 RGESKSLGPA LLLLQKQLSL PETGELDSAT LKAMRTPRCG VPDLGRFQTF EGDLKWHHHN
121 ITYWIQNYSE DLPRAVIDDA FARAFALWSA VTPLTFTRVY SRDADIVIQF GVAEHGDGYP
181 FDGKDGLLAH AFPPGPGIQG DAHFDDDELW SLGKGVVVPT RFGNADGAAC HFPFIFEGRS
241 YSACTTDGRS DGLPWCSTTA NYDTDDRFGF CPSERLYTQD GNADGKPCQF PFIFQGQSYS
301 ACTTDGRSDG YRWCATTANY DRDKLFGFCP TRADSTVMGG NSAGELCVFP FTFLGKEYST
361 CTSEGRGDGR LWCATTSNFD SDKKWGFCPD QGYSLFLVAA HEFGHALGLD HSSVPEALMY
421 PMYRFTEGPP LHKDDVNGIR HLYGPRPEPE PRPPTTTTPQ PTAPPTVCPT GPPTVHPSER
481 PTAGPTGPPS AGPTGPPTAG PSTATTVPLS PVDDACNVNI FDAIAEIGNQ LYLFKDGKYW
541 RFSEGRGSRP QGPFLIADKW PALPRKLDSV FEERLSKKLF FFSGRQVWVY TGASVLGPRR
601 LDKLGLGADV AQVTGALRSG RGKMLLFSGR RLWRFDVKAQ MVDPRSASEV DRMFPGVPLD
661 THDVFQYREK AYFCQDRFYW RVSSRSELNQ VDQVGYVTYD ILQCPED
//
```

Figure 10A

NCBI Reference Sequence: NP_056179.2
LY96 protein precursor [Homo sapiens] (SEQ ID NO: 14)

```
  1 MLPFLFFSTL FSSIFTEAQK QYWVCNSSDA SISYTYCDKM QYPISINVNP CIELKRSKGL
 61 LHIFYIPRRD LKQLYFNLYI TVNTMNLPKR KEVICRGSDD DYSFCRALKG ETVNTTISFS
121 FKGIKFSKGK YKCVVEAISG SPEEMLFCLE FVILRQPNSN
//
```

Figure 10B

Homo sapiens carbonic anhydrase IV (CA4), mRNA
NCBI Reference Sequence: NM_000717.3 (SEQ ID N0: 15)

```
ORIGIN
        1 cgctataaaa cccaggccgg caggatcgct gcacccgcgg cggcctcctc ggtgcgcgac
       61 ccccggctca gaggactctt tgctgtcccg caagatgcgg atgctgctgg cgctcctggc
      121 cctctccgcg gcgcggccat cggccagtgc agagtcacac tggtgctacg aggttcaagc
      181 cgagtcctcc aactaccct gcttggtgcc agtcaagtgg ggtggaaact gccagaagga
      241 ccgccagtcc cccatcaaca tcgtcaccac caaggcaaag gtggacaaaa aactgggacg
      301 cttcttcttc tctggctacg ataagaagca aacgtggact gtccaaaata cgggcactc
      361 agtgatgatg ttgctggaga acaaggccag catttctgga ggaggactgc ctgccccata
      421 ccaggccaaa cagttgcacc tgcactggtc cgacttgcca tataagggct cggagcacag
      481 cctcgatggg gagcactttg ccatggagat gcacatagta catgagaaag agaagggac
      541 atcgaggaat gtgaagaggg cccaggaccc tgaagacgaa attgcggtgc tggcctttct
      601 ggtggaggct ggaaccaggg tgaacgaggg cttccagcca ctggtggagg cactgtctaa
      661 tatcccaaa cctgagatga gcactacgat ggcagagagc agcctgttgg acctgctccc
      721 caaggaggag aaactgaggc actacttccg ctacctgggc tcactcacca cacgacctg
      781 cgatgagaag gtcgtctgga ctgtgttccg ggagcccatt cagcttcaca gagaacagat
      841 cctggcattc tctcagaagc tgtactacga caaggaacag acagtgagca tgaaggacaa
      901 tgtcaggccc ctgcagcagc tggggcagcg cacggtgata aagtccgggg cccgggtcg
      961 gccgctgccc tgggccctgc ctgccctgct gggcccatg ctggcctgcc tgctggccgg
     1021 cttcctgcga tgatggctca cttctgcacg cagcctctct gttgcctcag ctctccaagt
     1081 tccaggcttc cggtccttag ccttcccagg tgggacttta ggcatgatta aaatatggac
     1141 atatttttgg agaaaaaaaa aaaaa
//
```

Figure 11A

NCBI Reference Sequence: NP_000708.1 carbonic anhydrase IV precursor [Homo sapiens] (SEQ ID NO: 16)

```
  1 MRMLLALLAL SAARPSASAE SHWCYEVQAE SSNYPCLVPV KWGGNCQKDR QSPINIVTTK
 61 AKVDKKLGRF FFSGYDKKQT WTVQNNGHSV MMLLENKASI SGGGLPAPYQ AKQLRLHWSD
121 LPYKGSEHSL DGEHFAMEMH IVREKEKGTS RNVKEAQDPE DEIAVLAFLV EAGTQVNEGF
181 QPLVEALSNI PKPEMSTTMA ESSLLDLLPK EEKLRHYFRY LGSLTTPTCD EKVVWTVFRE
241 PIQLHREQIL AFSQKLYYDK EQTVSMKDNV RPLQQLGQRT VIKSGAPGRP LPWALPALLG
301 PMLACLLAGF LR
//
```

Figure 11B

NCBI Reference Sequence: NM_005621.1
Homo sapiens S100 calcium binding protein A12 (S100A12), mRNA (SEQ ID NO: 17)

```
  1 accactgctg gcttttgct gtagctccac attcctgtgc attgagggt taacattagg
 61 ctgggaagat gacaaaactt gaagagcatc tggagggaat tgtcaatatc ttccaccaat
121 actcagttcg gaagggcat tttgacaccc tctctaaggg tgagctgaag cagctgctta
181 caaggagct tgcaaacacc atcaagaata tcaaagataa agctgtcatt gatgaaatat
241 tccaaggcct ggatgctaat caagatgaac aggtcgactt tcaagaattc atatcctgg
301 tagccattgc gctgaaggct gcccattacc acacccacaa agagtaggta gctctctgaa
361 ggcttttac ccagcaatgt cctcaatgag ggtctttct ttccctcacc aaaacccagc
421 cttgcccgtg gggagtaaga gttaataaac acactcacga aaagtt
//
```

Figure 12A

NCBI Reference Sequence: NP_005612.1
S100 calcium-binding protein A12 [Homo sapiens] (SEQ ID NO: 18)

```
  1 MTKLEEHLEG IVNIFHQYSV RKGHFDTLSK GELKQLLTKE LANTIKNIKD KAVIDEIFQG
 61 LDANQDEQVD FQEFISLVAI ALKAAHYHTH KE
//
```

Figure 12B

BIOMARKERS FOR ACUTE ISCHEMIC STROKE

INCORPORATION BY REFERENCE

This application claims priority to U.S. Provisional Application Ser. No. 61/307,233, filed Feb. 23, 2010, the entire contents of which are incorporated herein by reference.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

GOVERNMENT SUPPORT

This application was supported by a pre-doctoral Intramural Research Training Award via the Graduate Partnerships Program through the National Institute of Nursing Research, National Institutes of Health. This research presented in this application was also supported by the Division of Intramural Research of the National Institute of Neurological Disorders and Stroke (Grant No. Z01 AG000957-05), and the Laboratory of Neurogenetics, National Institute of Aging National Institutes of Health. Accordingly, the Government may have certain rights in this invention.

BACKGROUND OF THE INVENTION

1. Field of the Invention

The present invention relates to the identification and use of diagnostic markers for acute ischemic stroke. In a various aspects, the invention relates to methods for rapid and early detection of acute ischemic stroke, as well as the identification of individuals at risk for acute ischemic stroke.

2. Background

Stroke is clinically defined as a rapidly developing syndrome of vascular origin that manifests itself in focal loss of cerebral function. In more severe situations, the loss of cerebral function is global. Stroke can be categorized into two broad types, "ischemic stroke" (about 87%) and "hemorrhagic stroke" (about 10%). Ischemic stroke occurs when the blood supply to the brain is suddenly interrupted. Hemorrhagic stroke happens when a blood vessel located in our around the brain bursts leading to the leakage and accumulation of blood directly in the brain tissue. Additionally, a patient may experience transient ischemic attacks, which indicates a high risk for the future development of a more severe episode. Stroke also includes subarachnoid hemorrhage (about 3%).

The symptoms of stroke often include numbness or weakness, especially on one side of the body; sudden confusion or trouble speaking or understanding speech; sudden trouble seeing in one or both eyes; sudden trouble walking; dizziness; or loss of balance or coordination. Stroke is the most common devastating neurologic disease in the world and despite recent progress understanding stroke mechanisms, stroke management is still not optimal.

Stroke is the third leading cause of death in the world, after only heart disease and cancer. In the United States alone, approximately 780,000 people experience a stroke each year, which contributes to an overall financial burden of over $65 billion per year. As noted, ischemic stroke accounts for most instances of stroke in patients, and consequently, the category of stroke having the greatest financial burden.

Ischemic stroke encompasses thrombotic, embolic, lacunar and hypoperfusion types of strokes. Thrombi are occlusions of arteries created in situ within the brain, while emboli are occlusions caused by material from a distant source, such as the heart and major vessels, often dislodged due to myocardial infarct or atrial fibrillation. Less frequently, thrombi may also result from vascular inflammation due to disorders such as meningitis. Thrombi or emboli can result from atherosclerosis or other disorders, for example, arteritis, and lead to physical obstruction of arterial blood supply to the brain. Lacunar stroke refers to an infarct within non-cortical regions of the brain. Hypoperfusion embodies diffuse injury caused by non-localized cerebral ischemia, typically caused by myocardial infarction and arrhythmia.

Of the 88% of ischemic strokes that occur each year, 8-12% results in death within 30 days. The risk of ischemic stroke is associated with various familial and environmental factors, such as the presence of hypertension, obesity, tobacco use, and a positive family history. Determinants of outcome include non-modifiable risk factors such as age, race, gender and genetic variation along with clinical phenotypes of severity, such as stroke scale score, the presence of fever and serologic blood markers. Advances in neuroimaging and acute clinical management have resulted in greater numbers of patients surviving the initial insult. However, morbidity remains high secondary to complications following the primary event and initial misdiagnosis.

The onset of ischemic stroke is often abrupt, and can begin with a manifestation of neurologic deficits that worsen over a 24-48 hour period. Stroke-associated symptoms commonly include unilateral neurologic dysfunction that extends progressively, without producing headache or fever. Early manifestations may rapidly progress to more severe symptoms within a few minutes.

Hemorrhagic stroke is caused by intracerebral or subarachnoid hemorrhage, i.e., bleeding into brain tissue, following blood vessel rupture within the brain. Intracerebral and subarachnoid hemorrhage are subsets of a broader category of hemorrhage referred to as intracranial hemorrhage. Intracerebral hemorrhage is typically due to chronic hypertension, and a resulting rupture of an arteriosclerotic vessel. Stroke-associated symptom(s) of intracerebral hemorrhage are abrupt, with the onset of headache and steadily increasing neurological deficits. Nausea, vomiting, delirium, seizures and loss of consciousness are additional common stroke-associated symptoms.

In contrast, most subarachnoid hemorrhage is caused by head trauma or aneurysm rupture which is accompanied by high blood pressure release which also causes direct cellular trauma. Prior to rupture, aneurysms may be asymptomatic, or occasionally associated with tension or migraine headaches. However, headache typically becomes acute and severe upon rupture, and may be accompanied by varying degrees of neurological deficit, vomiting, dizziness, and altered pulse and respiratory rates.

Transient ischemic attacks (TIAs) have a sudden onset and brief duration, typically 2-30 minutes. Most TIAs are due to emboli from atherosclerotic plaques, often originating in the arteries of the neck, and can result from brief interruptions of blood flow. The symptoms of TIAs are identical to those of stroke, but are only transient. Concomitant with underlying risk factors, patients experiencing TIAs are at a markedly increased risk for stroke.

There are few pharmaceutical therapies for treating stroke. In point of fact, the only Food and Drug Administration (FDA) approved treatment for ischemic stroke is recombinant issue plasminogen activator (rtPA), alteplase. Multiple attempts to identify other pharmacologic agents have resulted in negative findings; therefore a redirection of the science is necessary to understand the human variable response to stroke, in particular, to ischemic stroke, to provide alternative avenues for therapeutic treatment.

Since its commencement into the clinical arena in 1996, recombinant tissue plasminogen activator (rtPA) has proven to be a promising therapeutic treatment for ischemic stroke and is safe and effective for use in routine clinical practice. However, its powerful effects are not seen without significant clinical complications. In addition, rtPA is only approved for use when patients present to the hospital within three hours from onset of symptoms. The downside is that the median time from stroke symptom onset to presentation to the emergency department is 3-6 hours. A recent study addressed the possibility of extending this limited therapeutic time window and it was shown that intravenous rtPA given between 3 and 4.5 hours after onset of symptoms significantly improved clinical outcomes following ischemic stroke compared to placebo. This is promising given that the time window limit of 3 hours and a large list of contraindicating factors for thrombolytic therapy currently results in only 3-8% of stroke patients receiving rtPA.

The advancements of rtPA therapy aside, there is still a demand for alternative acute ischemic stroke therapies in clinical practice. Unfortunately, the results of recent clinical trials have demonstrated that there is still a gap in the understanding of the variable human response to ischemic stroke. Numerous promising pre-clinical therapeutics display insignificant clinical utility in human patients, which speaks to the difficulty of translating what is learned at the bench to the patient at the bedside.

These negative findings may be due in part to the complexity of the human physiologic response to ischemic stroke, limited knowledge about the multiple pathways interacting in response to ischemic stroke and the implications of genomic variability on individual recovery from ischemic stroke. The difficulty may also be attributable to insufficient classification of ischemic stroke subtype. It is possible that gene expression profiling can help to identify subtypes of ischemic stroke, which has tremendous utility in designing therapeutic strategies for treatment. A better understanding of stroke pathophysiology in humans and more appropriate stroke subtyping may provide the foundation needed to design appropriate therapeutics for battling ischemic stroke and other stroke types.

Immediate diagnosis and care of a patient experiencing stroke can be critical. As noted, tissue plasminogen activator (rtPA) given within three hours of symptom onset in ischemic stroke is beneficial for selected acute ischemic stroke patients. Patients may also benefit from anticoagulants (e.g., heparin) if they are not candidates for rtPA therapy. In contrast, thrombolytics and anticoagulants are strongly contraindicated in hemorrhagic strokes. Thus, early and rapid differentiation of ischemic stroke from hemorrhagic-type stroke is imperative and often critical. Delays in the confirmation of stroke diagnosis and the identification of stroke type limit the number of patients that may benefit from early intervention therapy.

Another limitation in the diagnosis of ischemic stroke relates to the fact that, due to the rapidity of onset and progression of acute ischemic stroke, circumstances are such that ischemic stroke patients are often not seen by clinicians having the appropriate knowledge and training to be able to provide a correct, life-saving diagnosis. For instance, brain imaging technology is an integral and key aspect of the clinical stroke evaluations. However, such technology is often not available. Even if the technology is available, proper interpretation of brain imaging results concerning stroke diagnoses is best suited for those clinicians who are highly and specifically trained in the treatment and care of stroke patients. Indeed, due to the rapid onset of an acute ischemic stroke and other factors, such as the scarcity of trained stroke-clinicians and neurologists, clinical assessment of a potential victim is often carried out by a non-stroke specialist, e.g., a family practitioner, paramedic or triage nurse. Thus, achieving an accurate and rapid early diagnosis is often not possible under present clinical circumstances.

Patients, even those with mild symptoms, may be eligible for various ischemic stroke therapies if they can be started within a few hours of symptom onset. Patients who do not receive such early therapies are at an increased risk of recurrent stroke, often occurring even within a matter of days. Thus, prompt administration of a suitable therapy in a timely manner can substantially increase the efficacy of treatment while reducing the risk of recurrent stroke.

However, presently there are no rapid diagnostic procedures or methods that can be used to reliably determine whether a patient has suffered a stroke, in particular, an acute ischemic stroke, or whether a subject is at risk for ischemic stroke.

Accordingly, a rapid diagnostic test capable of making an accurate clinical diagnosis of ischemic stroke irrespective of the clinician's level of stroke expertise or lack thereof would be extremely useful. To date, the identification of appropriate biomarkers for ischemic stroke have proven to be extremely difficult. This may be tied, in part, to the observation that the proteins associated with stroke-affected brain and neurological tissues are slow to be released into the blood due to the blood-brain barrier. In addition, many potential stroke markers, including markers of cerebral ischemia and inflammation, located in the blood are associated with other conditions that may mimic stroke, e.g., severe myocardial infarction and brain infection.

This invention solves these deficiencies in the art.

SUMMARY OF THE INVENTION

The present invention relates to the identification and use of diagnostic markers for acute ischemic stroke. The methods and compositions described herein can meet the need in the art for rapid, sensitive and specific diagnostic assay to be used in the diagnosis of acute ischemic stroke in patients or in the assessment of the risk of developing acute ischemic stroke. The methods and compositions can also be used to distinguish acute ischemic stroke from other various forms of stroke and TIAs and "stroke mimic" events. Moreover, the methods and compositions of the present invention can also be used to facilitate the treatment of stroke patients and the development of additional diagnostic and/or prognostic indicators.

Prior to this invention, the diagnosis of ischemic stroke has been difficult and inaccurate. These problems are due in part to limitations in the technology currently used to evaluate a patient for a stroke and limitations in the level of experience and/or proper training possessed by medical clinicians who engage the patients. These circumstances are detrimental to stroke victims because an accurate and quick diagnosis of acute ischemic stroke is extremely important to the health and outcome of the patients.

Brain imaging technology is an integral and key aspect of the clinical stroke evaluations but may suffer from a number of limitations, including lack of sensitivity and lack of availability. Moreover, proper interpretation of brain imaging results concerning stroke diagnoses is best suited for those clinicians who are highly and specifically trained in the treatment and care of stroke patients. Indeed, due to the rapid onset of an acute ischemic stroke and other factors, such as the scarcity of trained stroke-clinicians and neurologists, clinical assessment of a potential victim is often carried out by a non-stroke specialist, e.g., a family practitioner, paramedic or triage nurse. Thus, achieving an accurate and rapid early diagnosis is often not possible.

Patients, even those with mild symptoms, may be eligible for various ischemic stroke therapies if they can be started within a few hours of symptom onset. Patients who do not receive such early therapies are at an increased risk of recurrent stroke, often occurring even within a matter of days. Thus, prompt administration of a suitable therapy in a timely manner can substantially increase the risk of treatment while reduce the risk of recurrent stroke.

Accordingly, a rapid diagnostic test capable of making an accurate clinical diagnosis of ischemic stroke irrespective of the clinician's level of stroke expertise or lack thereof would be extremely useful. However, to date, the identification of appropriate blood biomarkers for ischemic stroke have proven to be extremely difficult. This may be tied, in part, to the observation that the proteins associated with stroke-affected brain and neurological tissues are slow to be released into the blood due to the blood-brain barrier. In addition, many potential stroke markers (including markers of cerebral ischemia and inflammation) located in the blood are associated with other conditions that may mimic stroke (e.g., severe myocardial infarction and brain infection). A recent comprehensive review of published blood-based stroke biomarkers revealed significant problems and weaknesses associated with currently published biomarkers, indicating that no single marker or panel of markers could be recommended for routine clinical practice.

Thus, at the time of the present invention, there remained a substantial need for a single biomarker or panel of biomarkers which were clinically effective in the diagnosis of acute ischemic stroke.

In one particular embodiment, using a gene expression profiling approach, this application describes obtaining peripheral blood samples from 39 stroke patients and 25 healthy controls at various times relative to the onset of acute ischemic stroke symptoms and then evaluated changes in gene expression profiles in both stroke and control groups over time. The gene expression profiles were analyzed to identify nine gene candidates having a likely role in acute ischemic stroke, thereby serving as biomarkers therefore.

Thus, in one aspect, the invention provides a set of biomarkers for use in methods for diagnosing acute ischemic stroke. In addition, the present invention is directed to compositions (e.g., arrays, probes, biomarker panels) that comprise the nine identified genes which can be used in the diagnosis of acute ischemic stroke and/or to distinguish acute ischemic stroke from TIAs and "stroke mimic" events. Further, since the biomarkers of the invention represent potential targets of intervention for the treatment of stroke, the biomarkers of the invention can be used in methods for screening compounds or agents that can treat acute ischemic stroke or a symptom thereof and which are detectable by the evaluation of the biomarkers of the invention.

In addition, the invention is directed to compositions that are useful in the detection of the biomarkers, including nucleic acid probes and antibodies that are specific for the biomarkers of the invention, as well as to compositions comprising purified biomarkers and their corresponding encoding nucleic acid molecules.

In a particular aspect, the present invention provides a method for the diagnosis of acute ischemic stroke in a subject, comprising detecting in a sample of whole peripheral blood obtained from the subject the presence of two or more biomarkers selected from the group consisting of: (a) chemokine receptor 7 (CCR7); (b) chondroitin sulfate proteoglycan 2 (CSPG2); (c) IQ motif-containing GTPase activation protein 1 (IQGAP1); (d) orosomucoid 1 (ORM1); (e) arginase 1 (ARG1); (f) lymphocyte antigen 96 (LY96); (g) matrix metalloproteinase 9 (MMP9); (h) carbonic anhydrase 4 (CA4); (i) s100 calcium binding protein A12 (s100A12); and wherein at least one of the biomarkers is (a), (b), (c) or (d), and wherein detection of the presence of the two or more biomarkers is indicative of acute ischemic stroke in the subject.

In one embodiment, the above method further comprises obtaining brain imaging data of the subject and evaluating the data to detect an acute ischemic stroke. The brain imaging data can be obtained through MRI or CT scan.

In another embodiment, the invention provides a method for identifying a candidate for acute ischemic stroke therapy using the biomarkers of the invention to diagnose acute ischemic stroke in a patient. The therapy can be the administration of a therapeutically effective amount of recombinant plasminogen activator (rtPA).

In yet another aspect, the invention provides a method for the diagnosis of acute ischemic stroke in a subject, comprising detecting in a biological sample obtained from the subject one or more biomarkers selected from the group consisting of: (a) chemokine receptor 7 (CCR7); (b) chondroitin sulfate proteoglycan 2 (CSPG2); (c) IQ motif-containing GTPase activation protein 1 (IQGAP1); and (d) orosomucoid 1 (ORM1).

In a further aspect, the invention provides a method for the diagnosis of acute ischemic stroke in a subject, comprising detecting in a biological sample obtained from the subject two or more biomarkers selected from the group consisting of: chemokine receptor 7 (CCR7); chondroitin sulfate proteoglycan 2 (CSPG2); IQ motif-containing GTPase activation protein 1 (IQGAP1); orosomucoid 1 (ORM1); arginase 1 (ARG1); lymphocyte antigen 96 (LY96); matrix metalloproteinase 9 (MMP9); carbonic anhydrase 4 (CA4); and s100 calcium binding protein A12 (s100A12), wherein at least one of the biomarkers is chemokine receptor 7 (CCR7); chondroitin sulfate proteoglycan 2 (CSPG2); IQ motif-containing GTPase activation protein 1 (IQGAP1); or orosomucoid 1 (ORM1).

In a still further aspect, the invention provides a method for differentiating an acute ischemic stroke from a transient ischemic attack (TIA), a hemorragic stroke and a stroke mimic in a subject presenting symptoms characteristic of a stroke or at risk of having a stroke, comprising:
(a) obtaining a biological sample from the patient;
(b) contacting the biological sample with a detection means capable of detecting the presence of at least one biomarker selected from the group consisting of: chemokine receptor 7 (CCR7); chondroitin sulfate proteoglycan 2 (CSPG2); IQ motif-containing GTPase activation protein 1 (IQGAP1); and orosomucoid 1 (ORM1), wherein the presence of at least one of the biomarkers in the biological sample is indicative of an acute ischemic stroke but not indicative of a transient ischemic attack (TIAs), hemorragic stroke or stroke mimic.

In other aspects, the invention provides a kit comprising a means for detecting one or more biomarkers diagnostic of acute ischemic stroke, said biomarkers being selected from the group consisting of:
(a) chemokine receptor 7 (CCR7);
(b) chondroitin sulfate proteoglycan 2 (CSPG2);
(c) IQ motif-containing GTPase activation protein 1 (IQGAP1); and
(d) orosomucoid 1 (ORM1).

In certain other aspects, the invention provides a filament-based diagnostic system comprising a panel of detectable polypeptides or functional polypeptide fragments thereof each corresponding to an acute ischemic stroke biomarker selected from the group consisting of:

(a) chemokine receptor 7 (CCR7);
(b) chondroitin sulfate proteoglycan 2 (CSPG2);
(c) IQ motif-containing GTPase activation protein 1 (IQ-GAP1); and
(d) orosomucoid 1 (ORM1).

In still other aspects, the invention provides a filament-based diagnostic system comprising a panel of detectable oligonucleotides each corresponding to an acute ischemic stroke biomarker selected from the group consisting of:

(a) chemokine receptor 7 (CCR7);
(b) chondroitin sulfate proteoglycan 2 (CSPG2);
(c) IQ motif-containing GTPase activation protein 1 (IQ-GAP1); and
(d) orosomucoid 1 (ORM1).

In still further aspects, the invention provides a filament-based diagnostic system comprising a panel of detectable antibodies each capable of specifically binding an acute ischemic stroke biomarker selected from the group consisting of:

(a) chemokine receptor 7 (CCR7);
(b) chondroitin sulfate proteoglycan 2 (CSPG2);
(c) IQ motif-containing GTPase activation protein 1 (IQ-GAP1); and
(d) orosomucoid 1 (ORM1).

In certain embodiments, the sample is or is obtained from whole peripheral blood from the subject.

In other embodiments, the method of the invention is executed on the subject no more than 3 hours after onset of presenting acute ischemic stroke symptoms. In still further embodiments, the method is executed on the subject no more than 4.5 hours after onset of presenting acute ischemic stroke symptoms.

Other embodiments of the invention provide that the detecting step comprises contacting the biological sample with a detection means capable of detecting the biomarker. The biomarker can be a nucleic acid molecule (e.g., mRNA) corresponding to or encoding one of (a) chemokine receptor 7 (CCR7); (b) chondroitin sulfate proteoglycan 2 (CSPG2); (c) IQ motif-containing GTPase activation protein 1 (IQ-GAP1); (d) orosomucoid 1 (ORM1); (e) arginase 1 (ARG1); (f) lymphocyte antigen 96 (LY96); (g) matrix metalloproteinase 9 (MMP9); (h) carbonic anhydrase 4 (CA4); or (i) s100 calcium binding protein A12 (s100A12).

In still other embodiments, the biomarker can be a polypeptide or active fragment thereof of (a) chemokine receptor 7 (CCR7); (b) chondroitin sulfate proteoglycan 2 (CSPG2); (c) IQ motif-containing GTPase activation protein 1 (IQGAP1); (d) orosomucoid 1 (ORM1); (e) arginase 1 (ARG1); (f) lymphocyte antigen 96 (LY96); (g) matrix metalloproteinase 9 (MMP9); (h) carbonic anhydrase 4 (CA4); or (i) s100 calcium binding protein A12 (s100A12).

Depending on the form of the biomarker of the invention (e.g., the mRNA or polypeptide of (a) chemokine receptor 7 (CCR7); (b) chondroitin sulfate proteoglycan 2 (CSPG2); (c) IQ motif-containing GTPase activation protein 1 (IQGAP1); (d) orosomucoid 1 (ORM1); (e) arginase 1 (ARG1); (f) lymphocyte antigen 96 (LY96); (g) matrix metalloproteinase 9 (MMP9); (h) carbonic anhydrase 4 (CA4); or (i) s100 calcium binding protein A12 (s100A12)), the detection means can be, but is not limited to, an antibody or oligonucleotide probe. The detection means can also be in the form of a kit or assay, such as a filament-based diagnostic system capable of detecting a polypeptide biomarker or a nucleic acid molecule biomarker of the invention.

In certain other embodiments, the inventive methods include treating the subject with a stroke therapy if the subject is diagnosed as having had an acute ischemic stroke or is at risk of therefore. The stroke therapy can include the administration of a therapeutically effective amount of recombinant plasminogen activator (rtPA).

In still other embodiments, the one or more detected biomarkers of the invention using the methods of the invention has at least a 1.5 fold increase or decrease in expression level as compared to the levels of the one or more biomarkers in a non-stroke subject.

In other embodiments, the one or more detectable biomarkers of the invention using the methods of the invention has at least a 2.0 fold increase or decrease in expression level as compared to the levels of the one or more biomarkers in a non-stroke subject.

In certain other embodiments of the invention, kits comprising a filament-based diagnostic system includes a surface on which is attached at known locations one or more oligonucleotides capable of hybridizing to the biomarkers.

In other embodiments of the invention, kits comprising a filament-based diagnostic system includes a surface on which is attached at known locations one or more antibodies capable of binding to the biomarkers. The surface can be a microarray, microtiter plate, membrane or the like. The kits may also include instructions for use.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1. Depicts the results of a nine-gene panel for ischemic stroke diagnosis. After comparison between both statistical packages there were 9 genes differentially expressed with at least a 2 fold difference in expression and Bonferroni corrected $p<0.05$ between stroke patients and control subjects. (ARG1, CA4, CCR7, CSPG2, IQGAP1, LY96, MMP9, ORM1, S100A12)

FIGS. 4A and 4B provide the nucleotide and amino acid sequences, respectively, for human CCR7.

FIGS. 5A and 5B provides the nucleotide and amino acid sequences, respectively, for human CSPG2.

FIGS. 6A and 6B provides the nucleotide and amino acid sequences, respectively, for human IQGAP1.

FIGS. 7A and 7B provides the nucleotide and amino acid sequences, respectively, for human ORM1.

FIGS. 8A and 8B provides the nucleotide and amino acid sequences, respectively, for human ARG1.

FIGS. 9A and 9B provides the nucleotide and amino acid sequences, respectively, for human LY96.

FIGS. 10A and 10B provides the nucleotide and amino acid sequences, respectively, for human MMP9.

FIGS. 11A and 11B provides the nucleotide and amino acid sequences, respectively, for human CA4.

FIGS. 12A and 12B provides the nucleotide and amino acid sequences, respectively, for human s100A12.

DETAILED DESCRIPTION OF THE INVENTION

Figure 2:
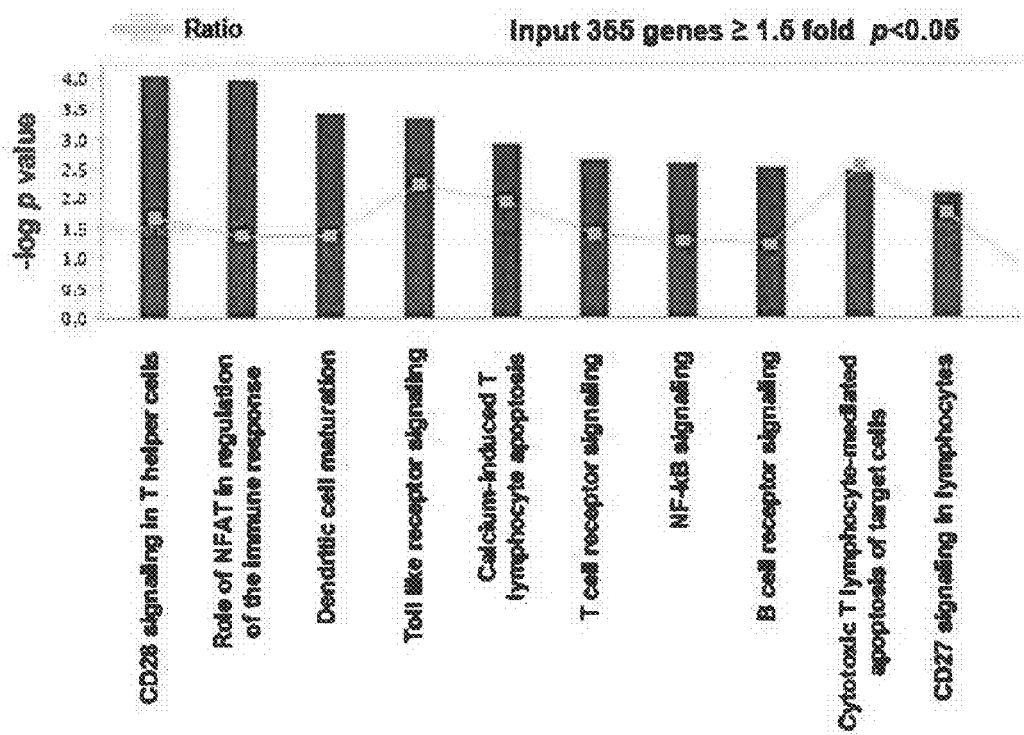
FIG. 2 provides a graph depicting the top pathways affected by acute ischemic stroke. A total of 355 genes with at least a 1.5 fold difference in expression between stroke patients and control subjects and a Bonferroni corrected $p<0.05$ were eligible for pathway analysis. A score, which was derived from a p value, was generated for each pathway; scores of 2 or higher are considered to have at least a 99% confidence of not being generated by chance alone. IPA analysis showed that the top 5 most significant canonical pathways in the peripheral blood of AICS patients were associated with CD28 signaling in T-helper cells ($p=4.03E00$), nuclear factor of activated T cells (NFAT) in regulation of the immune response ($p=4.03E00$) dendritic cell maturation ($p=3.4E00$), toll-like receptor signaling ($p=3.33E00$), and calcium-induced T-lymphocyte apoptosis ($p=2.92E00$).

The present invention is based, at least in part, on the unexpected discovery of certain biomarkers for acute ischemic stroke in peripheral blood. Accordingly, the present invention provides methods and compositions for the identification and use of biomarkers that are associated with the diagnosis and prognosis of acute ischemic stroke in a subject. Such biomarkers can be used in diagnosing and treating a subject for acute ischemic stroke and/or to monitor the course of an ischemic stroke treatment regimen; for screening subjects for the occurrence or risk of acute ischemic stroke; and for screening compounds and pharmaceutical compositions that might provide a benefit in treating or preventing such conditions.

Acute Ischemic Stroke

Acute ischemic stroke occurs when there is a decrease or loss of blood flow to an area of the brain resulting in tissue damage or destruction. It is the largest subtype of stroke pathologies and therefore accounts for the majority of the death and disability associated with stroke.

There are numerous scenarios that contribute to compromised cerebral perfusion; combine this with the multifactorial effects of the environment and individual genomic responses secondary to DNA variation and epigenetic DNA modification and the result is variability of patient presentation and recovery. This complexity makes ischemic stroke very difficult to treat, both medically and pharmacologically. Most cerebral ischemic pathologic conditions involve alterations in cerebrovascular reactivity and clot formation.

Ischemia is the consequence of one or more of the following causes: thrombosis, embolism or decreased systemic circulation. Thrombosis is a localized obstruction of blood flow in one or more blood vessels, most commonly caused by atherosclerosis. Stroke refers to a blockage of the blood vessel not caused by a localized process, but rather material originating from outside of the cerebral circulation, most commonly the heart. Decreased systemic perfusion results in a decrease in cerebral perfusion pressure, and ultimately cerebral blood flow secondary to cardiac pump failure or systemic hypotension.

Although each scenario has a different origin, the result is either a temporary or permanent decrease or loss of cerebral blood flow. Permanent loss of cerebral blood flow to an area of the brain resulting in cell death is termed infarction. The penumbra is the area of the brain receiving less than optimal blood flow and is damaged but "salvageable", not yet infarcted. In all cases of ischemic stroke, the intent of therapy is to rescue this penumbral tissue and if therapy or reperfusion occurs quickly, this tissue can be rescued. The extent of tissue damage depends on the location and duration of the infarction or lack of blood flow and the extent to which collateral vessels can supply oxygen and nutrients to compromised areas. The cerebral ischemic response is complex and involves a decrease in oxygen and glucose delivery but also an accumulation of detrimental metabolic waste products. Therefore reactive oxygen species (ROS) and inflammatory mediators play a critical role in the events following ischemia.

Immediately following ischemic brain injury a cascade of events occurs in response to loss of blood flow. Alterations at the cell membrane result in release of glutamate, activation of N-methyl-D-aspartic acid (NMDA) receptors and release of calcium (Ca+2) into the extracellular space. This process ultimately leads to the activation of Immediate Early Genes (IGE's), such as c-fos and c-jun. IGE's propagate the physiologic response by participating in transcription of neurotrophic factors (endogenous neuroprotection), heat shock proteins (general stress response), cytokines and immune mediated complexes (inflammatory and immune activation), and nitric oxide synthase (NOS) activation (neuronal stimulation). Pathway specific responses are mediated by non-modifiable factors (DNA variation, age, gender, and severity of injury), modifiable factors (diet, physical activity, temperature, and environmental stress) and the interaction of signaling molecules within the pathways themselves.

The collective response, secondary to human genetic variation, results in either propagation of injurious mechanisms and cell death or initiation of repair mechanisms and neuronal sustainment.

Since the brain does not store oxygen or glucose, cellular energy production fails to maintain normal metabolism within minutes following compromised cerebral blood flow. Within the mitochondria, the electron transport chain removes electrons from an electron donor and passes them onto oxygen to form water through a series of redox reactions. These reactions create a proton gradient across the mitochondrial membrane that drives production of adenosine triphosphate (ATP). ATP then enters the Krebs cycle (citric acid cycle) to become part of a metabolic pathway that converts carbohydrates, fats, and proteins into usable forms of energy (e.g. carbon dioxide and water). When oxygen is unavailable the electron transport chain can no longer accept electrons; a proton gradient is not produced, ATP production ceases, and pyruvate becomes the final acceptor of electrons in the chain. This switch from oxygen dependent aerobic metabolism to anaerobic energy production results in an accumulation of lactic acid and ionic pump failures.

Sodium potassium (Na+/K+) pumps are highly dependent upon ATP energy production and begin to fail within minutes of anaerobic metabolism. Na+, water and calcium (Ca+2) begin to pass from the extracellular space to the intracellular space and cerebral cells begin to swell, resulting in cytotoxic edema. Capillary endothelial cells begin to function abnormally and the tight junctions between them loose their integrity, leading to blood brain barrier (BBB) disruption. Intravascular fluid leaks into the extravascular space and spreads easily throughout the white matter, resulting in vasogenic edema. Additionally, excess intracellular $Ca^{+2}$ triggers free radical production along with free radicals produced during anaerobic metabolism contributing to protease and lipase activation. Superoxide and peroxynitrite (free radicals) production increases beyond the cells capacity to quench them, which in turn activates the production of other detrimental ROS. Eventually the swollen cells enter cell death pathways through necrotic or apoptotic processes dependent upon the cell type, severity of injury and the level of available ATP. Unfortunately, reoxygenation through reperfusion also acts as a substrate for enzymatic reactions that produce ROS. Cells attempt to minimize damage caused by ischemia by rebalancing energy supply and demand. This early neuroprotective response results in an overall suppression of non-essential energy consumption.

All of these events together result in blood-brain-barrier (BBB) permeability, loss of cell ion homeostasis, and excitotoxicity, resulting in a modulation of gene and protein expression. The molecular imprint of these processes is visible within all cells that migrate and circulate throughout the area of cerebral injury. These cells then circulate out of the central nervous system into the peripheral blood.

Clinical diagnosis of ischemic stroke is often difficult, complicated by its multiple etiologies and variable clinical presentation. In most hospitals, diagnosis is made when the patient presents with symptoms suggestive of acute cerebral ischemia in conjunction with pathologic findings on cerebral imaging that are most likely associated with the presenting symptoms. When possible, medical history is obtained via inquisition of the following: personal and family medical history; discussion of history of stroke or symptoms suggestive of stroke; time and activity at the onset of symptoms; temporal progression of symptoms; and whether or not they are accompanied by other factors, such as headache or nausea. Unfortunately more often than not, this information is unobtainable secondary to severity of the stroke and whether or not the patient has family available that can provide the history. At this point the physical examination and brain imaging findings are used to make the definitive diagnosis. Identifying the physical location of the stroke is made by assessment of neurologic status via the neurologic examination, which may include National Institutes of Health Stroke scale (NIHSS) score and the presence of pathologic findings on computed tomography (CT) or magnetic resonance imaging (MRI).

The majority of hospitals in the United States use CT to rule out stroke; however it has been found that CT is less than optimal for identifying acute ischemia. A recent study of emergency room (ER) neurology consults found that the initial diagnosis of the ER physician agrees with the final diagnosis ~60% of the time. There was a significant pattern of misdiagnosis for stroke and seizure; other benign medical conditions (e.g. migraine) and psychiatric disorders were originally diagnosed and medically treated as stroke. Although over-diagnosis of stroke early may appear to err on the side of patient safety, it puts a percentage of patients into a category where they are being treated for an acute stroke that they do not have. Given the complications associated with bleeding following rtPA administration, this practice is quite risky. For this reason, some ER physicians are reluctant to treat a patient with rtPA unless they are completely sure of a stroke diagnosis.

Where possible, hospitals are moving toward using MRI for acute diagnosis of stroke; however this is facilitated best by the presence of a dedicated stroke clinical team and only possible in facilities with 24 hour MRI availability. Additionally, even though rtPA is FDA approved, only a small number of stroke patients actually receive the drug. The Brain Attack Coalition has recommended a movement toward the creation of widespread primary stroke centers to increase the utilization of rtPA and creation of standards of care for ischemic stroke patients. In a small community hospital located in Bethesda, Md. the establishment of a primary stroke team resulted in a 7-fold increase in the proportion of stroke patients treated with rtPA within 24 months after the onset of the program. This paradigm can be applied to other small community hospitals and has the potential to increase the numbers of stroke patients treated with rtPA by an additional 30,000 patients per year. More and more hospitals are moving towards the establishment of primary stroke teams; however there are still quite a few hospitals that rely solely on the ER physician's expertise in diagnosing ischemic stroke.

Quick and definitive diagnosis in the acute care setting is essential to separate stroke from non-stroke, distinguish hemorrhage from ischemia, and identify the potential cause of the infarction, but most importantly to determine eligibility for thrombolytic therapy (e.g., rtPA-alteplase) to begin treatment within the three hour window of opportunity. An additional diagnostic measure, such as a serologic blood test or a screen of a panel of markers, would be extremely beneficial in obtaining a definitive diagnosis of acute stroke and increasing the utilization of rtPA, especially in hospitals where primary stroke centers are non-existent.

DEFINITIONS AND USE OF TERMS

The present invention may be understood more readily by reference to the following detailed description of preferred embodiments of the invention and the Examples included therein. Before the present methods and techniques are disclosed and described, it is to be understood that this invention is not limited to specific analytical or synthetic methods as such may, of course, vary. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this invention belongs.

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

As used herein, the term "antibody" refers to immunoglobulin molecules (e.g., any type, including IgG, IgE, IgM, IgD, IgA and IgY, and/or any class, including, IgG1, IgG2, IgG3, IgG4, IgA1 and IgA2) isolated from nature or prepared by recombinant means or chemically synthesized. The terms "antibody" and "immunoglobubin" can be used synonymously throughout the specification, unless indicated otherwise. Antibodies or immunoglobulins of the invention can be used for various purposes, including, for example, the detection of the biomarkers of the invention through the use of any suitable detection assay, e.g., ELISA.

As used herein, the terms "biological sample" or "patient sample" or "test sample" or "sample" as used herein, refer to a sample obtained from an organism or from components (e.g., cells) of a subject or patient for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. The sample may be of any biological tissue or fluid. The sample may be a clinical sample which is a sample derived from a patient. Such samples include, but are not limited to, brain cells or tissues, cerebrospinal fluid, nerve tissue, sputum, blood, serum, plasma, blood cells (e.g., white cells), tissue samples, biopsy samples, urine, peritoneal fluid, and pleural fluid, saliva, semen, breast exudate, tears, mucous, lymph, cytosols, ascites, amniotic fluid, bladder washes, and bronchioalveolar lavages or cells therefrom, among other body fluid samples. Preferably, the sample is peripheral blood. Preferable, the sample contains one or more of the biomarkers of the invention, or a nucleic acid encoding a biomarker of the invention (e.g., mRNA). The patient samples may be fresh or frozen, and may be treated, e.g. with heparin, citrate, or EDTA. Biological samples may also include sections of tissues such as frozen sections taken for histological purposes.

As used in this invention, the term "epitope" means any antigenic determinant on an antigen, e.g., a biomarker of the invention, to which an antibody binds through an antigenic binding site. Determinants or antigenic determinants on an antigen usually consist of chemically active surface groupings of molecules such as amino acids or sugar side chains and usually have specific three dimensional structural characteristics, as well as specific charge characteristics.

As used herein, the term antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. Alternatively, an antibody that specifically binds to an antigen, in accordance with this invention, refers to the binding of an antigen by an antibody or fragment thereof with a dissociation constant (IQ) of 104 or lower, as measured by a suitable detection instrument, e.g., surface plasmon resonance analysis using, for example, a BIACORE® surface plasmon resonance system and BIACORE® kinetic evaluation software (eg. version 2.1). The affinity or dissociation constant ($K_d$) for a specific binding interaction is preferably about 500 nM or lower, more preferably about 300 nM or lower and preferably at least 300 nM to 50 pM, 200 nM to 50 pM, and more preferably at least 100 nM to 50 pM, 75 nM to 50 pM, 10 nM to 50 pM.

The term "treatment" includes any process, action, application, therapy, or the like, wherein a subject (or patient), including a human being, is provided medical aid with the object of improving the subject's condition, directly or indirectly, or slowing the progression of a condition or disorder in the subject, or ameliorating at least one symptom of the disease or disorder under treatment.

The term "combination therapy" or "co-therapy" means the administration of two or more therapeutic agents to treat a disease, condition, and/or disorder, e.g., acute ischemic stroke. Such administration encompasses "co-administration" of two or more therapeutic agents in a substantially simultaneous manner. One therapy can be based on the biomarkers of the invention. A second therapy can be based on a known therapy for a disorder, e.g., acute ischemic stroke, such as tissue plasminogen activator (rtPA). The order of administration of two or more sequentially co-administered therapeutic agents is not limited.

The phrase "therapeutically effective amount" means the amount of each agent (e.g., an agent that beneficially interacts with a biomarker of the invention to treat acute ischemic stroke) administered that will achieve the goal of improvement in a disease, condition, and/or disorder severity, and/or symptom thereof, while avoiding or minimizing adverse side effects associated with the given therapeutic treatment.

The term "pharmaceutically acceptable" means that the subject item is appropriate for use in a pharmaceutical product.

The term "biomarker" or "marker" as used herein refers to proteins or polypeptides (or active fragment thereof) that are associated with brain tissue or neural cells, and which can be correlated with acute ischemic stroke, but are not correlated with other types of injury. Such specific biomarkers of acute ischemic stroke identified by the methods of the invention include (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12), and the like. These specific biomarkers are described in detail hereinafter. Biomarkers can be detected or identified or measured and the like using any suitable methods or instrumentation for measuring, identifying or detecting polypeptides or proteins. In certain embodiments, nucleic acids encoding the biomarkers can be measured, identified or detected using any suitable means by which to analyze nucleic acid molecules (e.g., mRNA molecules in peripheral blood encoding a biomarker of the invention). Where the detection or diagnosis is made through measuring, detecting, or the like of the nucleic acid molecules (e.g., mRNA) corresponding to or encoding a biomarker polypeptide of the invention, the term "biomarker" can also be in reference to the nucleic acid molecule itself. For example, a "biomarker" of the invention can include mRNA (or DNA) encoding (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12). Other biomarkers can be identified using the screening methods of the invention.

The term "active fragment of a biomarker" refers to a fragment of a biomarker having sufficient sequence such that it still possesses the same or substantially the same function as the full-size biomarker. Preferably, an active fragment of a biomarker retains at least 100% of the activity of the full-size biomarker, or at least 99%, 95%, 90%, 85%, 80% 75%, 70%, 65% or 60% of its activity. In certain embodiments, an active fragment of a biomarker is one which is immunologically detectable (i.e., detectable using an antibody).

"Proteins or polypeptides" used as biomarkers in the present invention are contemplated to include any fragments thereof, in particular, immunologically detectable fragments. One of skill in the art would recognize that proteins which are released by cells of the central nervous system which become damaged during a cerebral attack (e.g., acute ischemic stroke) could become degraded or cleaved into such fragments. Additionally, certain markers are synthesized in an inactive form, which may be subsequently activated, e.g., by proteolysis. Examples of such markers are described hereinafter. The term "related marker" as used herein refers to one or more fragments of a particular marker that may be detected as a surrogate for the marker itself. These related markers may be, for example, "pre," "pro," or "prepro" forms of biomarkers, or the "pre," "pro," or "prepro" fragment removed to form the mature marker. In preferred embodiments, these "pre," "pro," or "prepro" forms or the removed "pre," "pro," or "prepro" fragments are used in an equivalent fashion to the mature markers in the methods described herein.

The phrase "diagnosis" as used herein refers to methods by which the skilled artisan can estimate and/or determine whether or not a patient is suffering from, or is at some level of risk of developing, a given disease or condition. The skilled artisan (e.g., stroke clinician or emergency room physician) often makes a diagnosis on the basis of one or more diagnostic indicators, i.e., a biomarker, the risk, presence, absence, or amount of which is indicative of the presence, severity, or absence of the condition, e.g., acute ischemic stroke.

The term "interaction" refers to direct or indirect binding or alteration of a biological activity of a biomolecule, e.g., a biomarker.

The term "sensitivity", as used herein in the context of its application to diagnostic assays, refers to the proportion of all subjects with acute ischemic stroke or at risk for developing acute ischemic stroke that are correctly identified as such (that is, the number of true positives divided by the sum of the number of true positives and false negatives).

The term "specificity" of a diagnostic assay, as used herein in the context of its application to diagnostic assays, refers to the proportion of all subjects not having acute ischemic stroke or who are not at risk for developing acute ischemic stroke that are correctly identified as such (that is, the number of true negatives divided by the sum of the number of true negatives and false positives).

Within the context of the invention, the terms "detect", "detection" or "detecting" refer to the identification of the presence, absence, or quantity of a given biomarker.

As used herein, the term "acute ischemic stroke" refers to those patients having or at risk for "definite acute ischemic cerebrovascular syndrome (AICS)" as defined by the diagnostic criteria of Kidwell et al. "Acute Ischemic Cerebrovascular Syndrome: Diagnostic Criteria," Stroke, 2003, 34, pp. 2995-2998 (incorporated herein by reference). AICS diagnostic criteria are as follow:

Definite AICS: Acute onset of neurologic dysfunction of any severity consistent with focal brain ischemia AND imaging/laboratory CONFIRMATION of an acute vascular ischemic pathology.

Probable AICS: Acute onset of neurologic dysfunction of any severity suggestive of focal brain ischemic syndrome but WITHOUT imaging/laboratory CONFIRMATION of acute ischemic pathology* (diagnostic studies were negative but INSENSITIVE for ischemic pathology of the given duration, severity and location). Imaging, laboratory, and clinical data studies do not suggest nonischemic etiology: possible alternative etiologies ARE ruled out.

Possible AICS: Acute neurologic dysfunction of any duration or severity possibly consistent with focal brain ischemia WITHOUT imaging/laboratory CONFIRMATION of acute ischemic pathology* (diagnostic studies were not performed or were negative and SENSITIVE for ischemic pathology of the given duration, severity and location). Possible alternative etiologies are NOT ruled out. Symptoms may be nonfocal or difficult to localize.

Not AICS: Acute onset of neurologic dysfunction with imaging/laboratory CONFIRMATION of NONISCHEMIC pathology/(including normal imaging/laboratory studies that are highly sensitive for ischemic pathology of the given duration, severity, and location) as the cause of the neurologic syndrome.

As used herein, reference to "stroke symptoms" or "symptoms characteristic of a stroke" can refer to those symptoms that may present at the onset of any type of stroke (including acute ischemic and hemorrhagic stroke and others), including those symptoms recognized by the National Stroke Association (www.stroke.org), which are as follows: (a) sudden numbness or weakness of the face, arm or leg—especially on one side of the body; (b) sudden confusion, trouble speaking or understanding; (c) sudden trouble seeing in one or both eyes; (d) sudden trouble walking, dizziness, loss of balance or coordination, and (e) sudden severe headache with no known cause.

Biomarkers

In one aspect, the present invention provides biomarkers for diagnosing and detecting acute ischemic stroke in a patient at risk for ischemic stroke or who has already had a stroke event.

In one embodiment, the biomarkers include a 9-biomarker panel comprising: (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12). The biomarkers include both the polypeptides or nucleic acid molecules corresponding to the polypeptides, e.g., mRNA encoding the polypeptide biomarkers.

In other embodiments, the invention provides additional suitable biomarkers for detecting and diagnosing stroke events utilizing the biomarker screening methods of the invention as exemplified in the Examples. These screening methods relate to the surprising finding that biomarkers for stroke may be found by analyzing gene expression profiling of whole peripheral blood. Such methods can be utilized to identify other biomarkers for acute ischemic stroke, or other types of stroke or brain trauma.

The biomarkers of the invention, including the 9-biomarker panel identified herein, have various utilities, including, for example, their use in rapid blood tests to evaluate risk of acute ischemic stroke or to provide a diagnosis of acute ischemic stroke in a patient or to diagnose other forms of stroke or brain trauma.

As noted, a rapid blood test for the diagnosis of acute ischemic stroke would transform stroke care in the United States and throughout the world. Most hospitals across the U.S. are not large academic centers where stroke neurologists are available at all times and where an MRI can be used for acute assessment of cerebral ischemic changes prior to the administration of rtPA. The standard, however, is something quite different. More often than not, an emergency room (ER) physician would be given the task of assessing, diagnosing and treating acute ischemic stroke through clinical history assessment and CT without the assistance of a stroke-trained neurologist.

Recent studies have reinforced that although ER physicians are more than capable of treating stroke patients, they are often reluctant to administer stroke therapies (e.g., rtPA) unless the diagnosis is definitive. In addition, there is a shortage of trained emergency personnel and ER nursing staff capable of identifying stroke symptoms or conducting an appropriate stroke assessment. The small percentage of patients who actually receive rtPA (3-5%) and the large numbers of patients who leave the hospital (without treatment) with either a diagnosis of transient ischemic attack (TIA) or stroke of undetermined cause pays testament to the need to identify additional means of stroke diagnosis.

The skilled artisan will appreciate that peripheral blood markers specific for brain injury have proven virtually impossible to identify. Some groups have even begun to question the use of blood biomarkers in the study of acute brain injury. Numerous studies over the years have resulted in either insignificant findings or findings that could not be replicated. Traditional methods for the identification of these biomarkers have fallen short of the rigor and sensitivity necessary to identify such markers for brain injury, including ischemic stroke.

In one aspect, the present invention provides a "panel" of genes (or biomarkers) and their cognate encoded polypeptide products that can be used to detect or diagnose acute ischemic stroke. As shown in the Examples, the invention provides at least 9 genes identified by the methods of the invention that can predict acute ischemic stroke in a patient with a substantially high degree of accuracy as compared to MRI or CT based methods. Preferably, the predictive value of the 9 biomarker panel is at least 95%; or preferably at least 90%, 85%, 80%, 75%, 70%, 65%, or 60% accurate, as compared to the diagnostic capability of both MRI (85% accurate) and CT (54% accurate).

The 9-biomarker panel identified in this study comprises: (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12). Each of these biomarkers is described further as follows.

(1) Chemokine Receptor 7.

Chemokines are a family of small proteins that regulate leukocyte trafficking Aside from their role in inflammatory and immune responses there is increasing evidence that they play a significant role in glial cell proliferation and migration as part of the neuro-immune response. Several chemokines have been identified in both the serum and CSF (cerebralspinal fluid) of stroke patients. CXCL5, CCL2, CCL3, and CXCL8 are significantly increased following stroke and play a modulatory role of inflammation during the acute phase of ischemia. In addition CCR8 is expressed in activated microglia on brain sections of ischemic stroke patients. The down regulation of CCR7 in peripheral blood as shown by the methods of this invention (see Examples) suggests there is decreased glial cell proliferation and migration very early in the acute phase of ischemic stroke; which coincides with the literature that these cytokines become increasingly more active during recovery and repair. The human CCR7 mRNA sequence is publicly available as GenBank Accession No. NM_001838, the complete sequence of which is shown in FIG. 4A. The human CCR7 amino acid sequence is publicly available as GenPept Accession No. NP_001829, the complete sequence of which is shown in FIG. 4B.

(2) Chondroitin Sulfate Proteoglycan 2.

Chondroitin sulfate proteoglycan 2 (CSPG2) also known as versican, was first identified in hyaline cartilage where it provides mechanical support. Recent studies have identified CSPG2 as a primary component of the extracellular matrix in the CNS. A disaccharide degradation product of CSPG2 has been shown to stimulate microglia to possess increase phagocytic activity without cytotoxic effects. This suggests a role for CSPG2 in immune-related neurodengenerative disorders. In addition, increased CSPGs exhibit growth inhibiting properties and inhibit axonal sprouting within the glial scar. Within the infarct core CSPG2 expression is dramatically increased, resulting in increased cell death and reactive astrocytosis. Several enzymatic processes cleave CSPG2, including the matrix metalloproteinases. The up-regulation of CSPG2 as shown by the methods of this invention (see Examples) suggests there is inhibited axonal growth in the acute phase of ischemic stroke. The human CSPG2 mRNA sequence is publicly available as GenBank Accession No. NM_004385, the complete sequence of which is shown in FIG. 5A. The human CSPG2 amino acid sequence is publicly available as GenPept Accession No. NP_004376, the complete sequence of which is shown in FIG. 5B.

(3) IQ Motif-Containing GTPase Activation Protein 1 (IQGAP1).

IQ Motif-containing GTPase activating protein 1 (IQGAP1) is an evolutionarily conserved molecule that serves as a scaffold protein and plays a fundamental role in cell polarity. It modulates several cellular activities including cytoskeletal architecture, cell-cell adhesion, transcription and signaling (ERK signaling). Rho-family GTPases, including Cdc42 require IQGAP1 to regulate actin cytoskeleton and produce a gradient of signaling molecules. Cdc42 and IQGAP1 it co-localizes with actin filaments throughout the brain. In addition, increased Cdc42 activity has been implicated in the breakdown of the blood brain barrier (BBB). An up-regulation of IQGAP1 expression as shown by the methods of this invention (see Examples) suggests there is an increase in cellular signaling and transcription in the acute phase of ischemic stroke and IQGAP1 may mediate the disruption of the BBB as a means by which signals from the brain enter the periphery to augment cellular recruitment. The human IQGAP1 mRNA sequence is publicly available as GenBank Accession No. NM_003870, the complete sequence of which is shown in FIG. 6A. The human IQGAP1 amino acid sequence is publicly available as GenPept Accession No. NP_003861, the complete sequence of which is shown in FIG. 6B.

(4) Orosomucoid 1 (ORM1).

Oromucosid 1 (ORM1) also known as alpha-1 acid glycoprotein is an acute phase protein and increases 2-5 times during an acute phase response. It has been shown to suppress lymphocyte response to LPS (thereby preventing ongoing tissue damage by neutrophil proteases), decrease platelet aggregation (and thus further platelet recruitment), and enhance cytokine secretion (as possibly part of a feedback mechanism). It exhibits both pro and anti-inflammatory effects and is therefore suggested to play a significant role in immunomodulation. An up-regulation of ORM1 as shown by the methods of this invention (see Examples) suggests a neuroimmune response in acute ischemic stroke mediated by a balance between pro and anti-inflammatory signaling molecules. The human ORM1 mRNA sequence is publicly available as GenBank Accession No. NM_000607, the complete sequence of which is shown in FIG. 7A. The human ORM1 amino acid sequence is publicly available as GenPept Accession No. NP_000598, the complete sequence of which is shown in FIG. 7B.

(5) Arginase 1 (ARG1).

Arginase-1 (ARG1) is an enzyme induced by T-helper 2 cytokines that metabolizes L-arginine to ornithine and urea and is a critical regulator of nitric oxide (NO) synthesis. Inflammatory stimuli (T-helper 1 cytokines) result in an increased expression of inducible NO synthetase (iNOS) through L-arginine metabolism. It is possible to determine the type of inflammatory response to injury depending on the relative amount of ARG1 and iNOS since both compete for L-arginine. Trauma is associated with an increase activity of ARG1 and a decrease in the level of arginine. In addition recent studies suggest activation of the JAK and STAT pathways induces ARG1 in smooth muscle. Since humoral anti-inflammatory cytokines induce ARG1, the up-regulation of ARG1 as shown by the methods of this invention (see Examples) suggests that the response to acute ischemic stroke favors an innate humoral immune response. The human ARG1 mRNA sequence is publicly available as GenBank Accession No. NM_000045, the complete sequence of which is shown in FIG. 8A. The human ARG1 amino acid sequence is publicly available as GenPept Accession No. NP_000036, the complete sequence of which is shown in FIG. 8B.

(6) Lymphocyte Antigen 96 (LY96).

Lymphocyte antigen 96 (LY96) also known as MD2 protein, is critical for toll-like receptor 4 (TLR4) activation as an innate response to lipopolysaccharide (LPS) which is the main constituent of gram-negative bacteria. TLR4 activation induces transduction pathways resulting in NF-kappaB expression and subsequent release of pro-inflammatory cytokines (e.g. IL6 and IL8). Interestingly, natural selection has shaped the sequence patterns of TLR genes in primate evolution. However, pathogens and LPS are not the only cause of tissue damage; ischemia is another mechanism. There is accumulating evidence that ischemic tissue damage is recognized at the cell level via receptor-mediated detection of proteins (alarmins) released by dead cells. Therefore there are exogenous pathogen-associated molecular patterns (PAMPs; such as LPS) and endogenous alarmins that elicit similar responses of the innate immune system known as damage associated molecular patterns (DAMPs). The upregulation of LY96 as shown by the methods of this invention (see Examples) suggests that the response to acute ischemic stroke is mediated by the innate immune system and TLR signaling. The human LY96 mRNA sequence is publicly available as GenBank Accession No. NM_015364, the complete sequence of which is shown in FIG. 9A. The human LY96 amino acid sequence is publicly available as GenPept Accession No. NP_056179, the complete sequence of which is shown in FIG. 9B.

(7) Matrix Metalloproteinase 9 (MMP9).

Matrix Metalloproteinase 9 (MMP9) is a zinc and calcium dependent endopeptidase responsible for regulation of the extracellular matrix (ECM). Ischemia and reperfusion injury results in oxidative stress that mediates BBB disruption through metalloproteinase activation. MMP9 expression is the result of activated leukocytes (particularly neutrophils), and results in IL1beta activation and initiation of the inflammatory cascade, further contributing to BBB impairment. Up-regulation of MMP9 following acute ischemic stroke as shown by the methods of this invention (see Examples) suggests an increase in proteolytic activity early that may contribute to BBB disruption, which would allow cellular migration and signaling to and throughout the CNS. The human MMP9 mRNA sequence is publicly available as GenBank Accession No. NM_004994, the complete sequence of which is shown in FIG. 10A. The human MMP9 amino acid sequence is publicly available as GenPept Accession No. NP_004985, the complete sequence of which is shown in FIG. 10B.

(8) Carbonic Anhydrase 4 (CA4).

Carbonic anhydrase IV (CA4) is a zinc enzyme that catalyzes the conversion between carbon dioxide and the bicarbonate ion, thus making it crucial for all physiologic processes involved in cellular respiration and transport. CA4 is a membrane-bound protein found in tissues throughout the body and is found in the brain within the luminal surface of capillary endothelial cells suggesting a role for CA4 in the blood brain barrier as a regulator of CO2 and bicarbonate homeostasis in the brain. The up-regulation of CA4 as shown by the methods of this invention (see Examples) suggests there is an increase in cellular respiration following acute ischemic stroke that requires an increase in CA4 to convert $CO_2$ to $HCO_3$ to maintain pH. The human CA4 mRNA sequence is publicly available as GenBank Accession No. NM_000717, the complete sequence of which is shown in FIG. 11A. The human CA4 amino acid sequence is publicly available as GenPept Accession No. NP_000708, the complete sequence of which is shown in FIG. 11B.

(9) s100 Calcium Binding Protein A12 (s100A12).

s100 calcium binding protein A12 (s100A12) also known as calgranulin C and EN-RAGE (extracellular newly identified RAGE binding protein) is specifically related to innate immune function. S100A12 is expressed by phagocytes and released at the site of tissue inflammation. It is an endogenous DAMP that turns pro-inflammatory after a release into the extracellular space following brain injury. The Receptor for Advanced Glycation End Products (RAGE) is a member of the immunoglobulin superfamily and is a specific cell surface reaction site for advanced glycation endproducts (AGEs) which increase with advancing age. Interaction between AGEs and RAGE has been linked to chronic inflammation. Once engaged RAGE interaction in inflammatory and vascular cells results in the increased expression of MMPs. The up-regulation of s100A12 as shown by the methods of this invention (see Examples) supports the claim that the response to acute ischemic stroke is largely driven by innate immunity. The human s100A12 mRNA sequence is publicly available as GenBank Accession No. NM_005621, the complete sequence of which is shown in FIG. 12A. The human s100A12 amino acid sequence is publicly available as GenPept Accession No. NP_005612, the complete sequence of which is shown in FIG. 12B.

The biomarkers described herein, including the 9-biomarkers above, may be used individually, or as part of one or more panels as described hereinafter, and such panels may comprise 2, 3, 4, 5, 6, 7, 8, or 9 or more of individual biomarkers or related markers.

Particularly preferred markers for the diagnosis and/or prognosis of acute ischemic stroke include (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12) or markers related (i.e., related markers of these biomarkers as defined herein) thereto.

Certain preferred marker panels include at least one biomarker, and preferably 2, 3, or 4 biomarkers selected from the group consisting of (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1). In particularly preferred embodiments, one or more of these markers, and preferably 2, 3, or 4 of these biomarkers, may be combined with one or more different markers and preferably 2, 3, 4, 5, 6, 7, 8, or 9 or more different markers or related markers. In preferred embodiments, the invention provide biomarker panels that includes at least one biomarker selected from the group consisting of (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1) and any number of other biomarkers identified herein or which could be identified using the methods of the invention or other previously known biomarkers for acute ischemic stroke or other type of stroke.

The biomarker panels of the invention can include any suitable biomarker for acute ischemic stroke, or if useful, any other type of stroke or brain injury if such inclusion is deemed suitable by the user of the panel. Biomarkers for ischemic stroke previously disclosed in the art can include those described in Tang et al., "Gene expression in blood changes rapidly in neutrophils and monocytes after ischemic stroke in humans: a microarray study," Journal of Cerebral Blood Flow & Metabolism (2006) 26, pp. 1089-1102; Whiteley et al., "Blood Biomarkers in the Diagnosis of Ischemic Stroke: A Systematic Review," Stroke (2008) 39, pp. 2902-2909; Flex et al. "Proinflammatory Genetic Profiles in Subjects With History of Ischemic Stroke," Stroke (2004) 35, pp. 2270-2275; and Moore et al., "Using Peripheral Blood Mononuclear Cells to Determine a Gene Expression Profile of Acute Ischemic Stroke: A Pilot Investigation," Circulation (2005) 111, pp. 212-221, each of which are incorporated herein in their entireties by reference.

In other embodiments, the biomarker panels of the invention can comprise biomarkers that are diagnostic to different types of stroke, including acute ischemic stroke, hemorrhagic stroke, transient ischemic attacks, and subarachnoid hemorrhage and other forms of cerebral injury. Examples of other such markers can be found in the art, including, for example, in U.S. Pat. Nos. 7,608,406, 7,622,114, 6,896,872, 7,361,473, 7,358,055, and 6,897,030, each of which is incorporated herein by reference in their entireties.

In one embodiment, the present invention provides a biomarker panel for detecting or diagnosis from a test sample (e.g., peripheral blood) evidence of risk for or an occurrence of acute ischemic stroke in a patient comprising at least one, or preferably 2, 3 or 4 biomarker(s) selected from the group consisting of chemokine receptor 7 (CCR7) or chondroitin sulfate proteoglycan 2 (CSPG2) or IQ motif-containing GTPase activation protein 1 (IQGAP1) or orosomucoid 1 (ORM1).

As noted above, the amino acid and corresponding nucleic acid sequences of the biomarkers of the invention are known in the art and can be found in publicly available publications and databases. Exemplary sequences are set forth below in the form of GenBank accession numbers. The nucleic acid and polypeptide accession numbers, respectively, are set forth in parenthesis after each biomarker; (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12). One of skill in the art will understand that although accession numbers are provided, each biomarker may exist in multiple forms, each of which are encompassed by the invention. For example, variants may exist in which a small number, e.g., 1, 2, 3, 4, 5, 10 or more, nucleotides or amino acid residues are different in relation to the exemplary accession numbers set forth above. However, these variants are intended to be used in the methods of the invention. In addition, "derivatives" of the biomarkers are contemplated.

As used herein, a "derivative" of a biomarker (or of if encoding nucleic acid molecule) to a modified form of a biomarker of the invention. A modified form of a given biomarker may include at least one amino acid substitution, deletion, or insertion, wherein said modified form retains a biological activity of an unmodified form. An amino acid substitution may be considered "conservative" when the substitution results in similar structural or chemical properties (e.g., replacement of leucine with isoleucine). An amino acid substitution may be "non-conservative" in nature wherein the structure and chemical properties vary (e.g., replacement of arginine with alanine). A modified form of a given biomarker may include chemical modifications, wherein a modified form retains a biological activity of a given biomarker. Such modifications include, but are not limited to, glycosylation, phosphorylation, acetylation, alkylation, methylation, biotinylation, glutamylation glycylation, isoprenylation, lipoylation, pegylation, phosphopantetheinylation, sulfation, selenation, and C-terminal amidation. Other modifications include those involving other proteins such as ISGylation, SUMOylation, and ubiquitination. In addition, modifications may also include those involved in changing the chemical nature of an amino acid such as deimination and deamidation.

The term "biomarker panel" refers to a collection, e.g., 2 or more, 3 or more, 4 or more, 5 or more, 6 or more, 7 or more, 8 or more, 9 or more, preferably 2, 3, 4, 5, 6, 7, 8 or 9 or more biomarkers (e.g., in the form of polypeptides or nucleic acid molecules or the like), that may be analyzed, tested, assayed, probed, measured, quantified, evaluated, an the like, in a generally simultaneous manner. This includes where the individual biomarkers or means for detecting the biomarkers (e.g., oligonucleotide probe or antibody) are situated on a single surface or support medium, e.g., fixed to an array or a multi-well plate or a filament-based diagnostic system (described in further detail herein), at the time they are analyzed, tested, assayed, probed, measured, quantified, evaluated, an the like. This also includes where the biomarkers are separately analyzed, tested, assayed, probed, measured, quantified, evaluated, and the like, i.e., in separate reaction vessels or reaction environments, such that their assay results are obtained at substantially the same time. The biomarker panel can refer to the constitution of polypeptides or nucleic acid molecules in a biological sample against which are analyzed, tested, assayed, probed, measured, quantified, evaluated, and the like. Alternatively, the biomarker panel can refer a testing device on which isolated or purified biomarkers of the invention (or nucleic acid molecules encoding the biomarkers of the invention or parts thereof or antibodies specific for the biomarkers) are placed to enable the interaction of the biomarker panel with a test biological sample.

For example, a biomarker panel can include an array of antibodies specific for the biomarkers of the invention, which can be used to detect the presence of the biomarkers in a test biological sample (e.g., peripheral blood). In another embodiment, the biomarker panel can include an array of nucleic acid molecules (e.g., oligonucleotide probes) which are complimentary to mRNA encoding the biomarkers of the invention which may be present in a test sample (e.g., peripheral blood). In yet another embodiment, the biomarker panel can include purified biomarker polypeptides of the invention for the screening of compounds or agents in a test sample or agent library that may interact or bind to the biomarker polypeptides of the invention.

It will be appreciated that the biomarker panels preferably include at least one biomarker for diagnosis or predicting acute ischemic stroke, including (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12) or markers related (i.e., related markers of these biomarkers as defined herein) thereto. Preferably, the biomarker panels include at least one of (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1). As noted, the biomarker panels of the invention can be comprised of the biomarker polypeptides themselves, antibodies that are specific to the biomarker polypeptides or even nucleic acid molecules that are complimentary or that recognize corresponding nucleic acid molecules in a sample which encode a biomarker of the invention.

In addition, the biomarker panels of the invention can include other biomarkers that pertain to other diseases or conditions other than acute ischemic stroke, including any other type of stroke, or other non-stroke condition, in the event a user wishes to test or detect not only acute ischemic strokes, but also other conditions at the same time or using the same panel or set of biomarkers. Examples of other such biomarkers include those related to blood pressure (e.g., A-type natriuretic peptide, C-type antriuretic peptide, urotensin II, vasopressen, calcitonin, angiotensin II, adrenomedullin, and endothenlins), coagulation and hemostasis (D-dimer, plasmin, b-thromboglobulin, platelet factor 4, fibrinopeptide A, platelet-derived growth factor, prothrombin, P-selectin and thrombin), acute phase response (C-reactive protein, mannose-binding protein, human neutrophil elastase, inducible nitric oxide synthase, lysophosphatidic acid, malondialdehyde LDL, lipopolysaccharide binding protein) and markers related to inflammation (interleukins, tumor necrosis factor, myeloperoxidase, soluble intercellular adhesion molecule, vascular cell adhesion molecule, monocyte chemotactic protein-1). Such other biomarkers may assist in gaining a better overall clinical picture of the health of the patient and the potential causes of stroke. Such markers can be selected on the basis of the knowledge of one or ordinary skill in the art. Additional examples of such markers can be found in the art, for example, in U.S. Pat. No. 7,608,406, which is incorporated herein by reference.

Biomarker Forms

One of ordinary skill in the art will appreciate that proteins frequently exist in a biological sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., cleavage of a signal sequence or fragments of a parent protein), glycosylation, phosphorylation, lipidation, oxidation, methylation, cysteinylation, sulphonation and acetylation.

When detecting or measuring a biomarker of the invention in a sample, the ability to differentiate between different forms of a protein biomarker depends upon the nature of the difference and the method used to detect or measure. For example, an immunoassay using a monoclonal antibody will detect all forms of a protein containing the epitope and will not distinguish between them. However, a sandwich immunoassay that uses two antibodies directed against different epitopes on a protein will detect all forms of the protein that contain both epitopes and will not detect those forms that contain only one of the epitopes.

In diagnostic assays, the inability to distinguish different forms of a biomarker protein has little impact when the forms detected by the particular method used are equally good biomarkers as any other particular form. However, when a particular form (or a subset of particular forms) of a protein is a better biomarker than the collection of different forms detected together by a particular method, the power of the assay may suffer. In this case, it may be useful to employ an assay method that distinguishes between forms of a protein and that specifically detects and measures a desired form or forms of the protein. Distinguishing different forms of an analyte (e.g., a biomarker) or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biospecific capture reagent (e.g., an antibody that recognizes the biomarker and other forms of it) is used to capture the biomarker of interest. Preferably, the biospecific capture reagent is bound to a solid phase, such as a bead, a plate, a membrane or an array. After unbound materials are washed away, the captured analytes are detected and/or measured by mass spectrometry. (This method also will also result in the capture of protein intereactors that are bound to the proteins or that are otherwise recognized by antibodies and that, themselves, can be biomarkers.) Various forms of mass spectrometry are useful for detecting the protein forms, including laser desorption approaches, such as traditional MALDI or SELDI, and electrospray ionization.

Detection Methods

Numerous methods and devices are well known to the skilled artisan for the detection and analysis of the biomarkers of the instant invention.

With regard to polypeptides or proteins in patient test samples, immunoassay devices and methods can be used. See, e.g., U.S. Pat. Nos. 6,143,576; 6,113,855; 6,019,944;

5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest.

Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing the immunoassays taught herein.

Preferably the biomarkers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material or membrane (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of biomarkers may be carried out separately or simultaneously with one test sample. For separate or sequential assay of markers, suitable apparatuses include clinical laboratory analyzers such as the ELECSYS® (Roche), the AXSYM® (Abbott), the ACCESS® (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of markers on a single surface. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and certain capillary devices (see e.g., U.S. Pat. No. 6,019,944). In these embodiments each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection. As noted, many protein biochips are described in the art. These further include, for example, protein biochips produced by Ciphergen Biosystems, Inc. (Fremont, Calif.), Packard BioScience Company (Meriden Conn.), Zyomyx (Hayward, Calif.), Phylos (Lexington, Mass.) and Biacore (Uppsala, Sweden). Examples of such protein bio chips are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828, each of which are incorporated by reference.

Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies as indicated by reperfusion or resolution of symptoms, differentiation of the various types of stroke, identification of the severity of the event, identification of the disease severity, and identification of the patient's outcome, including risk of future events.

As noted, a biomarker panel consisting of the biomarkers referenced above may be constructed to provide relevant information related to diagnosis of acute ischemic stroke. Such a panel may be constructed using 1, 2, 3, 4, 5, 6, 7, 8, 9, 10, 15, 20, or more or individual markers, but preferably includes at least one of (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12) or related markers, and more preferably at least one of (1) chemokine receptor 7 (CCR7); (2) chondroitin sulfate proteoglycan 2 (CSPG2); (3) IQ motif-containing GTPase activation protein 1 (IQGAP1); or (4) orosomucoid 1 (ORM1) or related markers.

The analysis of a single marker or subsets of markers comprising a larger panel of markers could be carried out by one skilled in the art to optimize clinical sensitivity or specificity in various clinical settings. These include, but are not limited to ambulatory, urgent care, emergency care, critical care, intensive care, monitoring unit, inpatient, outpatient, physician office, medical clinic, and health screening settings. Furthermore, one skilled in the art can use a single marker or a subset of markers comprising a larger panel of markers in combination with an adjustment of the diagnostic threshold in each of the aforementioned settings to optimize clinical sensitivity and specificity.

In addition, the analysis of the biomarkers of the invention can be carried out by a person of skill who may not necessarily have an expertise with stroke-specific medicine and care, e.g., emergency room or urgent care clinicians, ambulatory clinicians, or any physician not having an expertise in stroke-specific medicine.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings.

The present invention also contemplates the use of filament-based detection systems for rapidly detecting the biomarkers of the invention. Filament-based detection systems are known in the art and can be found, for example, in US Published Application No. 2006/012148 A1, and which are described in further detail below.

Diagnosis Methods

The invention provides methods and systems for the identification of one or more biomarkers for the diagnosis of disease, including preferably acute ischemic stroke. One skilled in the art will also recognize that analysis of markers can be performed and the data from the analyses of multiple markers can be combined to form panels of markers to increase the sensitivity and reliability of a diagnosis.

In developing a panel of markers useful in diagnosis of a particular disease or condition, e.g., acute ischemic stroke, data for a number of potential markers may be obtained from a group of subjects by testing for the presence or level of certain markers. The group of subjects can be divided into two sets, and preferably the first set and the second set each have an approximately equal number of subjects. The first set includes subjects who have been confirmed as having a disease or, more generally, being in a first condition state (e.g., acute ischemic stroke). For example, this first set of patients may be those that have recently had an acute ischemic stroke, or may be those having a specific type of stroke (e.g., thrombotic, embolic, lacunar, hypoperfusion, intracerebral hemorrhage, and subarachnoid hemorrhage types of strokes). The confirmation of this condition state may be made through a more rigorous and/or expensive testing such as MRI or CT or other instrumentation-based confirmatory test. Hereinafter, subjects in this first set will be referred to as "diseased".

The second set of subjects are simply those who do not fall within the first set. Subjects in this second set may be "non-diseased;" that is, normal subjects. Alternatively, subjects in this second set may be selected to exhibit one symptom or a constellation of symptoms that mimic those symptoms exhibited by the "diseased" subjects. In the case of neurological disorders, for example, the skilled artisan will understand that neurologic dysfunction is a common symptom in various systemic disorders (e.g., alcoholism, vascular disease, stroke, a specific type of stroke (e.g., thrombotic, embolic, lacunar, hypoperfusion, intracerebral hemorrhage, and subarachnoid hemorrhage types of strokes) autoimmunity, metabolic disorders, aging, etc.).

Specific neurologic dysfunctions or "stroke-associated symptoms" or "stroke-mimicking symptoms" may include, but are not limited to, pain, headache, aphasia, apraxia, agnosia, amnesia, stupor, confusion, vertigo, coma, delirium, dementia, seizure, migraine insomnia, hypersomnia, sleep apnea, tremor, dyskinesia, paralysis, visual disturbances, diplopia, paresthesias, dysarthria, hemiplegia, hemianesthesia, hemianopia, etc. Patients exhibiting one or more of these symptoms but that have not suffered from a stroke are referred to herein as "stroke mimics." Conditions within the differential diagnosis of stroke include brain tumor (including primary and metastatic disease), aneurysm, electrocution, burns, infections (e.g., meningitis), cerebral hypoxia, head injury (including concussion), stress, dehydration, nerve palsy (cranial or peripheral), hypoglycemia, migraine, multiple sclerosis, peripheral vascular disease, peripheral neuropathy, seizure (including grand mal seizure), subdural hematoma, syncope, and transient unilateral weakness. Preferred markers and marker panels are those that can distinguish acute ischemic stroke from these stroke mimicking conditions.

The data obtained from subjects in these sets includes levels of a plurality of markers. Preferably, data for the same set of markers is available for each patient. This set of markers may include all candidate markers which may be suspected as being relevant to the detection of a particular disease or condition, e.g., those identified 9-biomarkers of the invention. Embodiments of the methods and systems described herein may be used to determine which of the candidate markers are most relevant to the diagnosis of the disease or condition. The levels of each marker in the two sets of subjects may be distributed across a broad range, e.g., as a Gaussian distribution. However, no distribution fit is required.

As noted above, a marker often is incapable of definitively identifying a patient as either diseased or non-diseased. For example, if a patient is measured as having a marker level that falls within the overlapping region, the results of the test may not be helpful in diagnosing the patient. An artificial cutoff may be used to distinguish between a positive and a negative test result for the detection of the disease or condition. Regardless of where the cutoff is selected, the effectiveness of the single marker as a diagnosis tool is unaffected. Changing the cutoff merely trades off between the number of false positives and the number of false negatives resulting from the use of the single marker. The effectiveness of a test having such an overlap is often expressed using a ROC (Receiver Operating Characteristic) curve. ROC curves are well known to those skilled in the art.

The horizontal axis of the ROC curve represents (1-specificity), which increases with the rate of false positives. The vertical axis of the curve represents sensitivity, which increases with the rate of true positives. Thus, for a particular cutoff selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

As discussed above, the measurement of the level of a single marker may have limited usefulness. The measurement of additional markers provides additional information, but the difficulty lies in properly combining the levels of two potentially unrelated measurements. In the methods and systems according to embodiments of the present invention, data relating to levels of various markers for the sets of diseased and non-diseased patients may be used to develop a panel of markers to provide a useful panel response. The data may be provided in a database such as Microsoft Access, Oracle, other SQL databases or simply in a data file. The database or data file may contain, for example, a patient identifier such as a name or number, the levels of the various markers present, and whether the patient is diseased or non-diseased.

Next, an artificial cutoff region may be initially selected for each marker. The location of the cutoff region may initially be selected at any point, but the selection may affect the optimization process described below. In this regard, selection near a suspected optimal location may facilitate faster convergence of the optimizer. In a preferred method, the cutoff region is initially centered about the center of the overlap region of the two sets of patients. In one embodiment, the cutoff region may simply be a cutoff point. In other embodiments, the cutoff region may have a length of greater than zero. In this regard, the cutoff region may be defined by a center value and a magnitude of length. In practice, the initial selection of the limits of the cutoff region may be determined according to a pre-selected percentile of each set of subjects. For example, a point above which a pre-selected percentile of diseased patients are measured may be used as the right (upper) end of the cutoff range.

Each marker value for each patient may then be mapped to an indicator. The indicator is assigned one value below the cutoff region and another value above the cutoff region. For example, if a marker generally has a lower value for non-diseased patients and a higher value for diseased patients, a zero indicator will be assigned to a low value for a particular marker, indicating a potentially low likelihood of a positive diagnosis. In other embodiments, the indicator may be calculated based on a polynomial. The coefficients of the polynomial may be determined based on the distributions of the marker values among the diseased and non-diseased subjects.

The relative importance of the various markers may be indicated by a weighting factor. The weighting factor may initially be assigned as a coefficient for each marker. As with the cutoff region, the initial selection of the weighting factor may be selected at any acceptable value, but the selection may affect the optimization process. In this regard, selection near a suspected optimal location may facilitate faster convergence of the optimizer. In a preferred method, acceptable weighting coefficients may range between zero and one, and an initial weighting coefficient for each marker may be assigned as 0.5. In a preferred embodiment, the initial weighting coefficient for each marker may be associated with the effectiveness of that marker by itself. For example, a ROC curve may be generated for the single marker, and the area under the ROC curve may be used as the initial weighting coefficient for that marker.

Next, a panel response may be calculated for each subject in each of the two sets. The panel response is a function of the indicators to which each marker level is mapped and the weighting coefficients for each marker. One advantage of using an indicator value rather than the marker value is that an extraordinarily high or low marker levels do not change the probability of a diagnosis of diseased or non-diseased for that particular marker. Typically, a marker value above a certain level generally indicates a certain condition state. Marker values above that level indicate the condition state with the same certainty. Thus, an extraordinarily high marker value may not indicate an extraordinarily high probability of that condition state. The use of an indicator which is constant on one side of the cutoff region eliminates this concern.

The panel response may also be a general function of several parameters including the marker levels and other factors including, for example, race and gender of the patient. Other factors contributing to the panel response may include the slope of the value of a particular marker over time. For example, a patient may be measured when first arriving at the hospital for a particular marker. The same marker may be measured again an hour later or some other time increment later, and the level of change may be reflected in the panel response. Further, additional markers may be derived from other markers and may contribute to the value of the panel response. For example, the ratio of values of two markers may be a factor in calculating the panel response.

Having obtained panel responses for each subject in each set of subjects, the distribution of the panel responses for each set may now be analyzed. An objective function may be defined to facilitate the selection of an effective panel. The objective function should generally be indicative of the effectiveness of the panel, as may be expressed by, for example, overlap of the panel responses of the diseased set of subjects and the panel responses of the non-diseased set of subjects. In this manner, the objective function may be optimized to maximize the effectiveness of the panel by, for example, minimizing the overlap.

In a preferred embodiment, the ROC curve representing the panel responses of the two sets of subjects may be used to define the objective function. For example, the objective function may reflect the area under the ROC curve. By maximizing the area under the curve, one may maximize the effectiveness of the panel of markers. In other embodiments, other features of the ROC curve may be used to define the objective function. For example, the point at which the slope of the ROC curve is equal to one may be a useful feature. In other embodiments, the point at which the product of sensitivity and specificity is a maximum, sometimes referred to as the "knee," may be used. In an embodiment, the sensitivity at the knee may be maximized. In further embodiments, the sensitivity at a predetermined specificity level may be used to define the objective function. Other embodiments may use the specificity at a predetermined sensitivity level may be used. In still other embodiments, combinations of two or more of these ROC-curve features may be used.

It is possible that one of the markers in the panel is specific to the disease or condition being diagnosed. When such markers are present at above or below a certain threshold, the panel response may be set to return a "positive" test result. When the threshold is not satisfied, however, the levels of the marker may nevertheless be used as possible contributors to the objective function.

An optimization algorithm may be used to maximize or minimize the objective function. Optimization algorithms are well-known to those skilled in the art and include several commonly available minimizing or maximizing functions including the Simplex method and other constrained optimization techniques. It is understood by those skilled in the art that some minimization functions are better than others at searching for global minimums, rather than local minimums. In the optimization process, the location and size of the cutoff region for each marker may be allowed to vary to provide at least two degrees of freedom per marker. Such variable parameters are referred to herein as independent variables. In a preferred embodiment, the weighting coefficient for each marker is also allowed to vary across iterations of the optimization algorithm. In various embodiments, any permutation of these parameters may be used as independent variables.

In addition to the above-described parameters, the sense of each marker may also be used as an independent variable. For example, in many cases, it may not be known whether a higher level for a certain marker is generally indicative of a diseased state or a non-diseased state. In such a case, it may be useful to allow the optimization process to search on both sides. In practice, this may be implemented in several ways. For example, in one embodiment, the sense may be a truly separate independent variable which may be flipped between positive and negative by the optimization process. Alternatively, the sense may be implemented by allowing the weighting coefficient to be negative.

The optimization algorithm may be provided with certain constraints as well. For example, the resulting ROC curve may be constrained to provide an area-under-curve of greater than a particular value. ROC curves having an area under the curve of 0.5 indicate complete randomness, while an area under the curve of 1.0 reflects perfect separation of the two sets. Thus, a minimum acceptable value, such as 0.75, may be used as a constraint, particularly if the objective function does not incorporate the area under the curve. Other constraints may include limitations on the weighting coefficients of particular markers. Additional constraints may limit the sum of all the weighting coefficients to a particular value, such as 1.0.

The iterations of the optimization algorithm generally vary the independent parameters to satisfy the constraints while minimizing or maximizing the objective function. The number of iterations may be limited in the optimization process. Further, the optimization process may be terminated when the difference in the objective function between two consecutive iterations is below a predetermined threshold, thereby indicating that the optimization algorithm has reached a region of a local minimum or a maximum.

Thus, the optimization process may provide a panel of markers including weighting coefficients for each marker and cutoff regions for the mapping of marker values to indicators. In order to develop lower-cost panels which require the measurement of fewer marker levels, certain markers may be eliminated from the panel. In this regard, the effective contribution of each marker in the panel may be determined to identify the relative importance of the markers. In one embodiment, the weighting coefficients resulting from the optimization process may be used to determine the relative importance of each marker. The markers with the lowest coefficients may be eliminated.

In certain cases, the lower weighting coefficients may not be indicative of a low importance. Similarly, a higher weighting coefficient may not be indicative of a high importance. For example, the optimization process may result in a high coefficient if the associated marker is irrelevant to the diagnosis. In this instance, there may not be any advantage that will drive the coefficient lower. Varying this coefficient may not affect the value of the objective function.

Individual panel response values may also be used as markers in the methods described herein. For example, a panel may be constructed from a plurality of markers, and each marker of the panel may be described by a function and a weighting factor to be applied to that marker (as determined by the methods described above). Each individual marker level is determined for a sample to be tested, and that level is applied to the predetermined function and weighting factor for that particular marker to arrive at a sample value for that marker. The sample values for each marker are added together to arrive at the panel response for that particular sample to be tested. For a "diseased" and "non-diseased" group of patients, the resulting panel responses may be treated as if they were just levels of another disease marker.

One could use such a method to define new biomarkers. For example, one may divide stroke subjects and non-stroke subjects as follows: (1) ischemic stroke; (2) hemorrhagic stroke; (3) normals; (4) TIAs; (5) other stroke mimics. One would define a first panel constructed from a plurality of markers as described above, and obtain the panel responses from this first panel for all the subjects. Then, the members of any one of these 5 groups may be compared to the panel responses of the members of any other of these groups to define a function and weighting factor that best differentiates these two groups based on the panel responses. This can be repeated as all 5 groups are compared pairwise. The "markers" used to define a second panel might include any or all of the following as a new "marker": ischemic stroke versus normals as marker 1; hemorrhagic stroke versus normals as marker 2; ischemic stroke versus TIAs as marker 3; hemorrhagic stroke versus TIAs as marker 4; ischemic stroke versus other mimics as marker 5; and hemorrhagic stroke versus other mimics as marker 6.

Measures of test accuracy may be obtained as described in Fischer et al., Intensive Care Med. 29: 1043-51, 2003, and used to determine the effectiveness of a given marker or panel of markers. These measures include sensitivity and specificity, predictive values, likelihood ratios, diagnostic odds ratios, and ROC curve areas. As discussed above, suitable tests may exhibit one or more of the following results on these various measures: at least 75% sensitivity, combined with at least 75% specificity; ROC curve area of at least 0.7, more preferably at least 0.8, even more preferably at least 0.9, and most preferably at least 0.95; and/or a positive likelihood ratio (calculated as sensitivity/(1-specificity)) of at least 5, more preferably at least 10, and most preferably at least 20, and a negative likelihood ratio (calculated as (1-sensitivity)/specificity) of less than or equal to 0.3, more preferably less than or equal to 0.2, and most preferably less than or equal to 0.1.

As noted, a number of immunoassays or nucleic acid based tests can be used to rapidly detect the presence of the biomarkers of the invention in a biological sample, in particular, when done in the context of the urgent clinical setting. Examples include radioimmunoassays, enzyme immunoassays (e.g. ELISA), immunofluorescence, immunoprecipitation, latex agglutination, hemagglutination, and histochemical tests. A particularly preferred method, however, because of its speed and ease of use, is latex agglutination.

Latex agglutination assays have been described in Beltz, G. A. et al., in Molecular Probes: Techniques and Medical Applications, A. Albertini et al., eds., Raven Press, New York, 1989, incorporated herein by reference. In the latex agglutination assay, antibody raised against a particular biomarker is immobilized on latex particles. A drop of the latex particles is added to an appropriate dilution of the serum to be tested and mixed by gentle rocking of the card. With samples lacking sufficient levels of the biomarkers, the latex particles remain in suspension and retain a smooth, milky appearance. However, if biomarkers reactive with the antibody are present, the latex particles clump into visibly detectable aggregates.

An agglutination assay can also be used to detect biomarkers wherein the corresponding antibody is immobilized on a suitable particle other than latex beads, for example, on gelatin, red blood cells, nylon, liposomes, gold particles, etc. The presence of antibodies in the assay causes agglutination, similar to that of a precipitation reaction, which can then be detected by such techniques as nephelometry, turbidity, infrared spectrometry, visual inspection, colorimetry, and the like.

The term latex agglutination is employed generically herein to refer to any method based upon the formation of detectable agglutination, and is not limited to the use of latex as the immunosorbent substrate. While preferred substrates for the agglutination are latex based, such as polystyrene and polypropylene, particularly polystyrene, other well-known substrates include beads formed from glass, paper, dextran, and nylon. The immobilized antibodies may be covalently, ionically, or physically bound to the solid-phase immunoadsorbent, by techniques such as covalent bonding via an amide or ester linkage, ionic attraction, or by adsorption. Those skilled in the art will know many other suitable carriers for binding antibodies, or will be able to ascertain such, using routine experimentation.

Conventional methods can be used to prepare the antibodies. For example, by using a peptide of a biomarker of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be administered and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for the biomarkers of the invention as described herein.

In addition, the biomarkers of the invention may be measured by detection and quantification of nucleic acids encoding the biomarkers, e.g., cDNAs corresponding to mRNAs present in the peripheral blood. Such detection methods may be carried out by any suitable means for analyzing nucleic acids, including traditional PCR assays such as cDNA hybridization, Northern blots, or Southern blots. These methods can be carried out using oligonucleotides that hybridize to nucleic acid molecules encoding the polypeptide biomarkers of the invention. One of ordinary skill in the art is fully capable of designing and selecting appropriate oligonucleotide molecules based on the known sequences of the biomarkers as noted above.

Compositions of Matter

In another aspect, this invention provides compositions of matter based on the biomarkers of the present invention.

In one embodiment, this invention provides biomarkers of this invention in purified form. Purified biomarkers have utility as antigens to raise antibodies. Purified biomarkers also have utility as standards in assay procedures. As used herein, a "purified biomarker" is a biomarker that has been isolated from other proteins and peptides, and/or other material from the biological sample in which the biomarker is found. Biomarkers may be purified using any method known in the art, including, but not limited to, mechanical separation (e.g., centrifugation), ammonium sulphate precipitation, dialysis (including size-exclusion dialysis), size-exclusion chromatography, affinity chromatography, anion-exchange chromatography, cation-exchange chromatography, and metal-chelate chromatography. Such methods may be performed at any appropriate scale, for example, in a chromatography column, or on a biochip.

Thus, in one embodiment, the present invention provides purified biomarkers of the invention, including (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12).

In another embodiment, this invention provides biospecific capture reagents that specifically bind a biomarker of this invention, optionally in purified form. Preferably, a biospecific capture reagent is an antibody. In one embodiment, a biospecific capture reagent is an antibody that binds (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); or (9) s100 calcium binding protein A12 (s100A12).

In another embodiment, this invention provides a complex between a biomarker of this invention and biospecific capture reagent that specifically binds the biomarker. In other embodiments, the biospecific capture reagent is bound to a solid phase. For example, this invention contemplates a device comprising bead or chip derivatized with a biospecific capture reagent that binds to a biomarker of this invention and, also, the device in which a biomarker of this invention is bound to the biospecific capture reagent.

In another embodiment, this invention provides a device comprising a solid substrate to which is attached an adsorbent, e.g., a chromatographic adsorbent, to which is further bound a biomarker of this invention.

Kits and Detection Systems (e.g., Filament-Based Detection Systems)

In another embodiment the invention provides kits for diagnosing acute ischemic stroke in a patient. Depending on how the kit is to be operated, the kit may include one or more biomarker polypeptides of the invention, including preferably (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); or (9) s100 calcium binding protein A12 (s100A12). In addition, the kit may include antibodies that specifically bind to any of the biomarker polypeptides of the invention. If the kit is to be used to detect nucleic acid molecules that correspond to the biomarkers of the invention, the kit may include oligonucleotide molecules or other nucleic acid molecules for use in the detection of the biomarker DNA or RNA in a sample. Both antibody and antigen preparations should preferably be provided in a suitable titrated form, with antigen concentrations and/or antibody titers given for easy reference in quantitative applications.

In certain embodiments, the kits may also include an immunodetection reagent or label for the detection of specific immunoreaction between the provided biomarkers and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present invention are generally well known in the art.

The reagents may also include ancillary agents such as buffering agents and protein stabilizing agents, e.g., polysaccharides and the like. The diagnostic kit may further include where necessary agents for reducing background interference in a test, agents for increasing signal, apparatus for conducting a test, calibration curves and charts, standardization curves and charts, and the like.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

In a more particular aspect, the kit of the invention relates to a rapid biomarker panel for detecting acute ischemic stroke in a patient comprising antibodies to one or more biomarkers of the invention, including preferably (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); or (9) s100 calcium binding protein A12 (s100A12), and including more preferably (1) chemokine receptor 7 (CCR7); (2) chondroitin sulfate proteoglycan 2 (CSPG2); (3) IQ motif-containing GTPase activation protein 1 (IQGAP1); or (4) orosomucoid 1 (ORM1). Such kits may include other components, as needed and as described above.

In another particular aspect, the kit of the invention relates to a rapid biomarker panel for detecting acute ischemic stroke in a patient comprising one or more biomarkers of the invention, including preferably (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); or (9) s100 calcium binding protein A12 (s100A12), and including more preferably (1) chemokine receptor 7 (CCR7); (2) chondroitin sulfate proteoglycan 2 (CSPG2); (3) IQ motif-containing GTPase activation protein 1 (IQGAP1); or (4) orosomucoid 1 (ORM1). Such kits may include other components, as needed and as described above.

In yet another particular aspect the invention relates to a rapid biomarker panel for detecting acute ischemic stroke in a patient comprising a nucleic acid molecule (e.g., an oligonucleotide) that hybridizes with a nucleic acid molecule encoding one or more biomarkers of the invention (e.g., the mRNA corresponding to or encoding the biomarkers of the invention), including preferably (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); or (9) s100 calcium binding protein A12 (s100A12), and including more preferably (1) chemokine receptor 7 (CCR7); (2) chondroitin sulfate proteoglycan 2 (CSPG2); (3) IQ motif-containing GTPase activation protein 1 (IQGAP1); or (4) orosomucoid 1 (ORM1). Such kits may include other components, as needed and as described above.

In a particular embodiment, the present invention contemplates a filament-based rapid diagnostic kit or test system that can be used as a "point-of-care" (POC) diagnostic system for rapid diagnosis of acute ischemic stroke or risk thereof utilizing the biomarkers of the invention, including, the nine gene panel of the invention (or some subgroup thereof, e.g., at least 2 biomarkers, or 3, or 4, or 5, or 6, or 7, or 8 of the biomarkers of the group including (1) chemokine receptor 7 (CCR7); (2) chondroitin sulfate proteoglycan 2 (CSPG2); (3) IQ motif-containing GTPase activation protein 1 (IQGAP1); (4) orosomucoid 1 (ORM1); (5) arginase 1 (ARG1); (6) lymphocyte antigen 96 (LY96); (7) matrix metalloproteinase 9 (MMP9); (8) carbonic anhydrase 4 (CA4); and (9) s100 calcium binding protein A12 (s100A12)), to rapidly and easily detect or diagnose acute ischemic stroke and/or to distinguish from diagnoses other forms of stroke, TIAs and stroke mimic events. Such a POC test advantageously be operated by anyone irrespective of a person's level of expertise in clinical stroke care and/or testing.

As used herein, a "filament-based test or diagnostic system" takes the meaning as contemplated in the art, and in particular, in U.S. Published Application No. US 2006/012148 A1, which is incorporated herein by reference in its entirety. In general, filament-based tests utilize either capture antibodies on a polyester filament, or DNA (or other nucleic acid) probe on a gold wire, each of which function as molecular hooks to troll for polypeptides or nucleic acid molecules of interest (e.g., the biomarker polypeptides of the invention, or their corresponding mRNA molecules) in a biological sample, e.g., peripheral blood. For antibody detection of "target" polypeptides (e.g., the biomarker polypeptides of the invention), a filament material immobilized with antibodies specific for the target polypeptides that has been exposed to a test sample (e.g., peripheral blood) is threaded through an array of chambers that carry out the washing and ultimate reporting of the result. For nucleic acid detection (e.g., mRNA encoding the biomarkers of the invention), a filament containing DNA or nucleotide probes bound to the filament (e.g., gold filament) that are specific or hybridize to target nucleic acid molecules in the a biological sample (e.g., mRNA of each biomarker in a sample of peripheral blood), that is passed through various chambers that carry out the washing and reporting of any probe/target interactions that have occurred on the filament surface.

In one aspect, the filament-based system includes a filament support which provides the opportunity to rapidly and efficiently move probes between different zones (e.g., chambers, such as the washing chamber or a reporting chamber) of an apparatus and still retain information about their location. It also permits the use of very small volumes of various samples—as little as nanoliter volume reactions. The filament may be constructed so that the probes are arranged in an annular fashion, forming a probe band around the circumference of the filament. This also permits bands to be deposited so as to achieve high linear density of probes on the filament.

The filament may be made of any of a number of different materials. Suitable materials include polystyerene, glass (e.g., fiber optic cores), nylon or other substrate derivatized with chemical moieties to impart desired surface structure (3-dimensional) and chemical activity. The filament may also be constructed to contain surface features such as pores, abrasians, invaginations, protrusions, or any other physical or chemical structures that increase effective surface area. These surface features may, in one aspect, provide for enhanced mixing of solutions as the filament passes through a solution-containing chamber, or increase the number and availability of probe molecules. The filament may also contain a probe identifier which allows the user to track large numbers of different probes on a single filament. The probe identifiers may be dyes, magnetic, radioactive, fluorescent, or chemilluminescent molecules. Alternatively, they may comprise various digital or analog tags.

The probes that are attached to the filaments can be any of a variety of biomolecules, including, in particular with respect to this invention, nucleic acid molecules (e.g., oligonucleotides) and antibodies or antibodies fragments. The probes should be capable of binding to or interacting with a target substance of interest (e.g., the polypeptide biomarkers of the invention or their encoding mRNA molecules) in a sample to be tested (e.g., peripheral blood), such that the binding to or interaction is capable of being detected.

The term "nucleic acid" is well known in the art. A "nucleic acid" as used herein will generally refer to a molecule of DNA, RNA or a derivative or analog thereof, including synthetic molecules. Nucleic acids are also defined as molecules containing a series of naturally-occurring purine or pyrimidine bases. The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to both single-stranded and double-stranded molecules, the latter being substantially or fully complementary to each other. A nucleic acid may even encompass a triple-stranded molecule. As used herein, a single stranded nucleic acid may be denoted by the prefix "ss," a double stranded nucleic acid by the prefix "ds," and a triple stranded nucleic acid by the prefix "ts."

The probes can also be proteinaceous materials, e.g., polypeptides or polypeptide fragments of the biomarkers of the invention. In another embodiment, the probe may be a proteinaceous compound. There are wide variety of protein-protein interactions; however, proteins also bind nucleic acids, metals and other non-proteinaceous compounds (e.g., lipids, hormones, transmitters). Some other examples of protein that may be used as either targets or probes include, but are not limited to, antibodies, enzymes, receptors, and DNA- or RNA-binding proteins.

In various embodiments, it may desirable to label probe or target molecules. Examples of labels include paramagnetic ions, radioactive isotopes; fluorochromes, NMR-detectable substances, and X-ray imaging compounds.

Paramagnetic ions include chromium (III), manganese (II), iron (III), iron (II), cobalt (II), nickel (II), copper (II), neodymium (II), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

Radioactive isotopes include $^{14}$-carbon, $^{15}$chromium, $^{36}$-chlorine, $^{57}$cobalt, and the like may be utilized. Among the fluorescent labels contemplated for use include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red. Enzymes (an enzyme tag) that will generate a colored product upon contact with a chromogenic substrate may also be used. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

The chambers of the filament-based system can be of any suitable design or function, including processing chambers, pretreatment chambers, wash chambers and amplification chambers.

A variety of different types of chambers may be used in accordance with the present invention. The invention contemplates a processing chamber containing putative target molecules for binding. It also is possible, where convenient, to have a series of processing chambers that are connected by means other than the filament. For example, one may wish to "recycle" target solution by moving it from one chamber to another for reuse. A processing chamber may also be reused in the sense that the filament may be passed through a given chamber more than once.

The present invention may utilize multiple processing in such chambers where different target solutions included therein. Thus, a single filament can be utilized for multiple reactions in a single "run." If a large number of reactions are to be run, a series of processing chambers may be utilized that can quickly be emptied, rinsed, and filled with new target solutions. Thus, one can image an apparatus with three processing chambers A, B and C, where after a filament passes through each chamber, the chambers can be emptied and refilled with new target solutions, and the movement of the filament is reversed. By repeating this process two more times, a series of four filament passes permit exposure to twelve different target solutions.

The probes or filaments can also be "pretreated" in such a way as to ensure that the ensuing reaction with the target has a high degree of fidelity, i.e., minimize non-specific attachment. A classic example is of a pretreatment is a "blocking" reaction. Non-specific protein-protein interactions by inhibited by pretreating a substrate with a non-specific protein such as BSA. Similarly, non-specific DNA reactions can be reduced by incubating the probe with a "random" DNA known to lack homology with the probe.

The filament-based system also contemplates washing chambers to remove non-specifically bound molecules from the probe. Though achieving the same goal as pretreatment, washing takes place after the exposure of probe to target. Typically, wash solutions comprise a buffer similar to that used in the target solution, but lacking the target itself Occasionally, it will be desirable to alter the chemical properties of the wash solution by, for example, changing the salt concentration or pH.

The system can also include a signal-amplification chamber capable of recursively amplifying signals relating to binding of targets to probe. There are a variety of mechanisms for accomplishing this. However, a common feature will be the need for one or more chambers which effect the necessary steps to achieve the amplification.

The above disclosure generally describes the present invention. A more complete understanding can be obtained by reference to the following specific examples, which are provided for purposes of illustration only and are not intended to limit the scope of the invention.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Example 1

Identification of Blood Biomarkers for Acute Ischemic Stroke

Overview.

The objective of this study was to identify peripheral blood biomarkers for the differential diagnosis of acute ischemic cerebrovascular syndrome (AICS) through gene expression profiling. Peripheral whole blood samples were collected from n=39 patients who were ≥18 years of age with MRI diagnosed AICS and n=25 control subjects who were Non-stroke neurologically healthy. Total RNA was extracted from whole blood stabilized in Paxgene RNA tubes, amplified, and hybridized to Illumina humanRef-8v2 bead chips. Gene expression was compared in a univariate manner between stroke patients and control subjects using t-test in GeneSpring. The significant genes were tested in a logistic regression model controlling for age, hypertension and dyslipidemia. Inflation of type one error was corrected by Bonferroni and False Discovery Rate. Validation was performed by QRT-PCR using Taqman gene expression assays. A nine gene profile has been identified in the whole blood of AICS patients using gene expression profiling. Five of these nine genes were identified in a previously published expression profiling study of stroke and are therefore likely candidates for AICS diagnosis. Pathway analysis revealed toll like receptor (TLR) signaling as a highly significant canonical pathway present in the peripheral whole blood of AICS patients. This study replicates the findings of a previous expression profiling study of ischemic stroke and therefore supports the claim that gene expression profiling of peripheral whole blood can be used to identify biomarkers of AICS.

Introduction.

Stroke is the third leading cause of death in the United States (1) and one of the most common causes of death and disability in industrialized countries (2). Despite significant advances in neuroimaging and acute clinical management that have resulted in greater numbers of patients surviving the initial insult (3), the rate of false-positive diagnoses of ischemic stroke can be as high as 25% (4). The small percentage of patients who actually receive rtPA (3-5%) and the large numbers of patients who leave the hospital with either a diagnosis of transient ischemic attack (TIA) or stroke of undetermined cause reflects the need to identify additional definitive means of stroke diagnosis.

A novel approach to the study of ischemic stroke is the use of gene expression profiling to discover biomarkers that improve acute stroke diagnosis and classification, identify secondary complications such as blood brain barrier disruption or aid in the development of novel stroke therapeutics. A secondary advantage of gene expression profiling is its ability to unveil the molecular pathways involved in brain recovery and health and elucidate complex genomic interactions that may play a role in outcome.

Gene expression profiling has been utilized for the characterization of several neurological and immune disorders (5-7). In the case of cancer tissue samples the method has facilitated the identification and refinement of tumor subtypes (8), distinction between good-prognosis and poor-prognosis tumors (9) and the prediction of response to treatment (10). To date there are two reports of peripheral blood mononuclear cells (PBMCs) (11, 12) and one of peripheral whole blood (13) examining the changes of gene expression in patients following ischemic stroke. These studies provide a novel and sophisticated approach to identifying candidates for stroke diagnosis (14). However, the study designs are not complimentary; nor are the findings. Gene expression profiling of PBMCs captures a significantly smaller proportion of the differential gene expression following stroke compared to that which can be found in whole blood RNA (13). Thus, the purpose of our study was to determine the gene expression profile of peripheral whole blood following acute ischemic stroke in a larger cohort of stroke patients and control subjects, adjusting for common stroke risk factors in an attempt to replicate the findings of previous studies. This data can be used to examine the diagnostic capability of the candidate genes for ischemic stroke and to explore innate immune responses to ischemic stroke.

Methods.

This was a prospective case-control gene expression profiling study of peripheral whole blood in ischemic stroke patients. Recruitment was conducted from June 2007 through September 2008. Stroke patients were recruited from an IRB approved NINDS/NIH study at Suburban Hospital, Bethesda Md. after written informed consent was obtained when the following inclusion criteria were met: age ≥18 years; MRI diagnosed definite Acute Ischemic Cerebrovascular Syndrome (AICS15); and research blood draw within 24 hours from onset of symptoms. Patients with probable/possible AICS and hemorrhage (ruled out by MRI) were excluded from this study. The time of stroke symptom onset was determined as the time the patient was last known to be free of the acute stroke symptoms. Patient evaluations and management were standardized. Thrombolytic therapy with tissue plasminogen activator (rtPA) was given to patients with disabling symptoms within 3 hours from presentation to the clinical stroke team. Pre-morbid deficits were determined by the Modified Rankin Scale (MRS) during the acute clinical assessment for status prior to stroke and 30 days post-stroke and severity of injury was determined by the National Institutes of Health Stroke Scale (NIHSS) at the time of blood draw after stroke. Peripheral whole blood samples were collected from stroke patients into Paxgene blood RNA tubes (PreAnalytiX, Qiagen) within 24 hours from onset of stroke symptoms. Adult control subjects were recruited under a separate NIA/NIH protocol during support group sessions for patients with movement disorders if they were significant others of patients affected by movement disorders and they were neurologically normal per neurologist assessment at the time of enrollment. Clinical demographic data was collected from the stroke patient or significant other and all control subjects by trained neurologists.

RNA Extraction and Amplification.

Peripheral whole blood samples were collected from control subjects and stroke patients into Paxgene blood RNA tubes following consent. Paxgene RNA tubes were inverted 8-10 times to ensure RBC lysis, and immediately placed in a −80° C. freezer until RNA extraction. All frozen whole blood specimens were allowed to thaw at room temperature for 24 hours on a rotating bed prior to RNA isolation procedures to ensure complete red blood cell lysis. RNA was extracted from whole blood stabilized in Paxgene tubes in one batch per manufacturer's protocol using the Paxgene Blood RNA extraction Kit (PreAnalytiX, Qiagen). A recent study demonstrated that globin reduction does not increase the number of differentially expressed transcripts when hybridizing to HumanRef-8 v2 beadchips and therefore has little impact on probe detection when using the Illumina platform (16). Therefore, globin reduction was not conducted on any sample in this study. Biotinylated, amplified RNA was generated from the Illumina TotalPrep RNA amplification kit (Applied Biosystems). RNA quantity was determined by the Nanodrop and RNA quality was determined by A260/A280 ratio and the presence of two distinct ribosomal bands on gel electrophoresis.

Array Hybridization.

RNA was hybridized to Illumina HumanRef-8 v2 expression bead chips. The HumanRef-8 v2 bead chips have the capability to analyze >22,000 probes targeting genes and known alternative splice variants. Stroke patients and control subjects were randomly hybridized to each array for a total of 8 arrays (8 samples per array). Beadarrays were scanned by the Illumina BeadStation 500× and raw intensity values were saved in Illumina's Bead Studio program manager. Sample labeling, hybridization, and scanning were conducted using standard Illumina protocols.

Statistical Analysis.

Baseline descriptive statistics for the sample were computed using SPSS (version 15, SPSS, Inc., Chicago, Ill.). Descriptive and frequency analysis was conducted for all demographic and clinical data. Baseline demographic and clinical characteristics were compared between stroke patients and control subjects using chi-square analysis for the following categorical variables: gender, race, presence of comorbidities (hypertension, diabetes and hyperlipidemia), and medication history. Student's t-test was used to analyze the difference between stroke patients and control subjects by age. The level of significance for these descriptive comparisons was established at 0.05 for two-sided hypothesis testing.

Probe Level Analysis.

After scanning the beadchip the raw probe expression values were saved into Illumina BeadStudio Gene Expression (GX) Module (version 1, IlluminaR, San Diego Calif.) and GeneSpring GX v10 (Agilent technologies). Probes were filtered in GeneSpring based on signal intensity resulting in a final probe set of 24,424 to be used in analysis. The probe level data were collated using robust multi-array analysis (RMA) normalization with data processing occurring in the following order: 1) Background correction—using perfect match probe information only; 2) Quantile normalization-probe level normalization; and 3) Summarization-expression measure summary done in log base 2 scale and median was used to fit a linear model. Unsupervised clustering was performed without knowledge of class to determine phylogenetic distances between samples to detect potential outliers.

Gene Expression Level Analysis.

Data analysis for gene expression was conducted in Illumina BeadStudio Gene Expression Module and verified in GeneSpring. Genes with at least a 2 fold difference in expression were compared in a univariate manner between stroke patients and control subjects through the use of Illumina's custom model (modified t-test) in BeadStudio and t-test comparisons in GeneSpring. The influence of multiple testing was evaluated using the false discovery rate (FDR) and the Bonferroni Family wise error (FWER).

Logistic Regression for Identification of Off-Target Effects.

To assess the specificity of the 9 gene profile for ischemic stroke diagnosis, all 9 genes were tested independently in a logistic regression model controlling for age, hypertension and dyslipidemia. The normalized signal intensities for each gene were entered into separate models with age and then hypertension and dyslipidemia as the covariates of interest. A bonferroni corrected p of <0.005 (0.05/9) was considered to be statistically significant.

Pathway Analysis.

Data were interpreted through the use of INGENUITY® Systems Pathway analysis (IPA®) (INGENUITY®Systems, www.ingenuity.com). To increase the number of genes included in the analysis, genes with a 1.5 fold difference in expression between stroke patients and control subjects were chosen. The data set that contained gene identifiers and their corresponding expression signal intensities was uploaded into the INGENUITY® systems program. The gene list was compared one-by-one to the Canonical Pathways stored in the INGENUITY® systems knowledge base; pathways with significant p-values (p<0.05) were identified. The p-value measures how likely genes from the gene list participate in the function described in the specific pathway. The INGENUITY® systems software queried the INGENUITY® knowledge base and generated a set of networks with a network size of 35 genes/gene products. A score, which was derived from a p-value, was generated for each network according to the fit of the set of significant genes. Scores of 2 or higher were considered to have at least a 99% confidence of not being generated by chance alone. Biological functions were then calculated and assigned to each network. The significance of the association between the data set and the canonical pathway was measured in two ways: 1) a ratio of the number of significant genes that mapped to the canonical pathway (the number of molecules in a given pathway that meet the 1.5 fold cut off, divided by the total number of molecules that make up that pathway); and 2) A right tailed Fisher's exact test to calculate a p-value determining the probability that the association between the genes in the dataset and the canonical pathway is not explained by chance alone.

Polymerase Chain Reaction Validation.

cDNA was generated from total RNA per manufacturer's protocol. (Invitrogen, SuperScript III first strand synthesis kit). Quantitative real-time polymerase chain reaction (QRT-PCR) using Taqman gene expression probes was used to validate the significant transcripts identified in this study that overlapped with previous findings and one novel gene identified in this study. An endogenous control gene with a constant expression level between stroke patients and control subjects (Beta-actin) based on the microarray data was used to normalize the relative expression of chosen genes. When using Taqman gene expression assays the comparative CT method for determining relative fold change correlates well with expected fold change values (17). Therefore relative fold change differences between stroke patients and control subjects were calculated using the delta CT method (18). Validation was determined positive if the relative fold change in expression was in the same direction as what was identified with the microarray results, t-test analysis revealed significance and there was a positive correlation between QRT-PCR and microarray results.

Results.

Clinical Characteristics.

A total of 92 subjects (67 stroke patients and 25 control subjects) were recruited to address the aims of the study. Of the 67 stroke patients enrolled, 39 stroke patients received a diagnosis of definite AICS15 with an acute blood draw within 24 hours from onset of symptoms. Using the TOAST (Trial of ORG 10172 in Acute Stroke Treatment) subtype criterion 43.6% (n=17) of the causes were classified as cardioembolic stroke; 28.2% (n=11) were of undetermined cause; 12.8% (n=5) were large artery embolus/thrombosis and the remaining 15.4% (n=6) were small vessel or other cause.

The presence of comorbidity was prevalent in the stroke patient group, with 64% having a history of hypertension, 28% with a history of diabetes, 15.4% with a history of prior stroke, and 38% with a smoking history (previous or current). The mean time from symptom onset to acute blood draw (baseline RNA profile) was 10:06 hours±6:31. Nine (23.1%) of the patients received rtPA, of which only one patient had their blood drawn before rtPA administration. Stroke patients had a median pre stroke Modified Rankin Scale (MRS) score of zero, implying the absence of premorbid neurological deficits. Severity of stroke was mild with a median baseline National Institutes of Health Stroke Scale score (NIHSS) of 3 with a range from 0-23 and a hospital discharge NIHSS median of 0 with a range from 0-10. There was no difference by race or gender between the stroke patient and control subject groups. However, stroke patients were significantly older than control subjects (t=-4.03; p=0.000) and stroke patients were more likely to have the presence of comorbidities for which they were receiving medication. See Table 1, below.

TABLE 1

Univariate associations between stroke patients and control subjects

| | Total Sample | Stroke n = 39 (61.9%) | Control n = 24 (38.1%) | Statistic/df | p value |
|---|---|---|---|---|---|
| Gender (% female) | 36 (57.1%) | 22 (56.4%) | 14 (58.3%) | $\chi^2$ 0.02/1 | 0.883 |
| Mean age, years | 68.1 ± 14.02 | 73.1 ± 14 | 59.9 ± 9.73 | τ 4.4/61 | 0.000 |
| Hypertension | 32 (50.8%) | 25 (64.1%) | 7 (29.2%) | $\chi^2$ 6.6/1 | 0.010 |
| Diabetes | 13 (20.6%) | 11 (28.2%) | 2 (8.3%) | $\chi^2$ 3.3/1 | 0.068 |
| Dyslipiderma | 18 (28.6%) | 18 (46.2%) | 0 | $\chi^2$ 14.9/1 | 0.000 |
| Atrial Fibrillation | 6 (9.5%) | 6 (15.4%) | 0 | $\chi^2$ 3.9/1 | 0.048 |
| Myocardial Infarction | 6 (9.5%) | 6 (15.4%) | 0 | $\chi^2$ 3.9/1 | 0.048 |
| Previous Ischemic Stroke | 8 (12.7%) | 6 (15.4%) | 2 (8.3%) | $\chi^2$ 0.7/1 | 0.414 |
| Previous or Current smoker | 30 (47.6%) | 15 (38.5%) | 15 (62.5%) | $\chi^2$ 7.8/2 | 0.020 |
| Hypertension Medication | 37 (47.6%) | 29 (74.4%) | 8 (33.3%) | $\chi^2$ 10.3/1 | 0.001 |
| Diabetes Medication | 8 (12.7%) | 7 (17.9%) | 1 (4.2%) | $\chi^2$ 2.66/1 | 0.103 |
| Cholesterol Medication | 22 (34.9%) | 17 (43.6%) | 5 (20.8%) | $\chi^2$ 3.4/1 | 0.066 |
| Anticongulant or antiplatelet | 21 (33.3%) | 20 (51.3%) | 1 (4.2%) | $\chi^2$ 14.8/1 | 0.000 |
| Family history of Stroke | 19 (30.2%) | 15 (38.5%) | 4 (16.7%) | $\chi^2$ 3.6/1 | 0.169 |

Array Quality Control.

Total RNA purified using the Paxgene system was highly pure, with A260/A280 values between 1.9 and 2.2 and RNA yields >1-2 μg from 2.5 ml of peripheral whole blood. Hybridization controls were appropriate for low, medium and high. Negative control, background, and noise signals were low (<200) across all bead arrays and housekeeping and biotin signals were consistently high (>20,000). The average signal for internal controls across the arrays was similar. The control plots were consistent with high quality data.

Nine Gene Profile for Stroke.

All analyses were conducted first in Illumina BeadStudio Gene Expression (GX) Module (version 1, Illumina®, San Diego Calif.) and then in GeneSpring GX v10 (Agilent technologies) to verify the findings. Unsupervised clustering of samples revealed two outliers in the dataset (one stroke patient and one control subject). The outlying control subject was removed. It could not be determined if the patient sample was an outlier because of technical or biological variability and to keep credibility of the dataset, the patient outlier was kept in the analysis resulting in a final total of 39 stroke patients and 24 control subjects. BeadStudio identified 344 genes with a 1.5 fold difference in expression with a Diff score >13 (corrected p<0.05) between stroke patients and control subjects. There were 19 genes with a 2 fold difference in expression with a Diff score >13 (corrected p<0.05). See Supplemental Table 1, below.

SUPPLEMENTAL TABLE 1

Beadstudio 2 fold, p < 0.05 Gene List, 19 Genes

| Gene | Diff Score* | Regulation |
|---|---|---|
| ARG1 | 44.13 | up |
| BNIP3L | 25.68 | up |
| CA4 | 40.43 | up |
| CCR7 | −71.37 | down |
| CEACAM6 | 16.8 | up |

SUPPLEMENTAL TABLE 1-continued

Beadstudio 2 fold, p < 0.05 Gene List, 19 Genes

| Gene | Diff Score* | Regulation |
|---|---|---|
| CEACAM8 | 15.99 | up |
| CSPG2 | 53.25 | up |
| ECHDC3 | 17.85 | up |
| FKBP5 | 15.1 | up |
| IQGAP1 | 70.95 | up |
| KCTD12 | 14.99 | up |
| LY96 | 49.69 | up |
| MMP9 | 30.01 | up |
| OLFM4 | 18.97 | up |
| ORM1 | 17.00 | up |
| PDK4 | 102.71 | up |
| S100A12 | 39.53 | up |
| SDPR | 41.33 | up |
| TPST1 | 26.83 | up |

*Diff score: Using the Illumina Custom Algorithm a Diff score is calculated from the p-value of significance. {DiffScore = (10sgn(Icond − Iref)log10(p))} For each gene, Diff scores of corresponding probes are averaged and concordance between the probes is reported. For a p-value of 0.05, Diff score = ±13

Results were comparable in GeneSpring with 355 genes having a 1.5 fold difference in expression (corrected p<0.05) and 16 genes with 2 fold difference in expression between stroke patients and control subjects (corrected p<0.05). See Supplemental Table 2, below.

SUPPLEMENTAL TABLE 2

GeneSpring 2 fold, p < 0.05 Gene List, 16 Genes

| Gene | p-value* | Regulation |
|---|---|---|
| ACSL1 | 4.03e−04 | up |
| AKAP7 | 0.001 | up |
| APOBEC3A | 0.03 | up |
| ARG1 | 2.84E−07 | up |
| CA4 | 2.00E−04 | up |
| CCR7 | 4.37E−05 | down |
| CRISPLD2 | 4.74E−06 | up |
| CSPG2 | 3.45E−05 | up |
| FCGR3B | 0.024 | up |
| FOLR3 | 9.23E−04 | up |
| IQGAP1 | 7.97E−07 | up |
| LY96 | 0.001 | up |
| MMP9 | 1.11E−05 | up |
| ORM1 | 0.006 | up |
| PADI4 | 4.70E−06 | up |
| S100A12 | 3.87E−04 | up |

*Bonferroni Family wise error (FWER) corrected p-value

Legend:
ACSL1 = acyl-CoA synthetase long-chain family member 1;
AKAP7 = A-kinase anchor protein 7;
APOBEC3A = apolipoprotein B mRNA editing enzyme, catalytic polypeptide-like 3A;
ARG1 = Arginase 1;
CA4 = Carbonic anhydrase 4;
CCR7 = Chemokine receptor 7;
CRISPLD2 = cysteine-rich secretory protein LCCL domain containing 2;
CSPG2 = Chondroitin sulfate proteoglycan 2;
FCGR3B = Fc fragment of IgG, low affinity IIIb, receptor (CD16b);
FOLR3 = folate receptor 3;
IQGAP1 = IQ motif containing GTPase activating protein 1;
LY96 = Lymphocyte antigen 96;
MMP9 = Matrix metalloproteinase 9;
ORM1 = orosomucoid 1;
PADI4 = peptidyl arginine deiminase, type IV;
S100A12 = S100 calcium binding protein A12

After comparison between the findings of the two statistical programs, there were 9 genes significantly different between stroke patients and control subjects with at least a 2 fold difference in expression and corrected p<0.05 the same across the two statistical packages. See FIG. 1.

It is important to note that five of these 9 genes were also found to be significant in the first whole blood gene expression profiling study of stroke (ARG1; CA4; LY96; MMP9; S100A12) (13). See Table 2, below.

TABLE 2

Comparison of Gene List to Previous Study

| Gene | p value | Fold Change | p value | Fold Change |
|---|---|---|---|---|
| ARG1 | 2.84E−07 | 3.2 | 5.03E−04 | 3.8 |
| CA4 | 2.0E−04 | 2.1 | 3.54E−05 | 2.2 |
| LY96 | 0.001 | 2.2 | 3.67E−03 | 2.1 |
| MMP9 | 1.11E−05 | 2.6 | 3.54E−05 | 3.2 |
| s100A12 | 3.87E−04 | 2.4 | 2.59E−04 | 2.2 |

This Study
Tang et al 2006

Regression for Identification of Off-Target Effects.

Given the significant difference between stroke patients and control subjects by age, a logistic regression was performed to determine if the 9 genes in the identified profile were preferentially regulated by age. After controlling for the effects of age and correcting for multiple testing (p=9/0.05), s100A12 fell out of the model (p=0.014). See Table 3, below.

TABLE 3

Logistic Regression Controlling for Age

| Predictor | Odds Ratio | 95% CI for OR | p value |
|---|---|---|---|
| ARG1 | 0.061 | (0.012-0.312) | 0.001 |
| CA4 | 0.167 | (0.058-0.482) | 0.001 |
| CCR7 | 7.986 | (2.229-28.61) | 0.001 |
| CSPG2 | 0.223 | (0.086-0.628) | 0.004 |
| IQGAP1 | 0.061 | (0.011-0.339) | 0.001 |
| LY96 | 0.361 | (0.186-0.701) | 0.003 |
| MMP9 | 0.131 | (0.041-0.422) | 0.001 |
| ORM1 | 0.033 | (0.156-0.704) | 0.004 |
| s100A12 | 0.444 | (0.233-0.846) | 0.014 |

Note:
p < 0.005 statistically significant after Bonferonni correction

An additional logistic regression analysis revealed that ARG1 (p=0.002), CA4 (p=0.002), CCR7 (p=0.005), CSPG2 (p=0.003), IQGAP1 (p=0.003), and MMP9 (p=0.002) remained significantly associated with stroke diagnosis after controlling for history of hypertension and dyslipidemia.

Pathway Analysis.

There were 355 genes eligible for pathway analysis (at least a 1.5 fold difference in expression between stroke patients and control subjects and corrected p<0.05). IPA revealed the five most significant canonical pathways present in the peripheral whole blood RNA of stroke patients were CD28 signaling in T-helper cells (p=4.03E00), nuclear factor of activated T cells (NFAT) in regulation of the immune response (p=4.03E00), dendritic cell maturation (p=3.4E00), toll-like receptor (TLR) signaling (p=3.33E00), and calcium-induced T-lymphocyte apoptosis (p=2.92E00). Supplemental Data. However, there were more genes from our dataset differentially expressed in the TLR signaling pathway between stroke patients and control subjects than in any other identified pathway, (with a ratio >2 and p=3.33E00) implying the TLR pathway is the most significant for this dataset. See FIG. 2.

Taqman Gene Expression Assay Validation.

Taqman gene expression assays were used to confirm the beadarray results. QRT-PCR reactions were performed using Taqman® gene expression probes (Applied Biosystems) for the genes ARG1, CCR7, LY96, and MMP9 by the 7900HT QRT-PCR system based on availability of RNA. ARG1, LY96, and MMP9 was chosen because they were also significant in the first gene expression profiling study of stroke. CCR7 was the only down-regulated gene for stroke found in our study. QRT-PCR validated significant changes in mRNA levels in all 4 genes. It is important to note that the first gene expression profiling study conducted by Tang et al was not able to validate microarray results by limitations in the availability of RNA; for this same reason we could not validate the entire gene profile.

Discussion

A rapid blood test to confirm the diagnosis of ischemic stroke would transform stroke care in the US and across the world. We found that 9 genes were differentially expressed with at least a 2 fold difference between stroke patients and control subjects. Although the major limitation of our study was a younger control group, post-hoc analyses controlling for age and other stroke risk factors supported the primary analysis findings. In addition, the fact that 5 of the 9 genes identified in this study were also found to be significant in the first whole blood gene expression profiling study of ischemic stroke suggests that confounding factors as age, time after stroke and other factors probably did not radically affect our results and confirms the validity of this method for the identification of diagnostic biomarkers in this population.

Peripheral whole blood gene expression analysis in AICS patients identified 9 genes; 8 of which are up-regulated. These are Arginase 1 (ARG1); carbonic anhydrase 4 (CA4); chondroitin sulfate proteoglycan 2 (CSPG2); IG motif-containing GTPase activation protein 1 (IQGAP1); lymphocyte antigen 96 (LY96); matrix metalloproteinase 9 (MMP9); orosomucoid 1 (ORM1) and s100 calcium binding protein A12 (s100A12) and one down-regulated, the chemokine receptor 7 (CCR7) gene (see FIGS. 4-12 and the Detailed Description for Accession numbers, nucleotide sequences and amino acid sequences for each marker).

Comparison to Previous Studies

The inconsistency between the first three peripheral blood gene expression profiling studies of AICS is most attributable to the different sources of RNA under study. The first human study compared the gene expression levels in peripheral blood mononuclear cells (PBMC) between 20 ischemic stroke patients and 20 control subjects. Using prediction analysis for microarrays (PAM), the group identified a 22 gene panel that classified stroke in a validation cohort with a sensitivity of 78% and a specificity of 80% (12) The subsequent study performed by Tang and colleagues examined the gene expression profiles of whole blood in 15 stroke patients at 3 hours, 5 hours, and at 24 hours after ischemic stroke in comparison to 8 control subjects (13). The study revealed that the majority of the genes induced between 2 and 24 hours following stroke symptoms were induced in neutrophils and monocytes. Nearly all of the genes regulated at 3 hours were also regulated at 5 and 24 hours with greater numbers of genes expressed as time passed. These findings of this study suggested the use of peripheral whole blood gene expression is the most useful for making early diagnosis of ischemic stroke in humans. The third study examined the changes of peripheral PBMC's in patients 24 hours following stroke, and identified one gene with measurable differences between stroke patients and control subjects, phosphodiesterase 4 D (PDE4D), but no genes in common with the first two studies. (11)

There were 156 genes (11%) with at least a 1.5 fold change in expression coincident between the first two studies (14). However, when comparing the significant gene lists, only 2 genes were identified in both studies: N-acetylneuraminate pyruvate lyase (NPL) and v-ets Erythroblastosis virus E26 oncogene homolog 2 (avian). Tang and colleagues interpreted this lack of replication secondary to the fact that the majority of patients in the Moore et al study were treated with rtPA, the symptom onset time from blood draw (RNA profile assessment) was variable, and different cell populations were examined. Considering this, the group suggested that the changes of peripheral blood gene expression identified in the first 3 hours after ischemic stroke symptom onset prior to rtPA administration would be the most useful for discovering biomarkers for early stroke diagnosis. Thus they reported 18 significant genes with differential expression between stroke patients and control subjects at 3 hours after ischemic stroke symptom onset.

In this study, with regard to significant genes with at least a 2 fold difference in expression there was one gene coincident with the Moore et al study (CSPG2) and 5 genes overlapping with the Tang et al study (ARG1; CA4; LY96; MMP9; S100A12). Nine patients (23%) in our study received rtPA, a similar proportion to that of Moore's study, and the mean time from symptom onset to blood draw was 10:06 hours; more than the 3 hours suggested by Tang et al (13). It is remarkable that besides these differences 50% of the genes identified by Tang et al have been replicated in our study. This indicates first that the differences between the two first expression studies were due primarily to differences in cell populations under study; and second that expression in the genes found to be coincident with the Tang et al study are not reflecting changes secondary to administration of rtPA as previously considered, but rather are changes associated with ischemic stroke. These findings suggesting a larger time window beyond 3 hours for the identification of biomarkers of stroke diagnosis has tremendous clinical applications as the majority of stroke patients do not come to the hospital within 3 hours from onset of stroke symptoms. Previous proteomic blood biomarker studies of stroke performing poorly beyond 3 hours from stroke symptom onset (19), reinforces gene expression profiling as an alternative method of biomarker identification for stroke diagnosis.

The control subjects in this present study were matched for race and there was no significant difference in gender between stroke patients and control subjects. Although the stroke patients in our study were older than the control subjects, post-hoc analyses controlling for age and other stroke risk factors (e.g. hypertension and dyslipidemia) supported the primary analysis findings with the exception of s100A12.

The results of this study and the previous studies, suggest that the relative expression of ARG1, CA4, LY96, MMP9, and S100A12 taken together have strong evidence for diagnostic capability in acute ischemic stroke.

Aside from the comparability of these findings to the previous gene expression profiling study, MMP9 and various isoforms of S100 at the protein level have been implicated as biomarkers of ischemic stroke. One of our recent publications suggests baseline serum MMP9 may help to predict the occurrence of blood brain barrier disruption following ischemic stroke (20) and high levels of S100 serum protein have been associated with poor outcome following stroke (21), implying they may be useful as prognostic markers.

Novel Candidates for Biomarkers of Stroke

In addition to the 5 genes identified by this study and the previous study by Tang et al, we have identified other novel candidates for stroke diagnosis: CCR7, CSPG2, IQGAP1, and ORM1.

Chemokine Receptor 7 (CCR7)

CCR7 is a member of the G-coupled chemokine receptor family. Inflammatory chemokines function mainly as chemoattractants for leukocytes, recruiting monocytes, neutrophils and other effector cells from the blood to sites of infection or tissue damage (22). That cytokines could be the driving force in the neuroinflammatory immune response following stroke, is suggested as specific cytokines have shown to exacerbate brain damage (23) and pharmacological chemokine receptor antagonists have been reported to reduce infarct volume in mice (24, 25). In addition chemokines directly affect blood brain barrier (BBB) permeability via alterations in tight junction (TJ) proteins in an in vitro BBB model (co-cultures of endothelial cells and astrocytes) (26). Interestingly chemokines also play an important role in vasculogenesis by augmenting endothelial progenitor cell (EPC) recruitment in ischemic tissues (27, 28).

Most of the knowledge on the involvement of CCR7 in the development of immunity and tolerance in stroke is derived from mouse models, whereas the data on CCR7 function in humans is rather sparse. Increased levels of CCR7 have been found in experimental stroke rat brain at 22 hours following injury, in contrast with a significant reduction of CCR7 mRNA in spinal cord, suggesting a compensatory response to intracranial events (29). In humans, an increase of CCR7+ T cells has been reported in peripheral blood leukocytes (PBL) of ischemic stroke patients with mild to moderate severity 1 week following stroke (30). In this study, down regulation of CCR7 was found in the peripheral blood in the acute phase of ischemic stroke. Differences in the direction of the regulation could be explained as differences in tissue/cell-specific immune response or different immune responses following stroke progression. Another possibility is that our findings are reflecting immune responses after stroke of mild severity, as most of our patients had mild stroke symptoms. One third possibility is the down regulation of CCR7 is a consequence of the increased age of our stroke patients, as age-associated reductions in CCR7 expression has been reported in animal models (30). However, the logistic regression performed correcting for age, suggests that CCR7 is associated with stroke independent of age. If the response of CCR7 is related to age, tissue, cell population, severity of AICS or stage of AICS progression, further studies of CCR7 and stroke should address this issue.

Chondroitin Sulfate Proteoglycan 2 (CSPG2)

CSPG2, also known as versican, is a primary component of the extracellular matrix in the central nervous system (CNS). CSPG2 is involved in cell adhesion, proliferation, migration and angiogenesis (31). Several experimental studies have demonstrated elevated expression of CSPGs in response to brain injury (32, 33). Diminished versican expression in brain has been associated with deep cerebral white matter injury in neonatal hypoxic-ischemic rat injury (34). Furthermore, it has been reported that CSPG2 expression is dramatically increased within the infarct core following ischemic stroke, resulting in increased cell death and reactive astrocytosis (35). In a rat model of myocardial infarction, versican expression is upregulated in monocytes and macrophages within the infarcted myocardium (36) To our knowledge, studies of CSPG2 expression in humans are absent with the exception of the first blood gene expression profiling study of stroke (12), which identified CSPG2 as one of the significant genes that classified stroke with a specificity of 80%. Up-regulation of CSPG2 in our dataset is consistent with these findings.

IQ Motif-Containing GTPase Activating Protein 1 (IQGAP1)

IQGAP1 is an evolutionarily conserved molecule that serves as a scaffold protein and plays a fundamental role in cell polarity. It modulates several cellular activities including cytoskeletal architecture, cell-cell adhesion, transcription and signaling (ERK signaling) (37). Rho-family GTPases, are a family of small signaling G proteins that require IQGAP1 to regulate actin cytoskeleton to produce a gradient of signaling molecules (38). Experimental evidence suggests that the expression of RhoA increases in aortic and basilar arteries with age (39), therefore RhoA, and indirectly IQGAP1, may play a role in taltered vascular responses associated with aging (39). Furthermore, studies in vitro have suggested that leukocyte transmigration and changes in endothelial permeability can be facilitated by RhoA (40). It has been shown that down-regulation of Rho improves endothelial barrier function (41), however long-term inactivation of Rho can lead to loss of intercellular junctions and an increase in endothelial permeability through disrupting VE-cadherin and cell-cell adhesion (42). The up-regulation of IQGAP1 expression in the context of ischemic stroke could suggest an increase in cellular signaling and transcription in the acute phase of ischemic stroke leading to increased permeability of the BBB. IQGAP1 may mediate the disruption of the BBB as a means by which signals from the brain enter the periphery to augment cellular recruitment.

Oromucosid 1 (ORM1)

Finally, ORM1 also known as alpha-1 acid glycoprotein is an acute phase protein and increases 2-5 times during an acute phase response. ORM1 has been shown to suppress lymphocyte response to lipopolysacchardies (LPS) (thereby preventing ongoing tissue damage by neutrophil proteases), decrease platelet aggregation (and thus further platelet recruitment), and enhance cytokine secretion as possibly part of a feedback mechanism (43). It exhibits anti-inflammatory effects by inhibiting polymorphonuclear neutrophil activation and increasing the secretion of IL-1 and is therefore suggested to play a significant role in immunomodulation of the acute phase response (44). The up-regulation of ORM1 in the context of ischemic stroke suggests an acute phase response in ischemic stroke that is similar to trauma, infection and systemic tissue injury.

Toll-Like Receptor Signaling

Figure 3:
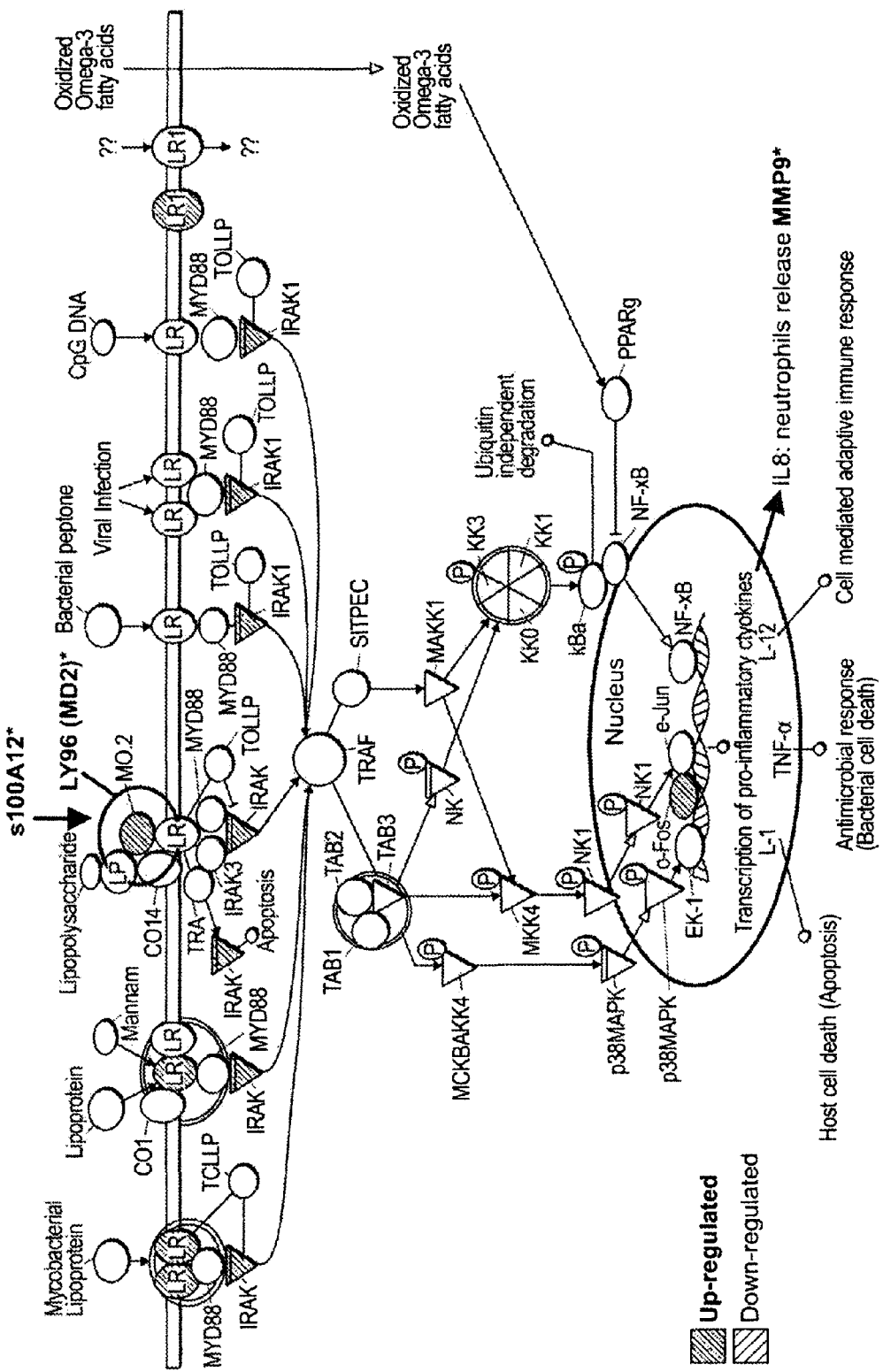
FIG. 3 provides a schematic depicting Toll-like Receptor Signaling. There were more genes involved in the Toll-like receptor signaling pathway in our dataset compared to the total number of genes in the Toll-like receptor pathway with a ratio >2 and $p=3.33E00$ (TLR2, TLR1, FOS, LY96, TLR8 (includes EG: 51311), IF2AK2, IRAK3). The activation of the TLR4/LY96(MD2) complex and TLR2 from endogenous alarmins such as s100A12 results in activation of IRAK1 through interaction with MyD88. This leads to engagement of TRAF6, which is a member of the TNF receptor family. Then through the IkappB kinase pathway, NF kappaB translocates from the cytoplasm to the nucleus where it stimulates transcription of both proinflammatory and anti-inflammatory cytokines and chemokines (e.g. pro inflammatory IL6 and IL8 (resulting in neutrophil release of MMP9); anti-inflammatory IL10 and TNFα). Simultaneous with NfkappaB activation, engagement of TRAF6 also results in: 1) the stimulation of the JNK pathway and activation of immediate early response genes cJun and cFos which come together to form the API early response transcription factor which increases the activation of the MAPK signaling cascade with subsequent ELK1 activation with binding to the serum response factor (SRF) in the promoter of the cFos proto-oncogene. Therefore, within the TLR pathway there are both pro-inflammatory mechanisms of engagement (NF-kappaB) and anti-inflammatory and neurotrophic pathways of regeneration (BDNF and SRF).

IPA analysis identified TLR signaling as the most significant canonical pathway present in the peripheral blood of ischemic stroke patients in this dataset. The genes differentially expressed between stroke patients and control subjects identified in the TLR pathway are TLR2, TLR1, FOS, LY96, TLR8 (includes EG:51311), IF2AK2, and IRAK3. See FIG. 3.

The TLR pathway is a necessary component of the innate immune system. Recent evidence suggests the TLR system as a key player in ischemic preconditioning and therefore may be a novel target for stroke therapeutics (45). Activation of the innate immune response, through TLRs, is a primary component of pro-inflammatory cytokine generation following ischemic brain injury (46). TLRS recognize pathogen associated molecular patterns (PAMPs), a diverse set of stress and injury-induced molecules with highly conserved structures, to initiate the innate immune response to infection. Traditionally the PAMP/TLR activation pathway was primarily implicated in tolerance to endotoxins that alert an organism to intruding pathogens. However, it is becoming increasingly clear that microbial invasion is not the only mechanism by which the TLR pathway becomes activated (47, 48). Products of protein degradation, damaged DNA, fibrinogen and heat shock proteins have emerged as activators of the TLR pathway through a mechanism known as damage associated molecular pattern (DAMPs) recognition (48).

Several studies have shown that the responsiveness of the adaptive immune system dramatically decreases with age (49) and a pro-inflammatory shift in gene expression occurs with increasing age (50, 49). TLRs are upregulated in the aged mouse brain (51) and specifically, TLR4 is upregulated in the cardiovascular system of aged rodents (50). However, the expression of TLR2 and TLR4 on neutrophils is not affected by age, (52) which has implications for this present study given the RNA profile under study was extracted from peripheral whole blood. On the other hand, TLR2 and TLR4 have been shown to play a significant role in ischemic brain damage, regardless of age (53). Activation of the innate immune response, through TLRs, is a primary component of inflammatory activation following ischemic brain injury, (46) and TLR4 activation has recently been implicated as a negative effector of the innate immune response (54). Down regulation of TLR4 results in a decrease in final infarct volume and better outcome in a mouse middle cerebral artery occlusion (MCAO) model. TLR4 deficient mice are protected by ischemic injury through a down-regulation of inducible nitric oxide synthase (iNOS) production (55, 56). In addition, mice who are TLR4 deficient also have better behavior following MCAO that is preceded by significant psychological stress (57). Human studies have added to this theory of TLR mediated negative outcome and have identified that increased activation of TLR4 following ischemic stroke corresponds to worse clinical outcome (58, 59).

Strong evidence suggests that stroke and aging are associated with an increase in inflammatory mediators; however, the relationship between stroke and aging on innate immunity, toll like receptor signaling and inflammatory gene expression warrants further investigation. The predominance of these innate and inflammatory immune pathways in our study reinforces their importance in ischemic stroke. At present, although progress has been made, a better understanding of how these pathways react and respond to ischemic stroke may lead to the emergence of new avenues for therapeutic intervention. The TLR pathway is a promising and worthy target to be considered and studied with more detail.

The results of this study provide insight into the molecular mechanisms involved in cerebral ischemia. Nine genes were differently expressed with at least a 2 fold difference between stroke patients and control subjects. The study replicates the findings of a previous gene expression study of ischemic stroke (13). and therefore supports the use of gene expression profiling of peripheral whole blood to identify biomarkers of AICS.

Example 2

Gene Expression Profile for the Diagnosis of Ischemic Stroke

Specific Aims Introduction.

Stroke is the third leading cause of death in the United States (60) and accounts for 10% of deaths worldwide (61). Clinical diagnosis of ischemic stroke is often difficult, complicated by its multiple etiologies and variable clinical presentation. Most hospitals in the United States use CT to initially evaluate patients suspected of having an acute stroke; however CT is less than optimal for identifying acute ischemia (62). The only Food and Drug Administration (FDA) approved treatment for ischemic stroke is recombinant tissue plasminogen activator (rtPA), and rtPA is only approved for use when patients present to the hospital within three hours after onset of symptoms. The downside is that the median time from stroke symptom onset to presentation to the emergency department is 3-6 hours (63). (It is noted that this Example 2 includes a separate listing of references to which the text makes reference to).

Currently only 3-8% of stroke patients receive rtPA (64). The recent extension of the time window to up to about 4.5 hours is likely to change this proportion only modestly. Where possible, hospitals are moving toward using MRI for acute diagnosis of stroke; however this often requires a dedicated stroke clinical team and is only possible in facilities with 24 hour MRI availability. Quick and definitive diagnosis in the acute care setting is essential to separate stroke from non-stroke, distinguish hemorrhage from ischemia, and identify the potential cause of the infarction, but most importantly to determine eligibility for thrombolytic therapy to begin treatment within the about 3 to 4.5 hour window of opportunity.

An additional diagnostic measure, such as a serologic blood test or a screen of a panel of markers, would be extremely beneficial in obtaining a definitive diagnosis of acute stroke to help increase the utilization of rtPA, especially in hospitals that are not stroke centers.

In Example 1, a nine gene panel of biomarkers was identified in the peripheral whole blood of ischemic stroke patients which can be used for acute diagnosis of ischemic stroke (65). The nine genes identified in Example 1 and discussed elsewhere in this application predicted stroke with an accuracy of 95%; which is higher than the diagnostic capability of either MRI (85%) or CT (54%) (62).

An additional experimental goal is to validate these findings in a larger age matched cohort of stroke patients, disease control subjects and stroke-free control subjects to further ensure the differential diagnostic capability of the panel.

This Example outlines a project to validate gene expression profiles for the acute diagnosis of ischemic stroke, which will lead to improved assessment and treatment of patients who experience a stroke. Gene expression profiling is an effective approach to identify genes and pathways that predict a phenotype and clinical outcome.

The inventors have determined that expression profiling of peripheral whole blood could be used to differentiate stroke from stroke mimic, as well as to predict the clinical trajectory following a neurologic insult.

The Specific Aims of this Example:

Specific Aim [1] To validate and replicate a gene expression profile for the diagnosis of ischemic stroke in a larger cohort of ischemic stroke patients, using neurologic disease control patients. The neurologic disease groups include: 1) patients with CT or MRI confirmed acute ischemic stroke (IS) of all severities (n=75); 2) acute (<24 hrs) transient ischemic attack (TIA) patients (n=75); and 3) intracerebral hemorrhage (ICH) patients (n=50).

Specific Aim [2] To determine if the gene profile is specific for ischemic stroke by comparing the gene profile in neurologic disease patients (IA, TIA and ICH) with patients following acute inflammatory/ischemic stress (myocardial infarction (MI) or age matched normal controls.

Specific Aim [3] To develop a filament based point of care (POC) test that can be used at the bedside for differential diagnosis of ischemic stroke, which will be based on gene expression profiles validated in Specific Aims [1] and [2].

A secondary aim of this study is to identify the peripheral blood gene expression profile associated with clinical outcomes at 30 and 90 days in order to determine whether the identified gene activity can be used to predict recovery from ischemic stroke.

Background and Significance.

Gene Expression Profiling in Neurological Disease:

A novel approach to the study of ischemic stroke is the use of gene expression profiling to discover biomarkers that improve acute stroke diagnosis, identify secondary complications or aid in the development of novel stroke therapeutics. Gene expression profiling has the potential to identify biomarkers for many acute neurological diseases, as well as stratifying risk for patients with common asymptomatic neurological diseases, such as asymptomatic aneurysm and carotid stenosis. A stratification of risk based on a blood gene profile would aid in the decision to treat or not to treat, dramatically improving current treatments.

Blood Biomarkers for Stroke Diagnosis:

There has been a substantial attempt to identify blood biomarkers for ischemic stroke in the past; however the task has proven difficult and has not provided successful results. Many potential blood markers of ischemia and inflammation are also found in other conditions that may mimic stroke, which complicates the ability to identify a specific biomarker of stroke. A recent meta-analysis of published blood biomarker studies for stroke revealed significant methodological and design weaknesses in the studies including small sample size, poor references, and poor choice of control subjects and lack of validation. An ideal biomarker panel should distinguish ischemic stroke from stroke mimic and hemorrhage, be available in small centers without the need for interpretation outside of the facility, and easily accessible.

Study:

This Example outlines a validation study to determine a gene expression profile that can be used in the acute care setting for ischemic stroke diagnosis. Example 1 identified nine genes that were differentially expressed with at least a 2 fold difference between stroke patients and control subjects. To further validate the results of Example 1, this Example proposes to recruit age-matched stroke-free controls and a separate group of neurologic disease and inflammatory stress disease controls to determine the differential diagnostic capability of the nine gene panel of the invention (markers identified as Arginase 1 (ARG1); carbonic anhydrase 4 (CA4); chondroitin sulfate proteoglycan 2 (CSPG2); IG motif-containing GTPase activation protein 1 (IQGAP1); lymphocyte antigen 96 (LY96); matrix metalloproteinase 9 (MMP9); orosomucoid 1 (ORM1) and s100 calcium binding protein A12 (s100A12) and one down-regulated, the chemokine receptor 7 (CCR7) gene).

Filament Based Point of Care (POC) Test:

Dr. Haselton and his group at Vanderbilt University have developed a filament-based point of care (POC) test for bedside diagnosis of infectious diseases (See U.S. Patent Application No. 20060121481, which is incorporated herein by reference; also see Stone et al., Ann Biomed Eng., 2006 November; 34(70):1778-85; Stone et al., J Biomed Opt., 2006, May-June; 11(62):34012; and Stone et al., Biotechnol. Bioeng., 2005, Sep. 20; 91(65):699-706, each of which are incorporated herein by reference).

Figure 13:
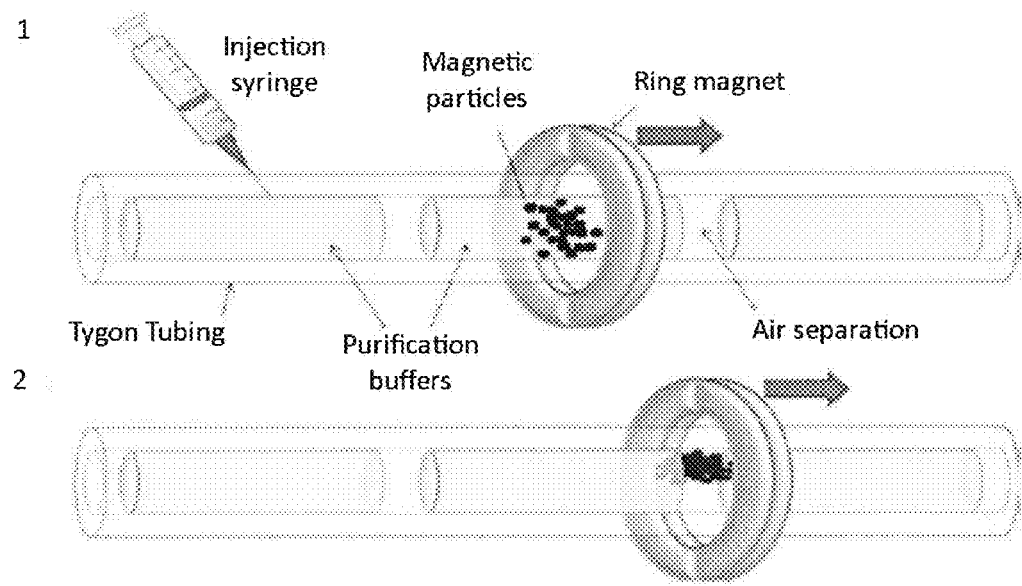
FIG. 13 depicts a simple pull-through DNA/RNA extraction design, i.e., a filament based Point of Care (POC) test of the invention. In this system, 100 µl of each consecutive treatment buffer is pre-loaded by injecting through the wall of the Tygon tubing. High surface tension forces between the liquid/air interface in this small diameter tubing maintain solution separation. A ring magnet is moved longitudinally along the length of the Tygon tubing thereby pulling magnetic particles containing nucleic acid molecule of interest bound thereto across air separations from one purification buffer to the next.

The technology uses DNA beacons on a gold wire to detect RNA in a small biological solution (73). In the prototype design, extraction is performed as illustrated in FIG. 13. Silica-coated magnetic particles are mixed with a patient sample and pulled through processing solutions in the device by an external magnet. Nucleic acid, in this case RNA, is freed from the particle surface in elution buffer. At this point, capture beacons on a gold wire are exposed to the isolated RNA. As the wire is pulled upwards through the device by a small machine, the gold wire passes through further processing chambers. The molecular beacons are then positioned within the top reporting chamber. It is contemplated that this platform could be used in an over-the-counter capacity. As part of this study, a prototype of the POC will be developed and evaluated for the gene profile of the nine biomarkers (or a subset of same) identified and validated in this study. This prototype will then be tested in the field for acute stroke definitive diagnosis in a multi-site clinical trial.

Research Design and Methods.

Research Design:

A matched case-control, repeated measures design is proposed to validate the nine gene profile of the invention in its capacity to detect ischemic stroke in patients as compared to neurologic disease control patients, acute inflammatory/ischemic stress control patients and stroke-free age-matched control subjects. The diagnostic capability of the panel will be tested to ensure that the profile withstands differential diagnosis of TIA and other neurologic diseases that can mimic stroke in the acute care setting. This study will be crucial in identifying the utility of an RNA based POC test for differential diagnostics of neurological disease.

Subjects:

Male and female subjects will be recruited from Mayo Clinic, Jacksonville Fla. if they are over age 18 years, present to the emergency room within 24 hours from onset of symptoms and:

Ischemic Stroke (IS): Symptoms of acute onset of neurologic dysfunction of any severity consistent with focal brain ischemia and imaging (MRI or CT) or laboratory confirmation of an acute vascular ischemic pathology (74).

Transient Ischemic Attack (TIA): Symptoms of acute onset of neurologic dysfunction of any severity, that is transient and caused by focal brain, spinal cord, or retinal ischemia, without acute infarction (75).

Acute myocardial infarction (AMI): Symptoms associated with ST segment elevation MI (STEMI). ECG elevation of ST-segments by >0.1 mV in contiguous leads in patients with ischemic symptoms. Increased cardiac biomarkers (>99th percentile of the upper reference limit for cardiac troponin 1 (TnI), cutoff 0.04 µg/L).

Intracerebral hemorrhage (ICH): Have symptoms suggestive of intracerebral hemorrhage (ICH) with a diagnostic CT scan Stroke-free age-matched control subjects: No major CNS disease or history of acute ischemic stroke or TIA. They answer positively to any item on the Questionnaire for Verifying Stroke-Free Status (QVSS) (17). The sedimentation rate is >19 mm for men or >22 mm for women (77).

Exclusion Criteria:

Diagnosis of pre-existing condition, including a chronic inflammatory disorder, such as celiac disease, vasculitis, lupus, chronic obstructive pulmonary disease, irritable bowel disease, arthritis, and psoriasis or pregnancy.

Study Material and Methods:

IS, TIA, ICH and AMI patients will be assessed as soon as possible following presentation to the ED (day 0), and at 24 hours after admission. Long term follow-up evaluations will be performed at 30 days following onset of symptoms for the 4 patient groups.

Stroke-free age-matched control subjects will undergo an evaluation at baseline and will not be followed over time.

Collection of Venous Blood Samples:

Peripheral blood samples will be collected on all patients and controls at each evaluation. Samples to be collected include: 5 ml blood in Paxgene blood tubes (for RNA), 8 ml blood in ACD tubes (DNA); and 8 ml blood in EDTA tubes (WBC). All samples will be processed appropriately and frozen at −80 until analysis.

Human Ref-8 v2 Expression Bead Chips:

RNA will be extracted from venous whole blood samples according to Paxgene blood RNA protocol. Illumina human Ref-8 v2 expression bead chips will be used for the study and have the capability to analyze 18,631 unique curated genes at once. The multi-sample format allows for up to eight samples to be arrayed in parallel, increasing throughput and decreasing experimental variability. Sample labeling, hybridization, and scanning will be conducted using standard Illumina protocols. QRT-PCR will be used to validate microarray data.

Clinical Severity and Outcome Measures:

The National Institutes of Health Stroke Scale Score (NIHSS) is a 15-item assessment tool that provides a quantitative measure of neurologic deficit. It assesses level of consciousness, gaze, visual fields, facial weakness, motor performance of the extremities, sensory deficit, coordination (ataxia), language (aphasia), speech (dysarthria), and hemi-inattention (neglect). For all parameters, a value of 0 is normal; so, the higher the score, the worse the neurological deficit (the highest possible score is 42). The NIHSS will be performed during the baseline assessment and at subsequent evaluations (24 hours and day 30).

Functional outcome will be determined using the Modified Rankin Scale (MRS) at 30 days post onset of symptoms in all patients. The MRS (78) measures degree of disability following stroke on a 0-6 scale, from no symptoms to death.

The Barthel Index (BI) (79) is a test of independence and scores the ability of a patient to care for himself and will be determined at 30 days. The values assigned to each item are based on time and amount of physical assistance required. A patient scoring 100 BI is continent, feeds himself, dresses himself, gets up out of bed and chairs, bathes himself, walks at least one block, and can ascend and descend stairs. The total score however, is not as significant or meaningful as the breakdown into individual items, since these indicate where deficiencies are.

The Extended Glasgow Outcome Scale Score (EGOS) is an 8 level scale ranging from Death to Upper Good Recovery and will be used to determine functional outcome at 30 days (80).

The Seattle Angina Questionnaire (SAQ) is a reliable instrument that measure five clinically important dimensions of health and will be used to address health-related quality of life outcomes in AMI patients at 30 days post onset of symptoms (81).

Covariates:

Potential covariates include severity of injury (determined by the NIHSS and clinical assessment), history of comorbidities (e.g. presence of hypertension), and medication history. A detailed history will be obtained from the patient and/or patient representative during the acute clinical work up. A modified k-prototypes algorithm for clustering biological samples based on simultaneously considering gene expression data and classes of known phenotypic variables will be used during statistical analysis to attempt to control for these covariates (82).

Power Analysis:

Sample size calculations have been conducted using PASS: Power Analysis and Sample Size System and JMP software. A 2.0 fold change is generally expected in genes of significance; however a smaller fold change of 1.5 may be used to identify genes not that differentially expressed between similar groups.

For Specific Aim 1 and Aim 2 group sample sizes of 50 achieve 95% power for each gene to detect a true difference in expression of at least 1.5 with estimated group standard deviations of 1.5 and 1.5 and with a false discovery rate (FDR) of 0.0500 using a two-sided two-sample T-Test. For a single test, the individual test alpha is 0.0002092. The probability of detecting 100 genes with true mean difference in expression >1.5, is 0.00668. Since patients will be matched to controls by age over-recruitment of patients will be conducted to ensure appropriate power to address Specific Aims 1, 2 and 3.

Therefore a total N of 325 will be recruited. N=75 Acute Ischemic Stroke; N=75 Transient Ischemic Attack; N=50 Myocardial Infarction; N=75 Stroke-free Volunteers; and N=50 Intracerebral hemorrhage.

Development of POC Device:

The POC design includes nucleic acid isolation, target binding, and result reporting. Silica-coated magnetic particles are mixed with a patient sample and injected through the wall of Tygon tubing. In the prototype design the Tygon tubing has been pre-loaded with 100 ul of each of the processing buffers arranged along the length of tubing held in place by surface tension forces. Magnetic beads are entrained by an external magnet and pulled through each of the processing solutions. When the beads reach the liquid-air interface they pass through without entraining the solution. Entry into the next solution proceeds similarly until the entire cloud of particles has passed through all of the process steps (about 2 minutes). The final elution buffer removes the RNA from the bead surface and will be used in downstream processing to detect markers of interest.

Candidate MB structures will be evaluated using synthetic targets using methods reported in our recent Analyst publication (83). The experimental studies of Aim 3 will be performed using real-time PCR and modifications of a single MB design coupled to the surface of gold nanoparticles. Performance as measured by fluorescence of candidate MB/nanoparticle construct will be compared to a matched control beacon using increasing concentrations of synthetic target alone and in the presence of a non-specific control target and by adding known concentrations of the synthetic target to patient samples before and after the performance of a RNA extraction. Our goal is to identify those features of the molecular beacon structure and its interaction with the gold surface that are the most robust in the presence of any residual patient sample constituents contained in solution with extracted RNA.

Figure 14:
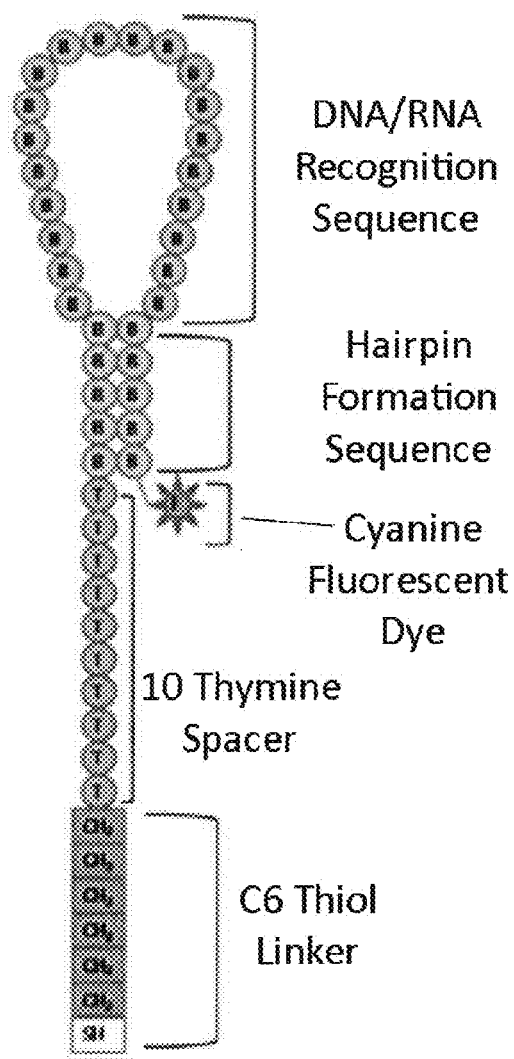
FIG. 14 is a schematic of a molecular beacon for use in the present invention. Near the 3' end, binding of DNA or RNA complementary to the loop region opens the stem region and the cyanine fluorescent dye moves away from the gold surface attached via a T spacer & C6 thiol linker at the 5' end.

Optimization of the Stem and Loop Structures of the Molecular Beacon ("MB"):

One molecular beacon contemplated by the invention is presented in FIG. 14. One additional aim of this Example is focus on improving both the capture and reporting functions of MB in the likely patient sample matrix by modifying stem and loop region lengths (84).

Hydrolytic Amplification:

To increase the limit of detection, a mixture of MB will be coupled to the gold surface with loop structures complementary to sequences unique to the DNA. To quantify hydrolysis, the extracted samples will be run on an Agilent 2100 Bioanalyzer and the resulting electropherograms will be examined. The signal produced by homogenous MB on a gold surface will be compared to the signal produced by heterogeneous MB coupling on a gold surface, with and without hydrolysis.

Amplification of Fluorescence Signal Using Multivalent QDs:

To achieve the necessary level of detection, the incorporation of amplification features into the device design will be examined. The fluorescence signal associated with MB opening is increased by assembling large fluorescent structures through alternating exposure of the capture region of the gold containing these MB to multivalent streptavidin quantum dots and then multivalent biotin quantum dots. The upper limit of fluorescence signal will be determined by an alternating quantum dot coupling method by plotting the average fluorescence as a function of the number of amplification steps.

Thermal Specificity Studies of MB on Gold.

A patient extract sample may result in high non-specific MB opening and therefore loss of specificity which could negatively impact the limit of detection. The temperature control features of a real time PCR machine will be used to study molecular beacon fluorescence response to patient sample extracts as a function of temperature to establish the importance of controlling the temperature for maximum signal for obtaining reproducible results; and secondly, identify the optimum temperature for differentiating between targets which exactly match the beacon loop sequence and all other bound species.

Data Analysis.

Descriptive Statistics:

Baseline descriptive statistics for the sample will be computed using SPSS (version 15, SPSS, Inc., Chicago, Ill.). Baseline demographic and clinical characteristics will be compared between IS patients of differing severity and IS and control subjects using chi-square analysis for the following categorical variables: gender, race, presence of comorbidities (HTN, DM, etc.), and medication history. The level of significance for these descriptive comparisons will be established at 0.05 for two-sided hypothesis testing. Hierarchical linear modeling will be used to compare the trajectory of the gene expression response across time after injury by severity of IS.

Differential Expression Analysis:

After scanning the beadchip the raw probe expression values will be saved into Illumina BeadStudio Gene Expression (GX) Module (version 1, Illumina®, San Diego Calif.). Specific Aim One: Data analysis for gene expression will be conducted in GeneSpring GX v10 (Agilent technologies) and R© (GNU). Genes with at least a 2 fold difference in expression will be compared in a univariate manner between stroke patients and neurologic disease control patients through the use of ANOVA in GeneSpring. Specific Aim Two: Genes with at least a 2 fold difference in expression will be compared in a univariate manner between stroke patients, acute inflammatory/ischemic stress control patients and stroke-free age-matched control subjects through the use of the ANOVA in GeneSpring. For Aims 1 and 2, the uncorrected probability values will be assigned a cutoff threshold value of significance of <0.05. Inflation of type one error from multiple hypothesis testing will be corrected by the Bonferroni Family wise error (FWER) and a false detection rate of <0.05 after correction will be considered statistically significant.

Logistic Regression for Identification of Off-Target Effects:

To assess the specificity of the identified gene profile for ischemic stroke diagnosis, the profile will be tested independently in a logistic regression model controlling for hypertension and dyslipidemia. The normalized signal intensities for each gene will be entered into separate models with age and then hypertension and dyslipidemia as the covariates of interest. A bonferroni corrected p of <0.005 will be considered to be statistically significant.

Pathway Analysis:

Data will be interpreted through the use of INGENUITY® Systems Pathway analysis (IPA) (INGENUITY® Systems, www.ingenuity.com). Genes with a 1.5 fold difference in expression between stroke patients and control subjects will be identified. The data set that contains gene identifiers and their corresponding expression signal intensities will be uploaded into the INGENUITY® systems program.

Secondary Aim:

The change in the gene expression profile over time (baseline to 24 hours) will be analyzed in comparison to MRS. The profile obtained in stroke patients from the baseline time point in aim one will be assessed at 24 hours and the change in the profile will be explained as change in the regulation of the gene set from baseline to 24 hours. MRS at 30 days will be divided into a binary variable as good outcome (MRS 0-1) and bad outcome (MRS 3-6). Genes with at least a 2 fold change in expression over time will be compared in a univariate manner between stroke patients with good or bad outcomes through the use of t-tests in GeneSpring.

Relevance and Innovation:

This project has the capability to identify biomarkers associated with response to ischemic stroke (IS) and elucidate complex genomic interactions that may play a role in outcome following IS. This study is innovative in that we are proposing one of the first bedside RNA diagnostic tools for neurologic disease. Interdisciplinary collaborations across multiple sectors, such as that proposed in this project, are required to push bench concepts of RNA based diagnostics to patients at the bedside.

Example 3

Validation of 9-Gene Biomarker Panel by Further Bioinformatic and Biostatistical Analysis Using INGENUITY® Systems, Inc.'s IPA® Software Package The data of Example 1 was further analyzed using INGENUITY® Systems, Inc.'s IPA® software package to determine the most relevant biological pathways likely to involve the group of biomarkers of the invention, namely, chemokine receptor 7 (CCR7); chondroitin sulfate proteoglycan 2 (CSPG2); IQ motif-containing GTPase activation protein 1 (IQGAP1); orosomucoid 1 (ORM1); arginase 1 (ARG1); lymphocyte antigen 96 (LY96); matrix metalloproteinase 9 (MMP9); carbonic anhydrase 4 (CA4); and s100 calcium binding protein A12 (s100A12), wherein at least one of the biomarkers is chemokine receptor 7 (CCR7); chondroitin sulfate proteoglycan 2 (CSPG2); IQ motif-containing GTPase activation protein 1 (IQGAP1); or orosomucoid 1 (ORM1).

Result A. Analysis of stroke versus control data validated the 9 gene panel of the invention. INGENUITY® pathway analysis identified the following cononical pathways as most likely to involve the 9-gene biomarker panel of the invention:

PI3K signaling in B lymphocytes; $p=4.72E-05$; 11/147 (0.075)

Role of macrophages, fibroblasts and endothelial cells in rheumatoid arthritis; $p=1.57E-04$; 17/359 (0.047)

Altered T cell and B cell signaling in rheumatoid arthritis; $p=1.9E-4$; 8/91 (0.088)

Toll-like receptor signaling; $p=2.6E-04$; 6/54 (0.111)

Primary immunodeficiency signaling; $p=4.5-04$; 6/63 (0.095)

The pathways identified above, including in particular, the TLR pathway, suggest that the innate immunity response are involved in responding to acute ischemic stroke at an early stage.

Result B. Analysis of stroke over time data verified the change in the TLR pathway and the identification of the CTLA pathway. INGENUITY® pathway analysis validated the following cononical pathways as likely to involve the 9-gene biomarker panel of the invention:

Gene expression over time: genes 2 fold and $p<0.05$ different between baseline and follow up: IL8, LY96, SDPR Ingenuity pathway analysis data:
Ephrin receptor signaling 8.5E-04; 14/198 (0.071)
Dopamine receptor signaling 1.95E-03; 8/93 (0.086)
CTLA4 signaling in cytotoxic T lymphocytes 2.44E-03; 9/100 (0.09)
P70S6K signaling 1.39E-02; 9/133 (0.068)
Regulation of actin-based motility by Rho 1.59E-02; 7/92 (0.076)

The pathways identified above, including in particular, the CTLA4 pathway, suggest that the cell-mediated immune response is involved in responding to acute ischemic stroke at a later stage.

The use of INGENUITY®'s IPA software is well-known in the art. Reference can be made, for example, to the following publications which cite to the use of IPA software:

"Mining knowledge and data to discover intelligent molecular biomarkers: Prostate cancer i-Biomarkers." Soft Computing Applications (SOFA), 2010 4th International Workshop on. Pages: 113-118. 15-17 Jul. 2010. Floares, A.; Balacescu, O.; Floares, C.; Balacescu, L.; Popa, T.; Vermesan, O.; Dept. of Artificial Intell., SAIA & OncoPredict, Cluj-Napoca, Romania.;

"Exploration of a genomic expression and pathway analysis approach to neurocognitive performance: preliminary findings." Neurobehavioral HIV Medicine. July 2010, Volume 2010:2 Pages 23-32. Chad A Bousman, Gursharan Chana, Stephen J Glatt, Sharon D Chandler, Todd May, James Lohr, Ian P Everall, William S Kremen, Ming T Tsuang;

"Comparison of the performance of two affinity depletion spin filters for quantitative proteomics of CSF: Evaluation of sensitivity and reproducibility of CSF analysis using GeLC-MS/MS and spectral counting." PROTEOMICS—Clinical Applications. Volume 4, Issue 6-7, pages 613-617. July 2010. Silvina A. Fratantoni, Sander R. Piersma, Connie R. Jimenez;

"Transcriptome profiling and network analysis of genetically hypertensive mice identifies potential pharmacological targets of hypertension." Physiol Genomics. 2010 Jun. 29. [Epub ahead of print] Puig O, Wang I M, Cheng P, Zhou P, Roy S, Cully D, Peters M A, Benita Y, Thompson J, Cai T Q;

"Osteosarcoma is characterised by reduced expression of markers of osteoclastogenesis and antigen presentation compared with normal bone." Br J. Cancer. 2010 Jun. 29; 103(1):73-81. Epub 2010 Jun. 15. Endo-Munoz L, Cumming A, Sommerville S, Dickinson I, Saunders N A; and "P-225 Specific gene expression in human cumulus cells according to oocyte nuclear maturation stages under in vivo maturation: clinical applications." Human Reproduction. 2010 25(Supplement 1):1170-i210. G. Ouandaogo, S. Assou, D. Haouzi, A. Ferrieres, T. Anahory, J. De Vos and S. Hamamah; and "Transcript abundance patterns in Kawasaki disease patients with intravenous immunoglobulin resistance." Hum Immunol. 2010 Jun. 20. Fury W, Tremoulet A H, Watson V E, Best B A, Shimizu C, Hamilton J, Kanegaye J T, Wei Y, Kao C, Mellis S, Lin C, Burns J C; each of which are incorporated herein by reference.

REFERENCES

The following references are incorporated herein by reference and may be cited to as further background support of this specification.
1. Thom T, Haase N, Rosamond W, Howard V J, Rumsfeld J, Manolio T, Zheng Z J, Flegal K, O'Donnell C, Kittner S, Lloyd-Jones D, Goff D C, Jr., Hong Y, Adams R, Friday G, Furie K, Gorelick P, Kissela B, Marler J, Meigs J, Roger V, Sidney S, Sorlie P, Steinberger J, Wasserthiel-Smoller S, Wilson M, Wolf P. Heart disease and stroke statistics—2006 update: A report from the american heart association statistics committee and stroke statistics subcommittee. Circulation. 2006; 113:e85-151
2. McKay J, Mensah G A, ebrary Inc. The atlas of heart disease and stroke. Geneva: World Health Organization; 2005.
3. Kim D, Liebeskind D S. Neuroimaging advances and the transformation of acute stroke care. Semin Neurol. 2005; 25:345-361
4. Hemmen T M, Meyer B C, McClean T L, Lyden P D. Identification of nonischemic stroke mimics among 411 code strokes at the University of California, San Diego, stroke center. J Stroke Cerebrovasc Dis. 2008; 17:23-25
5. Tajouri L, Fernandez F, Griffiths L R. Gene expression studies in multiple sclerosis. Curr Genomics. 2007; 8:181-189
6. Scherzer C R, Eklund A C, Morse L J, Liao Z, Locascio J J, Fefer D, Schwarzschild M A, Schlossmacher M G, Hauser M A, Vance J M, Sudarsky L R, Standaert D G, Growdon J H, Jensen R V, Gullans S R. Molecular markers of early parkinson's disease based on gene expression in blood. Proc Natl Acad Sci USA. 2007; 104:955-960
7. Maes O C, Xu S, Yu B, Chertkow H M, Wang E, Schipper H M. Transcriptional profiling of alzheimer blood mononuclear cells by microarray. Neurobiol Aging. 2007; 28:1795-1809
8. Bittner M, Meltzer P, Chen Y, Jiang Y, Seftor E, Hendrix M, Radmacher M, Simon R, Yakhini Z, Ben-Dor A, Sampas N, Dougherty E, Wang E, Marincola F, Gooden C, Lueders J, Glatfelter A, Pollock P, Carpten J, Gillanders E, Leja D, Dietrich K, Beaudry C, Berens M, Alberts D, Sondak V. Molecular classification of cutaneous malignant melanoma by gene expression profiling. Nature. 2000; 406:536-540
9. Jones M H, Virtanen C, Honjoh D, Miyoshi T, Satoh Y, Okumura S, Nakagawa K, Nomura H, Ishikawa Y. Two prognostically significant subtypes of high-grade lung neuroendocrine tumours independent of small-cell and large-cell neuroendocrine carcinomas identified by gene expression profiles. Lancet. 2004; 363:775-781
10. Chang J C, Wooten E C, Tsimelzon A, Hilsenbeck S G, Gutierrez M C, Elledge R, Mohsin S, Osborne C K, Chamness G C, Allred D C, O'Connell P. Gene expression profiling for the prediction of therapeutic response to docetaxel in patients with breast cancer. Lancet. 2003; 362: 362-369
11. Grond-Ginsbach C, Hummel M, Wiest T, Horstmann S, Pfleger K, Hergenhahn M, Hollstein M, Mansmann U, Grau A J, Wagner S. Gene expression in human peripheral blood mononuclear cells upon acute ischemic stroke. J. Neurol. 2008; 255:723-731
12. Moore D F, Li H, Jeffries N, Wright V, Cooper R A, Jr., Elkahloun A, Gelderman M P, Zudaire E, Blevins G, Yu H, Goldin E, Baird A E. Using peripheral blood mononuclear cells to determine a gene expression profile of acute ischemic stroke: A pilot investigation. Circulation. 2005; 111:212-221
13. Tang Y, Xu H, Du X, Lit L, Walker W, Lu A, Ran R, Gregg J P, Reilly M, Pancioli A, Khoury J C, Sauerbeck L R, Carrozzella J A, Spilker J, Clark J, Wagner K R, Jauch E C, Chang D J, Verro P, Broderick J P, Sharp F R. Gene expression in blood changes rapidly in neutrophils and monocytes after ischemic stroke in humans: A microarray study. J Cereb Blood Flow Metab. 2006; 26:1089-1102
14. Sharp F R, Xu H, Lit L, Walker W, Pinter J, Apperson M, Verro P. Genomic profiles of stroke in blood. Stroke. 2007; 38:691-693
15. Kidwell C S, Warach S. Acute ischemic cerebrovascular syndrome: Diagnostic criteria. Stroke. 2003; 34:2995-2998
16. D., N C. Expression profiling of whole blood specimens on illumina beadchips. Expression analysis tech note; www.Expressionanalysis.Com. October 2007
17. Amplification efficiency of taqman gene expression assays, www3.Appliedbiosystems.Com, stock#127ap05-03
18. Livak K J, Schmittgen T D. Analysis of relative gene expression data using real-time quantitative per and the 2(-delta delta c(t)) method. Methods. 2001; 25:402-408

19. Laskowitz D T, Kasner S E, Saver J, Remmel K S, Jauch E C. Clinical usefulness of a biomarkerbased diagnostic test for acute stroke: The biomarker rapid assessment in ischemic injury (brain) study. Stroke. 2009; 40:77-85
20. Barr T L, Latour L L, Lee K Y, Schaewe T J, Luby M, Chang G S, El-Zammar Z, Alam S, Hallenbeck J M, Kidwell C S, Warach S. Blood-brain barrier disruption in humans is independently associated with increased matrix metalloproteinase-9. Stroke. 2009
21. Brea D, Sobrino T, Blanco M, Cristobo I, Rodriguez-Gonzalez R, Rodriguez-Yanez M, Moldes O, Agulla J, Leira R, Castillo J. Temporal profile and clinical significance of serum neuronspecific enolase and s100 in ischemic and hemorrhagic stroke. Clin Chem Lab Med. 2009; 47:1513-1518
22. Fernandez E J, Lolis E. Structure, function, and inhibition of chemokines Annu Rev Pharmacol Toxicol. 2002; 42:469-499
23. Mines M, Ding Y, Fan G H. The many roles of chemokine receptors in neurodegenerative disorders: Emerging new therapeutical strategies. Curr Med. Chem. 2007; 14:2456-2470
24. Takami S, Minami M, Katayama T, Nagata I, Namura S, Satoh M. Tak-779, a nonpeptide cc chemokine receptor antagonist, protects the brain against focal cerebral ischemia in mice. J Cereb Blood Flow Metab. 2002; 22:780-784
25. Takami S, Minami M, Nagata I, Namura S, Satoh M. Chemokine receptor antagonist peptide, viral mip-ii, protects the brain against focal cerebral ischemia in mice. J Cereb Blood Flow Metab. 2001; 21:1430-1435
26. Stamatovic S M, Shakui P, Keep R F, Moore B B, Kunkel S L, Van Rooijen N, Andjelkovic A V. Monocyte chemoattractant protein-1 regulation of blood-brain barrier permeability. J Cereb Blood Flow Metab. 2005; 25:593-606
27. Ceradini D J, Kulkarni A R, Callaghan M J, Tepper O M, Bastidas N, Kleinman M E, Capla J M, Galiano R D, Levine J P, Gurtner G C. Progenitor cell trafficking is regulated by hypoxic gradients through hif-1 induction of sdf-1. Nat. Med. 2004; 10:858-864
28. Yamaguchi J, Kusano K F, Masuo O, Kawamoto A, Silver M, Murasawa S, Bosch-Marce M, Masuda H, Losordo D W, Isner J M, Asahara T. Stromal cell-derived factor-1 effects on ex vivo expanded endothelial progenitor cell recruitment for ischemic neovascularization. Circulation. 2003; 107:1322-1328
29. Offner H, Subramanian S, Parker S M, Afentoulis M E, Vandenbark A A, Hurn P D. Experimental stroke induces massive, rapid activation of the peripheral immune system. J Cereb Blood Flow Metab. 2006; 26:654-665
30. Yan J, Greer J M, Etherington K, Cadigan G P, Cavanagh H, Henderson R D, O'Sullivan J D, Pandian J D, Read S J, McCombe P A. Immune activation in the peripheral blood of patients with acute ischemic stroke. J. Neuroimmunol. 2009; 206:112-117
31. Zheng P S, Wen J, Ang L C, Sheng W, Viloria-Petit A, Wang Y, Wu Y, Kerbel R S, Yang B B. Versican/pg-m g3 domain promotes tumor growth and angiogenesis. FASEB J. 2004; 18:754-756
32. Vorisek I, Hajek M, Tintera J, Nicolay K, Sykova E. Water adc, extracellular space volume, and tortuosity in the rat cortex after traumatic injury. Magn Reson Med. 2002; 48:994-1003
33. Beggah A T, Dours-Zimmermann M T, Barras F M, Brosius A, Zimmermann D R, Zurn A D. Lesion-induced differential expression and cell association of neurocan, brevican, versican v1 and v2 in the mouse dorsal root entry zone. Neuroscience. 2005; 133:749-762
34. Leonardo C C, Eakin A K, Ajmo J M, Gottschall P E. Versican and brevican are expressed with distinct pathology in neonatal hypoxic-ischemic injury. J Neurosci Res. 2008; 86:1106-1114
35. Carmichael S T, Archibeque I, Luke L, Nolan T, Momiy J, Li S. Growth-associated gene expression after stroke: Evidence for a growth-promoting region in peri-infarct cortex. Exp Neurol. 2005; 193:291-311
36. Toeda K, Nakamura K, Hirohata S, Hatipoglu O F, Demircan K, Yamawaki H, Ogawa H, Kusachi S, Shiratori Y, Ninomiya Y. Versican is induced in infiltrating monocytes in myocardial infarction. Mol Cell Biochem. 2005; 280:47-56
37. Brown M D, Sacks D B. Iqgap1 in cellular signaling: Bridging the gap. Trends Cell Biol. 2006; 16:242-249
38. Fukata M, Nakagawa M, Kaibuchi K. Roles of rho-family gtpases in cell polarisation and directional migration. Curr Opin Cell Biol. 2003; 15:590-597
39. Miao L, Calvert J W, Tang J, Parent A D, Zhang J H. Age-related rhoa expression in blood vessels of rats. Mech Ageing Dev. 2001; 122:1757-1770
40. Wojciak-Stothard B, Ridley A J. Rho gtpases and the regulation of endothelial permeability. Vascul Pharmacol. 2002; 39:187-199
41. Carbajal J M, Schaeffer R C, Jr. Rhoa inactivation enhances endothelial barrier function. Am J. Physiol. 1999; 277:C955-964
42. Hordijk P L, Anthony E, Mul F P, Rientsma R, Oomen L C, Roos D. Vascular-endothelialcadherin modulates endothelial monolayer permeability. J Cell Sci. 1999; 112 (Pt 12):1915-1923
43. Hochepied T, Berger F G, Baumann H, Libert C. Alpha (1)-acid glycoprotein: An acute phase protein with inflammatory and immunomodulating properties. Cytokine Growth Factor Rev. 2003; 14:25-34
44. Fournier T, Medjoubi N N, Porquet D. Alpha-1-acid glycoprotein. Biochim Biophys Acta. 2000; 1482:157-171
45. Marsh B J, Stevens S L, Hunter B, Stenzel-Poore M P. Inflammation and the emerging role of the toll-like receptor system in acute brain ischemia. Stroke. 2009; 40:S34-37
46. Medzhitov R. Toll-like receptors and innate immunity. Nat Rev Immunol. 2001; 1:135-145
47. Rubartelli A, Lotze M T. Inside, outside, upside down: Damage-associated molecular-pattern molecules (damps) and redox. Trends Immunol. 2007; 28:429-436
48. Bianchi M E. Damps, pamps and alarmins: All we need to know about danger. J Leukoc Biol. 2007; 81:1-5
49. Salminen A, Huuskonen J, Ojala J, Kauppinen A, Kaarniranta K, Suuronen T. Activation of innate immunity system during aging: Nf-kb signaling is the molecular culprit of inflamm-aging. Ageing Res Rev. 2008; 7:83-105
50. Csiszar A, Wang M, Lakatta E G, Ungvari Z. Inflammation and endothelial dysfunction during aging: Role of nf-kappab. J Appl Physiol. 2008; 105:1333-1341
51. Letiembre M, Hao W, Liu Y, Walter S, Mihaljevic I, Rivest S, Hartmann T, Fassbender K. Innate immune receptor expression in normal brain aging. Neuroscience. 2007; 146:248-254
52. Fulop T, Larbi A, Douziech N, Fortin C, Guerard K P, Lesur O, Khalil A, Dupuis G. Signal transduction and functional changes in neutrophils with aging. Aging Cell. 2004; 3:217-226

53. Marsh B J, Williams-Karnesky R L, Stenzel-Poore M P. Toll-like receptor signaling in endogenous neuroprotection and stroke. Neuroscience. 2009; 158:1007-1020
54. Kilic U, Kilic E, Matter C M, Bassetti C L, Hermann D M. Tlr-4 deficiency protects against focal cerebral ischemia and axotomy-induced neurodegeneration. Neurobiol Dis. 2008; 31:33-40
55. Ziegler G, Harhausen D, Schepers C, Hoffmann O, Rohr C, Prinz V, Konig J, Lehrach H, Nietfeld W, Trendelenburg G. Tlr2 has a detrimental role in mouse transient focal cerebral ischemia. Biochem Biophys Res Commun. 2007; 359:574-579
56. Caso J R, Pradillo J M, Hurtado O, Lorenzo P, Moro M A, Lizasoain I. Toll-like receptor 4 is involved in brain damage and inflammation after experimental stroke. Circulation. 2007; 115:1599-1608
57. Caso J R, Pradillo J M, Hurtado O, Leza J C, Moro M A, Lizasoain I. Toll-like receptor 4 is involved in subacute stress-induced neuroinflammation and in the worsening of experimental stroke. Stroke. 2008; 39:1314-1320
58. Yang Q W, Li J C, Lu F L, Wen A Q, Xiang J, Zhang L L, Huang Z Y, Wang J Z. Upregulated expression of toll-like receptor 4 in monocytes correlates with severity of acute cerebral infarction. J Cereb Blood Flow Metab. 2008; 28:1588-1596
59. Urra X, Cervera A, Obach V, Climent N, Planas A M, Chamorro A. Monocytes are major players in the prognosis and risk of infection after acute stroke. Stroke. 2009; 40:1262-1268
60. Thom T, Haase N, Rosamond W, Howard V J, Rumsfeld J, Manolio T, Zheng Z J, Flegal K, O'Donnell C, Kittner S, Lloyd-Jones D, Goff D C, Jr., Hong Y, Adams R, Friday G, Furie K, Gorelick P, Kissela B, Marler J, Meigs J, Roger V, Sidney S, Sorlie P, Steinberger J, Wasserthiel-Smoller S, Wilson M, Wolf P. Heart disease and stroke statistics—2006 update: A report from the american heart association statistics committee and stroke statistics subcommittee. Circulation. 2006; 113:e85-151
61. McKay J, Mensah G A, ebrary Inc. The atlas of heart disease and stroke. Geneva: World Health Organization; 2005.
62. Chalela J A, Kidwell C S, Nentwich L M, Luby M, Butman J A, Demchuk A M, Hill M D, Patronas N, Latour L, Warach S. Magnetic resonance imaging and computed tomography in emergency assessment of patients with suspected acute stroke: A prospective comparison. Lancet. 2007; 369:293-298
63. Rosamond W, Flegal K, Furie K, Go A, Greenlund K, Haase N, Hailpern S M, Ho M, Howard V, Kissela B, Kittner S, Lloyd-Jones D, McDermott M, Meigs J, Moy C, Nichol G, O'Donnell C, Roger V, Sorlie P, Steinberger J, Thom T, Wilson M, Hong Y. Heart disease and stroke statistics—2008 update: A report from the american heart association statistics committee and stroke statistics subcommittee. Circulation. 2008; 117:e25-146
64. Reeves M J, Arora S, Broderick J P, Frankel M, Heinrich J P, Hickenbottom S, Karp H, LaBresh K A, Malarcher A, Mensah G, Moomaw C J, Schwamm L, Weiss P. Acute stroke care in the us: Results from 4 pilot prototypes of the paul coverdell national acute stroke registry. Stroke. 2005; 36:1232-1240
65. Barr T L, Conley Y P, Dillman A, Ding J, Warach S, Singleton A, Matarin M. Gene expression profiling in human acute ischemic stroke. University of Pittsburgh School of Nursing. 2009; PhD:270
66. Tang Y, Xu H, Du X, Lit L, Walker W, Lu A, Ran R, Gregg J P, Reilly M, Pancioli A, Khoury J C, Sauerbeck L R, Carrozzella J A, Spilker J, Clark J, Wagner K R, Jauch E C, Chang D J, Verro P, Broderick J P, Sharp F R. Gene expression in blood changes rapidly in neutrophils and monocytes after ischemic stroke in humans: A microarray study. J Cereb Blood Flow Metab. 2006; 26:1089-1102
67. Basso G, Case C, Dell'Orto M. Diagnosis and genetic subtypes of leukemia combining gene expression and flow cytometry. Blood Cells, Molecules, and Diseases. 2007; 39:164-168
68. Andersson A, Ritz C, Lindgren D, Eden P, Lassen C, Heldrup J, Olofsson T, Rade J, Fontes M, Porwit-MacDonald A, Behrendtz M, Hoglund M, Johansson B, Fioretos T. Microarray-based classification of a consecutive series of 121 childhood acute leukemias: Prediction of leukeminc and genetic subtype as well as of minimal residual disease status. Leukemia 2007; 21:1198-1203
69. Cardoso F, Van't-Verr L, Rutgers E, Loi S, Mook S, Piccart-Gebhart M. Clinical application of the 70-gene profile: The mindact trial. Journal of Clinical Oncology. 2008; 26:729-735
70. Sharp F R, Xu H, Lit L, Walker W, Apperson M, Gilbert D L, Glauser T A, Wong B, Hershey A, Liu D Z, Pinter J, Zhan X, Liu X, Ran R. The future of genomic profiling of neurological diseases using blood. Arch Neurol. 2006; 63:1529-1536
71. Whiteley W, Tseng M C, Sandercock P. Blood biomarkers in the diagnosis of ischemic stroke. A systematic review. Stroke. 2008
72. Montaner J, Perea-Gainza M, Delgado P, Ribo M, Chacon P, Rosell A, Quintana M, Palacios M E, Molina C A, Alvarez-Sabin J. Etiologic diagnosis of ischemic stroke subtypes with plasma biomarkers. Stroke. 2008; 39:2280-2287
73. Stone G P, Mernaugh R, Haselton F R. Virus detection using filament-coupled antibodies. Biotechnol Bioeng. 2005; 91:699-706
74. Kidwell C S, Warach S. Acute ischemic cerebrovascular syndrome: Diagnostic criteria. Stroke. 2003; 34:2995-2998
75. Easton J D, Saver J L, Albers G W, Alberts M J, Chaturvedi S, Feldmann E, Hatsukami T S, Higashida R T, Johnston S C, Kidwell C S, Lutsep H L, Miller E, Sacco R L. Definition and evaluation of transient ischemic attack: A scientific statement for healthcare professionals from the american heart association/american stroke association stroke council; council on cardiovascular surgery and anesthesia; council on cardiovascular radiology and intervention; council on cardiovascular nursing; and the interdisciplinary council on peripheral vascular disease. The american academy of neurology affirms the value of this statement as an educational tool for neurologists. Stroke. 2009; 40:2276-2293
76. Meschia J F, Lojacono M A, Miller M J, Brott T G, Atkinson E J, O'Brien P C. Reliability of the questionnaire for verifying stroke-free status. Cerebrovasc Dis. 2004; 17:218-223
77. Griffiths R A, Good W R, Watson N P, O'Donnell H F, Fell P J, Shakespeare J M. Normal erythrocyte sedimentation rate in the elderly. Br Med J (Clin Res Ed). 1984; 289:724-725
78. Bonita R, Beaglehole R. Recovery of motor function after stroke. Stroke. 1988; 19:1497-1500
79. Mahoney F I, Barthel D W. Functional evaluation: The barthel index. Md State Med J. 1965; 14:61-65
80. Wilson J T, Pettigrew L E, Teasdale G M. Structured interviews for the glasgow outcome scale and the extended glasgow outcome scale: Guidelines for their use. J. Neurotrauma. 1998; 15:573-585
81. Spertus J A, Winder J A, Dewhurst T A, Deyo R A, Prodzinski J, McDonell M, Fihn S D. Development and evaluation of the seattle angina questionnaire: A new functional status measure for coronary artery disease. J Am Coll Cardiol. 1995; 25:333-341

82. Bushel P R, Wolfinger R D, Gibson G. Simultaneous clustering of gene expression data with clinical chemistry and pathological evaluations reveals phenotypic prototypes. *BMC Syst Biol.* 2007; 1:15
83. Perez J M, Hasleton, F. R., Wright, Dr. W. Viral detection using DNA functionalized gold filaments. *The Analyst.* 2009; 134, 1548-1553.
84. Tsourkas A, Behlke M A, Rose S D, Bao G. Hybridization kinetics and thermodynamics of molecular beacons. *Nucleic Acids Res.* 2003; 31:1319-1330
85. Bonnet G, Tyagi S, Libchaber A, Kramer F R. Thermodynamic basis of the enhanced specificity of structured DNA probes. *Proc Natl Acad Sci USA.* 1999; 96:6171-6176

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for the diagnosis of acute ischemic stroke in a subject, comprising
obtaining a biological sample from a subject;
extracting total RNA from the sample; and
determining expression by biomarker-specific antibody immunoassay of a panel of only 4, 5, 6, 7, 8, 9, 10, 15 or 20 individual biomarkers in the sample obtained from the subject, wherein four of said individual biomarkers are:
(a) chemokine receptor 7 (CCR7);
(b) chondroitin sulfate proteoglycan 2 (CSPG2);
(c) IQ motif-containing GTPase activation protein 1 (IQGAP1); and
(d) orosomucoid 1 (ORM1),
wherein expression of the biomarkers indicates acute ischemic stroke in the subject.

2. A method for the diagnosis of acute ischemic stroke in a subject, comprising:
obtaining a biological sample from a subject;
extracting total RNA from the sample; and
determining expression by filament-based immunoassay of a panel of only 9, 10, 15 or 20 individual biomarkers in the sample obtained from the subject, wherein nine of said individual biomarkers are:
(a) chemokine receptor 7 (CCR7);
(b) chondroitin sulfate proteoglycan 2 (CSPG2);
(c) IQ motif-containing GTPase activation protein 1 (IQGAP1);
(d) orosomucoid 1 (ORM1);
(e) arginase 1 (ARG1);
(f) lymphocyte antigen 96 (LY96);
(g) matrix metalloproteinase 9 (MMP9);
(h) carbonic anhydrase 4 (CA4); and
(i) s100 calcium binding protein A12 (s100A12),
wherein expression of the biomarkers indicates acute ischemic stroke in the subject.

3. A method for the diagnosis of acute ischemic stroke in a subject, comprising
obtaining a biological sample from a subject;
extracting total RNA from the sample; and
determining expression by filament-based immunoassay of a panel of only the following five individual biomarkers in the sample obtained from the subject:

(a) arginase 1 (ARG1);
(b) carbonic anhydrase 4 (CA4);
(c) lymphocyte antigen 96 (LY96);
(d) matrix metalloproteinase 9 (MMP9); and
(e) s100 calcium binding protein A12 (s100A12), wherein expression of the biomarkers indicates acute ischemic stroke in the subject.

4. The method of claim 1, 2 or 3, wherein the sample is whole peripheral blood obtained from the subject.

5. The method of claim 1, 2 or 3, wherein the method is executed on the subject no more than 3 hours after onset of presenting acute ischemic stroke symptoms.

6. The method of claim 1, 2 or 3, wherein the method is executed on the subject no more than 4.5 hours after onset of presenting acute ischemic stroke symptoms.

7. The method according to claim 1, 2 or 3, further comprising obtaining brain imaging data of the subject and evaluating the data to detect an acute ischemic stroke.

8. The method according to claim 7, wherein the brain imaging data is obtained by MRI.

9. The method according to claim 7, wherein the brain imaging data is obtained by computerized tomography (CT) scan.

10. The method according to claim 1, 2 or 3, further comprising treating the subject with a stroke therapy if the subject is diagnosed with an acute ischemic stroke.

11. The method according to claim 10, wherein the stroke therapy is the administration of a therapeutically effective amount of recombinant plasminogen activator (rtPA).

12. The method according to claim 1, 2 or 3, wherein at least one biomarker is determined to have at least a 1.5 fold increase or decrease in expression level as compared to the levels of the biomarker in a non-stroke subject.

13. The method according to claim 1, 2 or 3, wherein at least one biomarker is determined to have at least a 2.0 fold increase or decrease in expression level as compared to the levels of the biomarker in a non-stroke subject.

14. A method for differentiating an acute ischemic stroke from a transient ischemic attack (TIA), a hemorrhagic stroke or a stroke mimic in a subject presenting symptoms characteristic of a stroke, comprising:
(a) obtaining a biological sample from the patient;
(b) contacting the biological sample with a an antibody or a nucleic acid capable of detecting the presence of a panel of only 4, 5, 6, 7, 8, or 9 individual biomarkers, wherein said panel of individual biomarkers comprises: chemokine receptor 7 (CCR7); chondroitin sulfate proteoglycan 2 (CSPG2); IQ motif—containing GTPase activation protein 1 (IQGAP1); and orosomucoid 1 (ORM1), wherein the presence of the biomarkers in the biological sample is indicative of an acute ischemic stroke but not indicative of a transient ischemic attack (TIAs), hemorrhagic stroke or stroke mimic, and
(c) administering an effective amount of recombinant plasminogen activator (rtPA) if the subject is diagnosed with an acute ischemic stroke.

15. The method of claim 14, wherein the detection means is further capable of detecting the presence of at least one additional biomarker selected from the group consisting of: arginase 1 (ARG1); lymphocyte antigen 96 (LY96); matrix metalloproteinase 9 (MMP9); carbonic anhydrase 4 (CA4); and s100 calcium binding protein A12 (s100A12).

16. A method for differentiating an acute ischemic stroke from a transient ischemic attack (TIA), a hemorrhagic stroke and a stroke mimic in a subject presenting symptoms characteristic of a stroke, comprising:
(a) obtaining a biological sample from the patient;
(b) contacting the biological sample with a monoclonal antibody or a nucleic acid capable of detecting the presence of a panel of only 9, 10, 15 or 20 individual biomarkers, wherein said panel of individual biomarkers comprises: (i) chemokine receptor 7 (CCR7); (ii) chondroitin sulfate proteoglycan 2 (CSPG2); (iii) IQ motif-containing GTPase activation protein 1 (IQGAP1); (iv) orosomucoid 1 (ORM1); (v) arginase 1 (ARG1); (vi) lymphocyte antigen 96 (LY96); (vii) matrix metalloproteinase 9 (MMP9); (viii) carbonic anhydrase 4 (CA4); and (ix) s100 calcium binding protein A12 (s100A12), wherein the presence of the biomarkers in the biological sample is indicative of an acute ischemic stroke but not indicative of a transient ischemic attack (TIAs), hemorrhagic stroke or stroke mimic, and
(c) administering an effective amount of recombinant plasminogen activator (rtPA) if the subject is diagnosed with an acute ischemic stroke.

17. The method of claim 14 or 16, wherein the sample is whole peripheral blood obtained from the subject.

18. The method of claim 14 or 16, wherein the method is executed on the subject no more than 3 hours after onset of the presenting of the stroke symptoms.

19. The method of claim 14 or 16, wherein the method is executed on the subject no more than 4.5 hours after onset of the presenting of the stroke symptoms.

20. The method of claim 14 or 16, wherein at least one biomarker is a nucleic acid molecule.

21. The method of claim 20, wherein the nucleic acid molecule is mRNA.

22. The method of claim 14 or 16, wherein the detection means is an oligonucleotide probe.

23. The method of claim 14 or 16, further comprising obtaining brain imaging data of the subject and evaluating the data to detect an acute ischemic stroke.

24. The method according to claim 23, wherein the brain imaging data is obtained by MRI.

25. The method according to claim 23, wherein the brain imaging data is obtained by computerized tomography (CT) scan.

26. The method of claim 14 or 16, wherein at least one bio marker detected by the detection means has at least a 1.5 fold increase or decrease in expression level as compared to the levels of the bio marker in a non-stroke subject.

27. The method of claim 14 or 16, wherein at least one biomarker detected by the detection means has at least a 2.0 fold increase or decrease in expression level as compared to the levels of the biomarker in a non-stroke subject.

* * * * *

SEQUENCE LISTING

```
<160> NUMBER OF SEQ ID NOS: 19

<210> SEQ ID NO 1
<211> LENGTH: 2188
<212> TYPE: DNA
<213> ORGANISM: Homo sapiens

<400> SEQUENCE: 1 agacagggt  agtgcgaggc  cgggcacagc  cttcctgtgt  ggttttaccg  cccagagagc      60
gtcatggacc  tggggaaacc  aatgaaaagc  gtgctggtgg  tggctctcct  tgtcattttc     120
caggtatgcc  tgtgtcaaga  tgaggtcacg  gacgattaca  tcggagacaa  caccacagtg     180
gactacactt  tgttcgagtc  tttgtgctcc  aagaaggacg  tgcggaactt  taaagcctgg     240
ttcctcccta  tcatgtactc  catcatttgt  ttcgtgggcc  tactgggcaa  tgggctggtc     300
gtgttgacct  atatctattt  caagaggctc  aagaccatga  ccgatacccta  cctgctcaac     360 ctggcggtgg  cagacatcct  cttcctcctg  acccttccct  tctgggccta  cagcgcggcc     420
aagtcctggg  tcttcggtgt  ccacttttgc  aagctcatct  ttgccatcta  caagatgagc     480
ttcttcagtg  gcatgctcct  acttctttgc  atcagcattg  accgctacgt  ggccatcgtc     540
caggctgtct  cagctcaccg  ccaccgtgcc  cgcgtccttc  tcatcagcaa  gctgtcctgt     600
gtgggcatct  ggatactagc  cacagtgctc  tccatcccag  agctcctgta  cagtgacctc     660
cagaggagca  gcagtgagca  agcgatgcga  tgctctctca  tcacagagca  tgtggaggcc     720
tttatcacca  tccaggtggc  ccagatggtg  atcggctttc  tggtcccccct  gctggccatg     780 agcttctgtt  accttgtcat  catccgcacc  ctgctccagg  cacgcaactt  tgagcgcaac     840
aaggccatca  aggtgatcat  cgctgtggtc  gtggtcttca  tagtcttcca  gctgccctac     900
aatggggtgg  tcctggccca  gacggtggcc  aacttcaaca  tcaccagtag  cacctgtgag     960
ctcagtaagc  aactcaacat  cgcctacgac  gtcacctaca  gcctggcctg  cgtccgctgc    1020
tgcgtcaacc  ctttcttgta  cgccttcatc  ggcgtcaagt  tccgcaacga  tctcttcaag    1080
ctcttcaagg  acctgggctg  cctcagccag  gagcagctcc  ggcagtggtc  ttcctgtcgg    1140
cacatccggc  gctcctccat  gagtgtggag  gccgagacca  ccaccacctt  ctccccatag    1200
gcgactcttc  tgcctggact  agagggacct  ctcccagggt  ccctgggtg   gggatagga    1260 gcagatgcaa  tgactcagga  catcccccg   ccaaaagctg  ctcagggaaa  agcagctctc    1320
ccctcagagt  gcaagcccct  gctccagaag  atagcttcac  cccaatccca  gctacctcaa    1380
ccaatgccaa  aaaaagacag  ggctgataag  ctaacaccag  acagacaaca  ctgggaaaca    1440
gaggctattg  tcccctaaac  caaaaactga  aagtgaaagt  ccagaaactg  ttcccacctg    1500
ctggagtgaa  ggggccaagg  agggtgagtg  caagggcgt  gggagtggcc  tgaagagtcc    1560
tctgaatgaa  ccttctggcc  tcccacagac  tcaaatgctc  agaccagctc  ttccgaaaac    1620
caggccttat  ctccaagacc  agagatagtg  gggagacttc  ttggcttggt  gaggaaaagc    1680
```

-continued

```
ggacatcagc tggtcaaaca aactctctga acccctccct ccatcgtttt cttcactgtc      1740
ctccaagcca gcgggaatgg cagctgccac gccgccctaa aagcacactc atcccctcac      1800
ttgccgcgtc gccctcccag gctctcaaca ggggagagtg tggtgtttcc tgcaggccag      1860
gccagctgcc tccgcgtgat caaagccaca ctctgggctc cagagtgggg atgacatgca      1920
ctcagctctt ggctccactg ggatgggagg agaggacaag ggaaatgtca ggggcgggga      1980
gggtgacagt ggccgcccaa ggcccacgag cttgttcttt gttctttgtc acagggactg      2040
aaaacctctc ctcatgttct gctttcgatt cgttaagaga gcaacatttt acccacacac      2100
agataaagtt ttcccttgag gaacaacag ctttaaagaa aaagaaaaa aaaagtcttt        2160 ggtaaatggc aaaaaaaaa aaaaaaa                                          2188
```

<210> SEQ ID NO 2
<211> LENGTH: 378
<212> TYPE: PRT
<213> ORGANISM: Homo sapiens

<400> SEQUENCE: 2

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Arg Thr Leu Leu Gln Ala Arg Asn Phe
                245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
        275                 280                 285
```

```
Ala Asn Phe Asn Ile Thr Ser Ser Thr Cys Glu Leu Ser Lys Gln Leu
        290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
        370                 375

<210> SEQ ID NO 3
<211> LENGTH: 11185
<212> TYPE: DNA
<213> ORGANISM: Homo sapiens

<400> SEQUENCE: 3
gctgccccga gcctttctgg ggaagaactc caggcgtgcg gacgcaacag ccgagaacat      60
taggtgttgt ggacaggagc tgggaccaag atcttcggcc agccccgcat cctcccgcat     120
cttccagcac cgtcccgcac cctccgcatc cttcccgggg ccaccacgct tcctatgtga     180
cccgcctggg caacgccgaa cccagtcgcg cagcgctgca gtgaattttc cccccaaact     240
gcaataagcc gccttccaag gccaagatgt tcataaatat aaagagcatc ttatggatgt     300
gttcaacctt aatagtaacc catgcgctac ataaagtcaa agtgggaaaa agcccaccgg     360
tgaggggctc cctctctgga aaagtcagcc taccttgtca ttttcaacg atgcctactt     420 tgccacccag ttacaacacc agtgaatttc tccgcatcaa atggtctaag attgaagtgg     480
acaaaaatgg aaaagatttg aaagagacta ctgtccttgt ggcccaaaat ggaaatatca     540
agattggtca ggactacaaa gggagagtgt ctgtgcccac acatcccgag ctgtgggcg      600 atgcctccct cactgtggtc aagctgctgg caagtgatgc gggtctttac cgctgtgacg     660
tcatgtacgg gattgaagac acacaagaca cggtgtcact gactgtggat ggggttgtgt     720 tcactacag gcggcaacc agcaggtaca cactgaattt tgaggctgct cagaaggctt     780
gtttggacgt tggggcagtc atagcaactc agagcagct ctttgctgcc tatgaagatg      840
gatttgagca gtgtgacgca ggctggctgg ctgatcagac tgtcagatat cccatccggg     900
ctcccagagt aggctgttat ggagataaga tgggaaaggc aggagtcagg acttatggat     960
tccgttctcc ccaggaaact tacgatgtgt attgttatgt ggatcatctg atggtgatg      1020 tgttccacct cactgtcccc agtaaattca ccttcgagga ggctgcaaaa gagtgtgaaa    1080
accaggatgc caggctggca acagtggggg aactccaggc ggcatggagg aacggctttg    1140
accagtgcga ttacgggtgg ctgtcggatg ccagcgtgcg ccaccctgtg actgtggcca    1200
gggcccagtg tggaggtggt ctacttgggg tgagaacct gtatcgtttt gagaaccaga     1260
caggcttccc tccccctgat agcagatttg atgcctactg ctttaaacct aaagaggcta    1320
caaccatcga tttgagtatc ctcgcagaaa ctgcatcacc cagtttatcc aaagaaccac    1380
aaatggtttc tgatagaact acaccaatca tccctttagt tgatgaatta cctgtcattc    1440
caacagagtt ccctcccgtg ggaaatattg tcagttttga acagaaagcc acagtccaac    1500
ctcaggctat cacagatagt ttagccacca aattacccac acctactggc agtaccaaga    1560
```

```
agccctggga tatggatgac tactcacctt ctgcttcagg acctcttgga aagctagaca   1620
tatcagaaat taaggaagaa gtgctccaga gtacaactgg cgtctctcat tatgctacgg   1680
attcatggga tggtgtcgtg aagataaac  aaacacaaga atcggttaca cagattgaac   1740
aaatagaagt gggtcctttg gtaacatcta tggaaatctt aaagcacatt ccttccaagg   1800
aattccctgt aactgaaaca ccattggtaa ctgcaagaat gatcctggaa tccaaaactg   1860
aaaagaaaat ggtaagcact gtttctgaat tggtaaccac aggtcactat ggattcacct   1920
tgggagaaga ggatgatgaa gacagaacac ttacagttgg atctgatgag agcaccttga   1980
tctttgacca aattcctgaa gtcattacgg tgtcaaagac ttcagaagac accatccaca   2040
ctcatttaga agacttggag tcagtctcag catccacaac tgtttcccct ttaattatgc   2100
ctgataataa tggatcatcc atggatgact gggaagagag acaaactagt ggtaggataa   2160
cggaagagtt tcttggcaaa tatctgtcta ctacaccttt tccatcacag catcgtacag   2220
aaatagaatt gtttccttat tctggtgata aatattagt  agagggaatt tccacagtta   2280
tttatccttc tctacaaaca gaaatgacac atagaagaga agaacagaa  acactaatac   2340 cagagatgag aacagatact tatacagatg aaatacaaga agagatcact aaaagtccat   2400
ttatgggaaa aacagaagaa gaagtcttct ctgggatgaa actctctaca tctctctcag   2460
agccaattca tgttacagag tcttctgtgg aaatgaccaa gtcttttgat ttcccaacat   2520
tgataacaaa gttaagtgca gagccaacag aagtaagaga tatggaggaa gactttacag   2580
caactccagg tactacaaaa tatgatgaaa atattacaac agtgcttttg gcccatggta   2640
ctttaagtgt tgaagcagcc actgtatcaa atggtcatg  ggatgaagat aatcaaacat   2700
ccaagccttt agagtctaca gaaccttcag cctcttcaaa attgccccct gccttactca   2760
caactgtggg gatgaatgga aaggataaag acatcccaag tttcactgaa gatggagcag   2820
atgaatttac tcttattcca gatagtactc aaaagcagtt agaggaggtt actgatgaag   2880
acatagcagc ccatggaaaa ttcacaatta gatttcagcc aactcatca  actggtattg   2940 cagaaaagtc aactttgaga gattctacaa ctgaagaaaa agttccacct atcacaagca   3000
ctgaaggcca gtttatgca  accatggaag gaagtgcttt gggtgaagta gaagatgtgg   3060
acctctctaa gccagtatct actgttcccc aatttgcaca cacttcagag gtggaaggat   3120
tagcatttgt tagttatagt agcacccaag agcctactac ttatgtagac tcttcccata   3180
ccattcctct ttctgtaatt cccaagacag actggggagt gttagtacct tctgttccat   3240
cagaagatga agttctaggt gaaccctctc aagacatact tgtcattgat cagactcgcc   3300
ttgaagcgac tatttctcca gaaactatga gaacaacaaa aatcacagag ggaacaactc   3360
aggaagaatt cccttgggaaa gaacagactg cagagaaacc agttcctgct ctcagttcta   3420
cagcttggac tcccaaggag gcagtaacac cactggatga acaagagggc gatggatcag   3480
catatacagt ctctgaagat gaattgttga caggttctga gagggtccca gttttagaaa   3540
caactccagt tggaaaaatt gatcacagtg tgtcttatcc accaggtgct gtaactgagc   3600
acaaagtgaa aacagatgaa gtggtaacac taacaccacg cattgggcca aaagtatctt   3660
taagtccagg gcctgaacaa aaatatgaaa cagaaggtag tagtacaaca ggatttacat   3720
catctttgag tccttttagt acccacatta cccagcttat ggaagaaacc actactgaga   3780
aaacatccct agaggatatt gatttaggct caggattatt tgaaaagccc aaagccacag   3840
aactcataga attttcaaca atcaaagtca cagttccaag tgatattacc actgccttca   3900
gttcagtaga cagacttcac acaacttcag cattcaagcc atcttccgcg atcactaaga   3960
```

```
aaccacctct catcgacagg gaacctggtg aagaaacaac cagtgacatg gtaatcattg    4020
gagaatcaac atctcatgtt cctcccacta cccttgaaga tattgtagcc aaggaaacag    4080
aaaccgatat tgatagagag tatttcacga cttcaagtcc tcctgctaca cagccaacaa    4140 gaccaccac tgtggaagac aaagaggcct ttggacctca ggcgctttct acgccacagc     4200
ccccagcaag cacaaaattt caccctgaca ttaatgttta tattattgag gtcagagaaa    4260
ataagacagg tcgaatgagt gatttgagtg taattggtca tccaatagat tcagaatcta    4320
aagaagatga accttgtagt gaagaaacag atccagtgca tgatctaatg gctgaaattt    4380
tacctgaatt ccctgacata attgaaatag acctatacca cagtgaagaa aatgaagaag    4440
aagaagaaga gtgtgcaaat gctactgatg tgacaaccac cccatctgtg cagtacataa    4500
atgggaagca tctcgttacc actgtgccca aggacccaga agctgcagaa gctaggcgtg    4560
gccagtttga aagtgttgca ccttctcaga atttctcgga cagctctgaa agtgatactc    4620
atccatttgt aatagccaaa acggaattgt ctactgctgt gcaacctaat gaatctacag    4680
aaacaactga gtctcttgaa gttacatgga agcctgagac ttaccctgaa acatcagaac    4740 attttttcagg tggtgagcct gatgttttcc ccacagtccc attccatgag gaatttgaaa    4800
gtggaacagc caaaaaaggg gcagaatcag tcacagagag agatactgaa gttggtcatc    4860
aggcacatga acatactgaa cctgtatctc tgtttcctga agagtcttca ggagagattg    4920
ccattgacca agaatctcag aaaatagcct ttgcaagggc tacagaagta acatttggtg    4980
aagaggtaga aaaagtact tctgtcacat acactcccac tatagttcca agttctgcat      5040
cagcatatgt ttcagaggaa gaagcagtta ccctaatagg aaatccttgg ccagatgacc    5100
tgttgtctac caaagaaagc tgggtagaag caactcctag acaagttgta gagctctcag    5160
ggagttcttc gattccaatt acagaaggct ctggagaagc agaagaagat gaagatacaa    5220
tgttcaccat ggtaactgat ttatcacaga gaaatactac tgatacactc attactttag    5280
acactagcag gataatcaca gaaagctttt ttgaggttcc tgcaaccacc atttatccag    5340
tttctgaaca accttctgca aaagtggtgc ctaccaagtt tgtaagtgaa acagacactt    5400
ctgagtggat ttccagtacc actgttgagg aaaagaaaag gaaggaggag gagggaacta    5460
caggtacggc ttctacattt gaggtatatt catctacaca gagatcggat caattaattt    5520
taccctttga attagaaagt ccaaatgtag ctacatctag tgattcaggt accaggaaaa    5580
gttttatgtc cttgacaaca ccaacacagt ctgaaaggga aatgacagat tctactcctg    5640
tctttacaga aacaaataca ttagaaaatt tgggggcaca gaccactgag cacagcagta    5700
tccatcaacc tgggggttcag gaagggctga ccactctccc acgtagtcct gcctctgtct    5760
ttatggagca gggctctgga gaagctgctg ccgacccaga aaccaccact gtttcttcat    5820
tttcattaaa cgtagagtat gcaattcaag ccgaaaagga agtagctggc actttgtctc    5880
cgcatgtgga aactacattc tccactgagc caacaggact ggttttgagt acagtaatgg    5940
acagagtagt tgctgaaaat ataacccaaa catccaggga aatagtgatt tcagagcgat    6000
taggagaacc aaaattatgg gcagaaataa ggggcttttc cacaggtttt cctttggagg    6060
aagatttcag tggtgacttt agagaatact caacagtgtc tcatcccata gcaaaagaag    6120
aaacggtaat gatggaaggc tctggagatg cagcatttag ggacacccag acttcaccat    6180
ctacagtacc tacttcagtt cacatcagtc acatatctga ctcagaagga cccagtagca    6240
ccatggtcag cacttcagcc ttcccctggg aagagtttac atcctcagct gagggctcag    6300
```

```
gtgagcaact ggtcacagtc agcagctctg ttgttccagt gcttcccagt gctgtgcaaa      6360
agttttctgg tacagcttcc tccattatcg acgaaggatt gggagaagtg ggtactgtca      6420
atgaaattga tagaagatcc accatttac caacagcaga agtggaaggt acgaaagctc       6480
cagtagagaa ggaggaagta aaggtcagtg gcacagtttc aacaaacttt ccccaaacta      6540
tagagccagc caaattatgg tctaggcaag aagtcaaccc tgtaagacaa gaaattgaaa      6600
gtgaaacaac atcagaggaa caaattcaag aagaaaagtc atttgaatcc cctcaaaact      6660
ctcctgcaac agaacaaaca atctttgatt cacagacatt tactgaaact gaactcaaaa      6720
ccacagatta ttctgtacta acaacaaaga aaacttacag tgatgataaa gaatgaagg      6780 aggaagacac ttctttagtt aacatgtcta ctccagatcc agatgcaaat ggcttggaat      6840
cttacacaac tctccctgaa gctactgaaa agtcacattt tttcttagct actgcattag      6900
taactgaatc tataccagct gaacatgtag tcacagattc accaatcaaa aaggaagaaa      6960
gtacaaaaca ttttccgaaa ggcatggagc caacaattca agagtcagat actgagctct      7020
tattctctgg actgggatca ggagaagaag ttttacctac tctaccaaca gagtcagtga      7080
attttactga agtggaacaa atcaataaca cattatatcc ccacacttct caagtggaaa      7140
gtacctcaag tgacaaaatt gaagacttta acagaatgga aaatgtggca aaagaagttg      7200
gaccactcgt atctcaaaca gacatctttg aaggtagtgg gtcagtaacc agcacaacat      7260
taatagaaat tttaagtgac actggagcag aaggacccac ggtggcacct ctcccttct      7320 ccacggacat cggacatcct caaaatcaga ctgtcaggtg ggcagaagaa tccagacta       7380 gtagaccaca aaccataact gaacaagact ctaacaagaa ttcttcaaca gcagaaatta      7440
acgaaacaac aacctcatct actgattttc tggctagagc ttatggtttt gaaatggcca      7500
aagaatttgt tacatcagca ccaaaaccat ctgacttgta ttatgaacct tctggagaag      7560
gatctggaga agtggatatt gttgattcat ttcacacttc tgcaactact caggcaacca      7620
gacaagaaag cagcaccaca tttgtttctg atgggtccct ggaaaaacat cctgaggtgc      7680
caagcgctaa agctgttact gctgatggat tcccaacagt ttcagtgatg ctgcctcttc      7740
attcagagca gaacaaaagc tcccctgatc caactagcac actgtcaaat acagtgtcat      7800
atgagaggtc cacagacggt agtttccaag accgtttcag ggaattcgag gattccacct      7860
taaaacctaa cagaaaaaaa cccactgaaa atattatcat agacctggac aaagaggaca      7920
aggatttaat attgacaatt acagagagta ccatccttga aattctacct gagctgacat      7980
cggataaaaa tactatcata gatattgatc atactaaacc tgtgtatgaa gacattcttg      8040
gaatgcaaac agatatagat acagaggtac catcagaacc acatgacagt aatgatgaaa      8100
gtaatgatga cagcactcaa gttcaagaga tctatgaggc agctgtcaac ctttctttaa      8160
ctgaggaaac atttgagggc tctgctgatg ttctggctag ctacactcag gcaacacatg      8220
atgaatcaat gacttatgaa gatagaagcc aactagatca catgggcttt cacttcacaa      8280
ctgggatccc tgctcctagc acagaaacag aattagacgt tttacttccc acggcaacat      8340
ccctgccaat tcctcgtaag tctgccacag ttattccaga gattgaagga ataaaagctg      8400
aagcaaaagc cctggatgac atgtttgaat caagcacttt gtctgatggt caagctattg      8460
cagaccaaag tgaaataata ccaacattgg gccaatttga aaggactcag gaggagtatg      8520
aagacaaaaa acatgctggt ccttcttttc agccagaatt ctcttcagga gctgaggagg      8580
cattagtaga ccatactccc tatctaagta ttgctactac ccaccttatg gatcagagtg      8640
taacagaggt gcctgatgtg atggaaggat ccaatccccc atattacact gatacaacat      8700
```

```
tagcagtttc aacatttgcg aagttgtctt ctcagacacc atcatctccc ctcactatct    8760
actcaggcag tgaagcctct ggacacacag agatccccca gcccagtgct ctgccaggaa    8820
tagacgtcgg ctcatctgta atgtcccac aggattcttt taaggaaatt catgtaaata    8880
ttgaagcaac tttcaaacca tcaagtgagg aataccttca cataactgag cctccctctt    8940
tatctcctga cacaaaatta gaaccttcag aagatgatgg taaacctgag ttattagaag    9000
aaatggaagc ttctcccaca gaacttattg ctgtggaagg aactgagatt ctccaagatt    9060
tccaaaacaa aaccgatggt caagtttctg gagaagcaat caagatgttt cccaccatta    9120
aaacacctga ggctggaact gttattacaa ctgccgatga aattgaatta gaaggtgcta    9180
cacagtggcc acactctact tctgcttctg ccacctatgg ggtcgaggca ggtgtggtgc    9240
cttggctaag tccacagact tctgagaggc ccacgctttc ttcttctcca gaaataaacc    9300
ctgaaactca agcagcttta atcagagggc aggattccac gatagcagca tcagaacagc    9360
aagtggcagc gagaattctt gattccaatg atcaggcaac agtaaaccct gtggaattta    9420
atactgaggt tgcaacacca ccattttccc ttctggagac ttctaatgaa acagatttcc    9480
tgattggcat taatgaagag tcagtggaag gcacggcaat ctatttacca ggacctgatc    9540
gctgcaaaat gaacccgtgc cttaacggag gcacctgtta tcctactgaa acttcctacg    9600
tatgcacctg tgtgccagga tacagcgag accagtgtga acttgatttt gatgaatgtc    9660
actctaatcc ctgtcgtaat ggagccactt gtgttgatgg ttttaacaca ttcaggtgcc    9720
tctgccttcc aagttatgtt ggtgcacttt gtgagcaaga taccgagaca tgtgactatg    9780
gctggcacaa attccaaggg cagtgctaca aatactttgc ccatcgacgc acatgggatg    9840
cagctgaacg ggaatgccgt ctgcagggtg cccatctcac aagcatcctg tctcacgaag    9900
aacaaatgtt tgttaatcgt gtgggccatg attatcagtg gataggcctc aatgacaaga    9960
tgtttgagca tgacttccgt tggactgatg gcagcacact gcaatacgag aattggagac    10020
ccaaccagcc agacagcttc ttttctgctg gagaagactg tgttgtaatc atttggcatg    10080
agaatggcca gtggaatgat gttccctgca attaccatct cacctatacg tgcaagaaag    10140
gaacagttgc ttgcggccag ccccctgttg tagaaaatgc caagaccttt ggaaagatga    10200
aacctcgtta tgaaatcaac tccctgatta gataccactg caaagatggt ttcattcaac    10260
gtcaccttcc aactatccgg tgcttaggaa atggaagatg ggctatacct aaaattacct    10320
gcatgaaccc atctgcatac caaaggactt attctatgaa atactttaaa aattcctcat    10380
cagcaaagga caattcaata aatacatcca aacatgatca tcgttggagc cggaggtggc    10440
aggagtcgag gcgctgatcc ctaaaatggc gaacatgtgt tttcatcatt tcagccaaag    10500
tcctaacttc ctgtgccttt cctatcacct cgagaagtaa ttatcagttg gtttggattt    10560
ttggaccacc gttcagtcat tttgggttgc cgtgctccca aaacatttta aatgaaagta    10620
ttggcattca aaaagacagc agacaaaatg aagaaaatg agagcagaaa gtaagcattt    10680
ccagcctatc taatttcttt agttttctat ttgcctccag tgcagtccat ttcctaatgt    10740
ataccagcct actgtactat ttaaaatgct caatttcagc accgatggcc atgtaaataa    10800
gatgatttaa tgttgatttt aatcctgtat ataaataaa aagtcacaat gagtttgggc    10860
atatttaatg atgattatgg agccttagag gtctttaatc attggttcgg ctgcttttat    10920
gtagtttagg ctgaaatgg tttcacttgc tctttgactg tcagcaagac tgaagatggc    10980
ttttcctgga cagctagaaa acacaaaatc ttgtaggtca ttgcacctat ctcagccata    11040
```

```
ggtgcagttt gcttctacat gatgctaaag gctgcgaatg ggatcctgat ggaactaagg    11100
actccaatgt cgaactcttc tttgctgcat tccttttct tcacttacaa gaaaggcctg     11160
aatggaggac ttttctgtaa ccagg                                          11185
```

<210> SEQ ID NO 4
<211> LENGTH: 3376
<212> TYPE: PRT
<213> ORGANISM: Homo sapiens

<400> SEQUENCE: 4

```
Leu His Lys Val Lys Val Gly Lys Ser Pro Val Arg Gly Ser Leu
1               5                   10                  15

Ser Gly Lys Val Ser Leu Pro Cys His Phe Ser Thr Met Pro Thr Leu
                20                  25                  30

Pro Pro Ser Tyr Asn Thr Ser Glu Phe Leu Arg Ile Lys Trp Ser Lys
            35                  40                  45

Ile Glu Val Asp Lys Asn Gly Lys Asp Leu Lys Glu Thr Thr Val Leu
50                  55                  60

Val Ala Gln Asn Gly Asn Ile Lys Ile Gly Gln Asp Tyr Lys Gly Arg
65                  70                  75                  80

Val Ser Val Pro Thr His Pro Glu Ala Val Gly Asp Ala Ser Leu Thr
                85                  90                  95

Val Val Lys Leu Leu Ala Ser Asp Ala Gly Leu Tyr Arg Cys Asp Val
            100                 105                 110

Met Tyr Gly Ile Glu Asp Thr Gln Asp Thr Val Ser Leu Thr Val Asp
        115                 120                 125

Gly Val Val Phe His Tyr Arg Ala Ala Thr Ser Arg Tyr Thr Leu Asn
130                 135                 140

Phe Glu Ala Ala Gln Lys Ala Cys Leu Asp Val Gly Ala Val Ile Ala
145                 150                 155                 160

Thr Pro Glu Gln Leu Phe Ala Ala Tyr Glu Asp Gly Phe Glu Gln Cys
                165                 170                 175

Asp Ala Gly Trp Leu Ala Asp Gln Thr Val Arg Tyr Pro Ile Arg Ala
            180                 185                 190

Pro Arg Val Gly Cys Tyr Gly Asp Lys Met Gly Lys Ala Gly Val Arg
        195                 200                 205

Thr Tyr Gly Phe Arg Ser Pro Gln Glu Thr Tyr Asp Val Tyr Cys Tyr
    210                 215                 220

Val Asp His Leu Asp Gly Asp Val Phe His Leu Thr Val Pro Ser Lys
225                 230                 235                 240

Phe Thr Phe Glu Glu Ala Ala Lys Glu Cys Glu Asn Gln Asp Ala Arg
                245                 250                 255

Leu Ala Thr Val Gly Glu Leu Gln Ala Ala Trp Arg Asn Gly Phe Asp
            260                 265                 270

Gln Cys Asp Tyr Gly Trp Leu Ser Asp Ala Ser Val Arg His Pro Val
        275                 280                 285

Thr Val Ala Arg Ala Gln Cys Gly Gly Gly Leu Leu Gly Val Arg Thr
    290                 295                 300

Leu Tyr Arg Phe Glu Asn Gln Thr Gly Phe Pro Pro Pro Asp Ser Arg
305                 310                 315                 320

Phe Asp Ala Tyr Cys Phe Lys Pro Lys Glu Ala Thr Thr Ile Asp Leu
                325                 330                 335

Ser Ile Leu Ala Glu Thr Ala Ser Pro Ser Leu Ser Lys Glu Pro Gln
            340                 345                 350
```

-continued

```
Met Val Ser Asp Arg Thr Thr Pro Ile Ile Pro Leu Val Asp Glu Leu
        355                 360                 365

Pro Val Ile Pro Thr Glu Phe Pro Pro Val Gly Asn Ile Val Ser Phe
370                 375                 380

Glu Gln Lys Ala Thr Val Gln Pro Gln Ala Ile Thr Asp Ser Leu Ala
385                 390                 395                 400

Thr Lys Leu Pro Thr Pro Thr Gly Ser Thr Lys Lys Pro Trp Asp Met
                405                 410                 415

Asp Asp Tyr Ser Pro Ser Ala Ser Gly Pro Leu Gly Lys Leu Asp Ile
            420                 425                 430

Ser Glu Ile Lys Glu Val Leu Gln Ser Thr Gly Val Ser His
        435                 440                 445

Tyr Ala Thr Asp Ser Trp Asp Gly Val Val Glu Asp Lys Gln Thr Gln
    450                 455                 460

Glu Ser Val Thr Gln Ile Glu Gln Ile Glu Val Gly Pro Leu Val Thr
465                 470                 475                 480

Ser Met Glu Ile Leu Lys His Ile Pro Ser Lys Glu Phe Pro Val Thr
                485                 490                 495

Glu Thr Pro Leu Val Thr Ala Arg Met Ile Leu Glu Ser Lys Thr Glu
            500                 505                 510

Lys Lys Met Val Ser Thr Val Ser Glu Leu Val Thr Thr Gly His Tyr
        515                 520                 525

Gly Phe Thr Leu Gly Glu Glu Asp Asp Glu Arg Thr Leu Thr Val
    530                 535                 540

Gly Ser Asp Glu Ser Thr Leu Ile Phe Asp Gln Ile Pro Glu Val Ile
545                 550                 555                 560

Thr Val Ser Lys Thr Ser Glu Asp Thr Ile His Thr His Leu Glu Asp
                565                 570                 575

Leu Glu Ser Val Ser Ala Ser Thr Thr Val Ser Pro Leu Ile Met Pro
            580                 585                 590

Asp Asn Asn Gly Ser Ser Met Asp Asp Trp Glu Glu Arg Gln Thr Ser
        595                 600                 605

Gly Arg Ile Thr Glu Glu Phe Leu Gly Lys Tyr Leu Ser Thr Thr Pro
    610                 615                 620

Phe Pro Ser Gln His Arg Thr Glu Ile Glu Leu Phe Pro Tyr Ser Gly
625                 630                 635                 640

Asp Lys Ile Leu Val Glu Gly Ile Ser Thr Val Ile Tyr Pro Ser Leu
                645                 650                 655

Gln Thr Glu Met Thr His Arg Arg Glu Arg Thr Glu Thr Leu Ile Pro
            660                 665                 670

Glu Met Arg Thr Asp Thr Tyr Thr Asp Glu Ile Gln Glu Glu Ile Thr
        675                 680                 685

Lys Ser Pro Phe Met Gly Lys Thr Glu Glu Val Phe Ser Gly Met
    690                 695                 700

Lys Leu Ser Thr Ser Leu Ser Glu Pro Ile His Val Thr Glu Ser Ser
705                 710                 715                 720

Val Glu Met Thr Lys Ser Phe Asp Phe Pro Thr Leu Ile Thr Lys Leu
                725                 730                 735

Ser Ala Glu Pro Thr Glu Val Arg Asp Met Glu Glu Asp Phe Thr Ala
            740                 745                 750

Thr Pro Gly Thr Thr Lys Tyr Asp Glu Asn Ile Thr Thr Val Leu Leu
        755                 760                 765
```

```
Ala His Gly Thr Leu Ser Val Glu Ala Ala Thr Val Ser Lys Trp Ser
770                 775                 780
Trp Asp Glu Asp Asn Thr Thr Ser Lys Pro Leu Glu Ser Thr Glu Pro
785                 790                 795                 800
Ser Ala Ser Ser Lys Leu Pro Pro Ala Leu Leu Thr Thr Val Gly Met
                805                 810                 815
Asn Gly Lys Asp Lys Asp Ile Pro Ser Phe Thr Glu Asp Gly Ala Asp
                820                 825                 830
Glu Phe Thr Leu Ile Pro Asp Ser Thr Gln Lys Gln Leu Glu Glu Val
                835                 840                 845
Thr Asp Glu Asp Ile Ala Ala His Gly Lys Phe Thr Ile Arg Phe Gln
                850                 855                 860
Pro Thr Thr Ser Thr Gly Ile Ala Glu Lys Ser Thr Leu Arg Asp Ser
865                 870                 875                 880
Thr Thr Glu Glu Lys Val Pro Pro Ile Thr Ser Thr Glu Gly Gln Val
                885                 890                 895
Tyr Ala Thr Met Glu Gly Ser Ala Leu Gly Glu Val Glu Asp Val Asp
                900                 905                 910
Leu Ser Lys Pro Val Ser Thr Val Pro Gln Phe Ala His Thr Ser Glu
                915                 920                 925
Val Glu Gly Leu Ala Phe Val Ser Tyr Ser Ser Thr Gln Glu Pro Thr
                930                 935                 940
Thr Tyr Val Asp Ser Ser His Thr Ile Pro Leu Ser Val Ile Pro Lys
945                 950                 955                 960
Thr Asp Trp Gly Val Leu Val Pro Ser Val Pro Ser Glu Asp Glu Val
                965                 970                 975
Leu Gly Glu Pro Ser Gln Asp Ile Leu Val Ile Asp Gln Thr Arg Leu
                980                 985                 990
Glu Ala Thr Ile Ser Pro Glu Thr Met Arg Thr Thr Lys Ile Thr Glu
                995                1000                1005
Gly Thr Thr Gln Glu Glu Phe Pro Trp Lys Glu Gln Thr Ala Glu
        1010                1015                1020
Lys Pro Val Pro Ala Leu Ser Ser Thr Ala Trp Thr Pro Lys Glu
        1025                1030                1035
Ala Val Thr Pro Leu Asp Glu Gln Glu Gly Asp Gly Ser Ala Tyr
        1040                1045                1050
Thr Val Ser Glu Asp Glu Leu Leu Thr Gly Ser Glu Arg Val Pro
        1055                1060                1065
Val Leu Glu Thr Thr Pro Val Gly Lys Ile Asp His Ser Val Ser
        1070                1075                1080
Tyr Pro Pro Gly Ala Val Thr Glu His Lys Val Lys Thr Asp Glu
        1085                1090                1095
Val Val Thr Leu Thr Pro Arg Ile Gly Pro Lys Val Ser Leu Ser
        1100                1105                1110
Pro Gly Pro Glu Gln Lys Tyr Glu Thr Glu Gly Ser Ser Thr Thr
        1115                1120                1125
Gly Phe Thr Ser Ser Leu Ser Pro Phe Ser Thr His Ile Thr Gln
        1130                1135                1140
Leu Met Glu Glu Thr Thr Thr Glu Lys Thr Ser Leu Glu Asp Ile
        1145                1150                1155
Asp Leu Gly Ser Gly Leu Phe Glu Lys Pro Lys Ala Thr Glu Leu
        1160                1165                1170
Ile Glu Phe Ser Thr Ile Lys Val Thr Val Pro Ser Asp Ile Thr
```

```
                    1175                1180                1185

Thr Ala Phe Ser Ser Val Asp Arg Leu His Thr Thr Ser Ala Phe
                    1190                1195                1200

Lys Pro Ser Ser Ala Ile Thr Lys Lys Pro Pro Leu Ile Asp Arg
                    1205                1210                1215

Glu Pro Gly Glu Glu Thr Thr Ser Asp Met Val Ile Ile Gly Glu
                    1220                1225                1230

Ser Thr Ser His Val Pro Pro Thr Thr Leu Glu Asp Ile Val Ala
                    1235                1240                1245

Lys Glu Thr Glu Thr Asp Ile Asp Arg Glu Tyr Phe Thr Thr Ser
                    1250                1255                1260

Ser Pro Pro Ala Thr Gln Pro Thr Arg Pro Pro Thr Val Glu Asp
                    1265                1270                1275

Lys Glu Ala Phe Gly Pro Gln Ala Leu Ser Thr Pro Gln Pro Pro
                    1280                1285                1290

Ala Ser Thr Lys Phe His Pro Asp Ile Asn Val Tyr Ile Ile Glu
                    1295                1300                1305

Val Arg Glu Asn Lys Thr Gly Arg Met Ser Asp Leu Ser Val Ile
                    1310                1315                1320

Gly His Pro Ile Asp Ser Glu Ser Lys Glu Asp Glu Pro Cys Ser
                    1325                1330                1335

Glu Glu Thr Asp Pro Val His Asp Leu Met Ala Glu Ile Leu Pro
                    1340                1345                1350

Glu Phe Pro Asp Ile Ile Glu Ile Asp Leu Tyr His Ser Glu Glu
                    1355                1360                1365

Asn Glu Glu Glu Glu Glu Cys Ala Asn Ala Thr Asp Val Thr
                    1370                1375                1380

Thr Thr Pro Ser Val Gln Tyr Ile Asn Gly Lys His Leu Val Thr
                    1385                1390                1395

Thr Val Pro Lys Asp Pro Glu Ala Ala Glu Ala Arg Arg Gly Gln
                    1400                1405                1410

Phe Glu Ser Val Ala Pro Ser Gln Asn Phe Ser Asp Ser Ser Glu
                    1415                1420                1425

Ser Asp Thr His Pro Phe Val Ile Ala Lys Thr Glu Leu Ser Thr
                    1430                1435                1440

Ala Val Gln Pro Asn Glu Ser Thr Glu Thr Thr Glu Ser Leu Glu
                    1445                1450                1455

Val Thr Trp Lys Pro Glu Thr Tyr Pro Glu Thr Ser Glu His Phe
                    1460                1465                1470

Ser Gly Gly Glu Pro Asp Val Phe Pro Thr Val Pro Phe His Glu
                    1475                1480                1485

Glu Phe Glu Ser Gly Thr Ala Lys Lys Gly Ala Glu Ser Val Thr
                    1490                1495                1500

Glu Arg Asp Thr Glu Val Gly His Gln Ala His Glu His Thr Glu
                    1505                1510                1515

Pro Val Ser Leu Phe Pro Glu Glu Ser Ser Gly Glu Ile Ala Ile
                    1520                1525                1530

Asp Gln Glu Ser Gln Lys Ile Ala Phe Ala Arg Ala Thr Glu Val
                    1535                1540                1545

Thr Phe Gly Glu Glu Val Glu Lys Ser Thr Ser Val Thr Tyr Thr
                    1550                1555                1560

Pro Thr Ile Val Pro Ser Ser Ala Ser Ala Tyr Val Ser Glu Glu
                    1565                1570                1575
```

-continued

```
Glu Ala Val Thr Leu Ile Gly Asn Pro Trp Pro Asp Asp Leu Leu
1580                1585                1590

Ser Thr Lys Glu Ser Trp Val Glu Ala Thr Pro Arg Gln Val Val
    1595                1600                1605

Glu Leu Ser Gly Ser Ser Ser Ile Pro Ile Thr Glu Gly Ser Gly
1610                1615                1620

Glu Ala Glu Glu Asp Glu Asp Thr Met Phe Thr Met Val Thr Asp
1625                1630                1635

Leu Ser Gln Arg Asn Thr Thr Asp Thr Leu Ile Thr Leu Asp Thr
1640                1645                1650

Ser Arg Ile Ile Thr Glu Ser Phe Phe Glu Val Pro Ala Thr Thr
1655                1660                1665

Ile Tyr Pro Val Ser Glu Gln Pro Ser Ala Lys Val Val Pro Thr
1670                1675                1680

Lys Phe Val Ser Glu Thr Asp Thr Ser Glu Trp Ile Ser Ser Thr
1685                1690                1695

Thr Val Glu Glu Lys Lys Arg Lys Glu Glu Glu Gly Thr Thr Gly
1700                1705                1710

Thr Ala Ser Thr Phe Glu Val Tyr Ser Ser Thr Gln Arg Ser Asp
1715                1720                1725

Gln Leu Ile Leu Pro Phe Glu Leu Glu Ser Pro Asn Val Ala Thr
1730                1735                1740

Ser Ser Asp Ser Gly Thr Arg Lys Ser Phe Met Ser Leu Thr Thr
1745                1750                1755

Pro Thr Gln Ser Glu Arg Glu Met Thr Asp Ser Thr Pro Val Phe
1760                1765                1770

Thr Glu Thr Asn Thr Leu Glu Asn Leu Gly Ala Gln Thr Thr Glu
1775                1780                1785

His Ser Ser Ile His Gln Pro Gly Val Gln Gly Leu Thr Thr
1790                1795                1800

Leu Pro Arg Ser Pro Ala Ser Val Phe Met Glu Gln Gly Ser Gly
1805                1810                1815

Glu Ala Ala Ala Asp Pro Glu Thr Thr Thr Val Ser Ser Phe Ser
1820                1825                1830

Leu Asn Val Glu Tyr Ala Ile Gln Ala Glu Lys Glu Val Ala Gly
1835                1840                1845

Thr Leu Ser Pro His Val Glu Thr Thr Phe Ser Thr Glu Pro Thr
1850                1855                1860

Gly Leu Val Leu Ser Thr Val Met Asp Arg Val Val Ala Glu Asn
1865                1870                1875

Ile Thr Gln Thr Ser Arg Glu Ile Val Ile Ser Glu Arg Leu Gly
1880                1885                1890

Glu Pro Asn Tyr Gly Ala Glu Ile Arg Gly Phe Ser Thr Gly Phe
1895                1900                1905

Pro Leu Glu Glu Asp Phe Ser Gly Asp Phe Arg Glu Tyr Ser Thr
1910                1915                1920

Val Ser His Pro Ile Ala Lys Glu Glu Thr Val Met Met Glu Gly
1925                1930                1935

Ser Gly Asp Ala Ala Phe Arg Asp Thr Gln Thr Ser Pro Ser Thr
1940                1945                1950

Val Pro Thr Ser Val His Ile Ser His Ile Ser Asp Ser Glu Gly
1955                1960                1965
```

```
Pro Ser Ser Thr Met Val Ser Thr Ser Ala Phe Pro Trp Glu Glu
    1970            1975                1980

Phe Thr Ser Ser Ala Glu Gly Ser Gly Glu Gln Leu Val Thr Val
    1985                1990                1995

Ser Ser Ser Val Val Pro Val Leu Pro Ser Ala Val Gln Lys Phe
    2000                2005                2010

Ser Gly Thr Ala Ser Ser Ile Ile Asp Glu Gly Leu Gly Glu Val
    2015                2020                2025

Gly Thr Val Asn Glu Ile Asp Arg Arg Ser Thr Ile Leu Pro Thr
    2030                2035                2040

Ala Glu Val Glu Gly Thr Lys Ala Pro Val Glu Lys Glu Glu Val
    2045                2050                2055

Lys Val Ser Gly Thr Val Ser Thr Asn Phe Pro Gln Thr Ile Glu
    2060                2065                2070

Pro Ala Lys Leu Trp Ser Arg Gln Glu Val Asn Pro Val Arg Gln
    2075                2080                2085

Glu Ile Glu Ser Glu Thr Thr Ser Glu Glu Gln Ile Gln Glu Glu
    2090                2095                2100

Lys Ser Phe Glu Ser Pro Gln Asn Ser Pro Ala Thr Glu Gln Thr
    2105                2110                2115

Ile Phe Asp Ser Gln Thr Phe Thr Glu Thr Glu Leu Lys Thr Thr
    2120                2125                2130

Asp Tyr Ser Val Leu Thr Thr Lys Lys Thr Tyr Ser Asp Asp Lys
    2135                2140                2145

Glu Met Lys Glu Glu Asp Thr Ser Leu Val Asn Met Ser Thr Pro
    2150                2155                2160

Asp Pro Asp Ala Asn Gly Leu Glu Ser Tyr Thr Thr Leu Pro Glu
    2165                2170                2175

Ala Thr Glu Lys Ser His Phe Phe Leu Ala Thr Ala Leu Val Thr
    2180                2185                2190

Glu Ser Ile Pro Ala Glu His Val Val Thr Asp Ser Pro Ile Lys
    2195                2200                2205

Lys Glu Glu Ser Thr Lys His Phe Pro Lys Gly Met Arg Pro Thr
    2210                2215                2220

Ile Gln Glu Ser Asp Thr Glu Leu Leu Phe Ser Gly Leu Gly Ser
    2225                2230                2235

Gly Glu Glu Val Leu Pro Thr Leu Pro Thr Glu Ser Val Asn Phe
    2240                2245                2250

Thr Glu Val Glu Gln Ile Asn Asn Thr Leu Tyr Pro His Thr Ser
    2255                2260                2265

Gln Val Glu Ser Thr Ser Ser Asp Lys Ile Glu Asp Phe Asn Arg
    2270                2275                2280

Met Glu Asn Val Ala Lys Glu Val Gly Pro Leu Val Ser Gln Thr
    2285                2290                2295

Asp Ile Phe Glu Gly Ser Gly Ser Val Thr Ser Thr Thr Leu Ile
    2300                2305                2310

Glu Ile Leu Ser Asp Thr Gly Ala Glu Gly Pro Thr Val Ala Pro
    2315                2320                2325

Leu Pro Phe Ser Thr Asp Ile Gly His Pro Gln Asn Gln Thr Val
    2330                2335                2340

Arg Trp Ala Glu Glu Ile Gln Thr Ser Arg Pro Gln Thr Ile Thr
    2345                2350                2355

Glu Gln Asp Ser Asn Lys Asn Ser Ser Thr Ala Glu Ile Asn Glu
```

-continued

```
                2360                2365                2370
Thr Thr Thr Ser Ser Thr Asp Phe Leu Ala Arg Ala Tyr Gly Phe
        2375                2380                2385
Glu Met Ala Lys Glu Phe Val Thr Ser Ala Pro Lys Pro Ser Asp
        2390                2395                2400
Leu Tyr Tyr Glu Pro Ser Gly Glu Gly Ser Gly Glu Val Asp Ile
        2405                2410                2415
Val Asp Ser Phe His Thr Ser Ala Thr Thr Gln Ala Thr Arg Gln
        2420                2425                2430
Glu Ser Ser Thr Thr Phe Val Ser Asp Gly Ser Leu Glu Lys His
        2435                2440                2445
Pro Glu Val Pro Ser Ala Lys Ala Val Thr Ala Asp Gly Phe Pro
        2450                2455                2460
Thr Val Ser Val Met Leu Pro Leu His Ser Glu Gln Asn Lys Ser
        2465                2470                2475
Ser Pro Asp Pro Thr Ser Thr Leu Ser Asn Thr Val Ser Tyr Glu
        2480                2485                2490
Arg Ser Thr Asp Gly Ser Phe Gln Asp Arg Phe Arg Glu Phe Glu
        2495                2500                2505
Asp Ser Thr Leu Lys Pro Asn Arg Lys Lys Pro Thr Glu Asn Ile
        2510                2515                2520
Ile Ile Asp Leu Asp Lys Glu Asp Lys Asp Leu Ile Leu Thr Ile
        2525                2530                2535
Thr Glu Ser Thr Ile Leu Glu Ile Leu Pro Glu Leu Thr Ser Asp
        2540                2545                2550
Lys Asn Thr Ile Ile Asp Ile Asp His Thr Lys Pro Val Tyr Glu
        2555                2560                2565
Asp Ile Leu Gly Met Gln Thr Asp Ile Asp Thr Glu Val Pro Ser
        2570                2575                2580
Glu Pro His Asp Ser Asn Asp Glu Ser Asn Asp Asp Ser Thr Gln
        2585                2590                2595
Val Gln Glu Ile Tyr Glu Ala Ala Val Asn Leu Ser Leu Thr Glu
        2600                2605                2610
Glu Thr Phe Glu Gly Ser Ala Asp Val Leu Ala Ser Tyr Thr Gln
        2615                2620                2625
Ala Thr His Asp Glu Ser Met Thr Tyr Glu Asp Arg Ser Gln Leu
        2630                2635                2640
Asp His Met Gly Phe His Phe Thr Thr Gly Ile Pro Ala Pro Ser
        2645                2650                2655
Thr Glu Thr Glu Leu Asp Val Leu Leu Pro Thr Ala Thr Ser Leu
        2660                2665                2670
Pro Ile Pro Arg Lys Ser Ala Thr Val Ile Pro Glu Ile Glu Gly
        2675                2680                2685
Ile Lys Ala Glu Ala Lys Ala Leu Asp Asp Met Phe Glu Ser Ser
        2690                2695                2700
Thr Leu Ser Asp Gly Gln Ala Ile Ala Asp Gln Ser Glu Ile Ile
        2705                2710                2715
Pro Thr Leu Gly Gln Phe Glu Arg Thr Gln Glu Glu Tyr Glu Asp
        2720                2725                2730
Lys Lys His Ala Gly Pro Ser Phe Gln Pro Glu Phe Ser Ser Gly
        2735                2740                2745
Ala Glu Glu Ala Leu Val Asp His Thr Pro Tyr Leu Ser Ile Ala
        2750                2755                2760
```

-continued

```
Thr Thr His Leu Met Asp Gln Ser Val Thr Glu Val Pro Asp Val
        2765                2770                2775
Met Glu Gly Ser Asn Pro Pro Tyr Tyr Thr Asp Thr Thr Leu Ala
        2780                2785                2790
Val Ser Thr Phe Ala Lys Leu Ser Ser Gln Thr Pro Ser Ser Pro
        2795                2800                2805
Leu Thr Ile Tyr Ser Gly Ser Glu Ala Ser Gly His Thr Glu Ile
        2810                2815                2820
Pro Gln Pro Ser Ala Leu Pro Gly Ile Asp Val Gly Ser Ser Val
        2825                2830                2835
Met Ser Pro Gln Asp Ser Phe Lys Glu Ile His Val Asn Ile Glu
        2840                2845                2850
Ala Thr Phe Lys Pro Ser Ser Glu Glu Tyr Leu His Ile Thr Glu
        2855                2860                2865
Pro Pro Ser Leu Ser Pro Asp Thr Lys Leu Glu Pro Ser Glu Asp
        2870                2875                2880
Asp Gly Lys Pro Glu Leu Leu Glu Glu Met Glu Ala Ser Pro Thr
        2885                2890                2895
Glu Leu Ile Ala Val Glu Gly Thr Glu Ile Leu Gln Asp Phe Gln
        2900                2905                2910
Asn Lys Thr Asp Gly Gln Val Ser Gly Glu Ala Ile Lys Met Phe
        2915                2920                2925
Pro Thr Ile Lys Thr Pro Glu Ala Gly Thr Val Ile Thr Thr Ala
        2930                2935                2940
Asp Glu Ile Glu Leu Glu Gly Ala Thr Gln Trp Pro His Ser Thr
        2945                2950                2955
Ser Ala Ser Ala Thr Tyr Gly Val Glu Ala Gly Val Val Pro Trp
        2960                2965                2970
Leu Ser Pro Gln Thr Ser Glu Arg Pro Thr Leu Ser Ser Ser Pro
        2975                2980                2985
Glu Ile Asn Pro Glu Thr Gln Ala Ala Leu Ile Arg Gly Gln Asp
        2990                2995                3000
Ser Thr Ile Ala Ala Ser Glu Gln Gln Val Ala Ala Arg Ile Leu
        3005                3010                3015
Asp Ser Asn Asp Gln Ala Thr Val Asn Pro Val Glu Phe Asn Thr
        3020                3025                3030
Glu Val Ala Thr Pro Pro Phe Ser Leu Leu Glu Thr Ser Asn Glu
        3035                3040                3045
Thr Asp Phe Leu Ile Gly Ile Asn Glu Glu Ser Val Glu Gly Thr
        3050                3055                3060
Ala Ile Tyr Leu Pro Gly Pro Asp Arg Cys Lys Met Asn Pro Cys
        3065                3070                3075
Leu Asn Gly Gly Thr Cys Tyr Pro Thr Glu Thr Ser Tyr Val Cys
        3080                3085                3090
Thr Cys Val Pro Gly Tyr Ser Gly Asp Gln Cys Glu Leu Asp Phe
        3095                3100                3105
Asp Glu Cys His Ser Asn Pro Cys Arg Asn Gly Ala Thr Cys Val
        3110                3115                3120
Asp Gly Phe Asn Thr Phe Arg Cys Leu Cys Leu Pro Ser Tyr Val
        3125                3130                3135
Gly Ala Leu Cys Glu Gln Asp Thr Glu Thr Cys Asp Tyr Gly Trp
        3140                3145                3150
```

His Lys Phe Gln Gly Gln Cys Tyr Lys Tyr Phe Ala His Arg Arg
3155              3160              3165

Thr Trp Asp Ala Ala Glu Arg Glu Cys Arg Leu Gln Gly Ala His
3170              3175              3180

Leu Thr Ser Ile Leu Ser His Glu Glu Gln Met Phe Val Asn Arg
3185              3190              3195

Val Gly His Asp Tyr Gln Trp Ile Gly Leu Asn Asp Lys Met Phe
3200              3205              3210

Glu His Asp Phe Arg Trp Thr Asp Gly Ser Thr Leu Gln Tyr Glu
3215              3220              3225

Asn Trp Arg Pro Asn Gln Pro Asp Ser Phe Phe Ser Ala Gly Glu
3230              3235              3240

Asp Cys Val Val Ile Ile Trp His Glu Asn Gly Gln Trp Asn Asp
3245              3250              3255

Val Pro Cys Asn Tyr His Leu Thr Tyr Thr Cys Lys Lys Gly Thr
3260              3265              3270

Val Ala Cys Gly Gln Pro Pro Val Val Glu Asn Ala Lys Thr Phe
3275              3280              3285

Gly Lys Met Lys Pro Arg Tyr Glu Ile Asn Ser Leu Ile Arg Tyr
3290              3295              3300

His Cys Lys Asp Gly Phe Ile Gln Arg His Leu Pro Thr Ile Arg
3305              3310              3315

Cys Leu Gly Asn Gly Arg Trp Ala Ile Pro Lys Ile Thr Cys Met
3320              3325              3330

Asn Pro Ser Ala Tyr Gln Arg Thr Tyr Ser Met Lys Tyr Phe Lys
3335              3340              3345

Asn Ser Ser Ser Ala Lys Asp Asn Ser Ile Asn Thr Ser Lys His
3350              3355              3360

Asp His Arg Trp Ser Arg Arg Trp Gln Glu Ser Arg Arg
3365              3370              3375

<210> SEQ ID NO 5
<211> LENGTH: 7219
<212> TYPE: DNA
<213> ORGANISM: Homo sapiens

<400> SEQUENCE: 5

```
ggaccccggc aagcccgcgc acttggcagg agctgtagct accgccgtcc gcgcctccaa      60
ggtttcacgg cttcctcagc agagactcgg gctcgtccgc catgtccgcc gcagacgagg     120
ttgacgggct gggcgtggcc cggccgcact atggctctgt cctggataat gaaagactta     180
ctgcagagga gatggatgaa aggagacgtc agaacgtggc ttatgagtac ctttgtcatt     240
tggaagaagc gaagaggtgg atggaagcat gcctagggga agatctgcct cccaccacag     300
aactggagga ggggcttagg aatggggtct accttgccaa actggggaac ttcttctctc     360
ccaaagtagt gtccctgaaa aaatctatg atcgagaaca gaccagatac aaggcgactg      420
gcctccactt tagacacact gataatgtga ttcagtggtt gaatgccatg gatgagattg     480
gattgcctaa gattttttac ccagaaacta cagatatcta tgatcgaaag aacatgccaa     540
gatgtatcta ctgtatccat gcactcagtt tgtacctgtt caagctaggc ctggcccctc     600
agattcaaga cctatatgga aaggttgact tcacagaaga gaaatcaac aacatgaaga     660 ctgagttgga gaagtatggc atccagatgc ctgcctttag caagattggg ggcatcttgg     720
ctaatgaact gtcagtggat gaagccgcat acatgctgc tgttattgct attaatgaag     780
```

```
ctattgaccg tagaattcca gccgacacat ttgcagcttt gaaaaatccg aatgccatgc    840
ttgtaaatct tgaagagccc ttggcatcca cttaccagga tatactttac caggctaagc    900
aggacaaaat gacaaatgct aaaaacagga cagaaaactc agagagagaa agagatgttt    960
atgaggagct gctcacgcaa gctgaaattc aaggcaatat aaacaaagtc aatacatttt   1020
ctgcattagc aaatatcgac ctggctttag aacaaggaga tgcactggcc ttgttcaggg   1080
ctctgcagtc accagccctg ggcttcgag gactgcagca acagaatagc gactggtact    1140
tgaagcagct cctgagtgat aaacagcaga agagacagag tggtcagact gaccccctgc   1200
agaaggagga gctgcagtct ggagtggatg ctgcaaacag tgctgcccag caatatcaga   1260
gaagattggc agcagtagca ctgattaatg ctgcaatcca aagggtgtt gctgagaaga    1320 ctgttttgga actgatgaat cccgaagccc agctgcccca ggtgtatcca tttgccgccg   1380
atctctatca gaaggagctg gctaccctgc agcgacaaag tcctgaacat aatctcaccc   1440
acccagagct ctctgtcgca gtggagatgt tgtcatcggt ggccctgatc aacagggcat   1500
tggaatcagg agatgtgaat acagtgtgga agcaattgag cagttcagtt actggtctta   1560
ccaatattga ggaagaaaac tgtcagaggt atctcgatga gttgatgaaa ctgaaggctc   1620
aggcacatgc agagaataat gaattcatta catggaatga tatccaagct tgcgtggacc   1680
atgtgaacct ggtggtgcaa gaggaacatg agaggatttt agccattggt ttaattaatg   1740
aagccctgga tgaaggtgat gcccaaaaga ctctgcaggc cctacagatt cctgcagcta   1800
aacttgaggg agtccttgca gaagtggccc agcattacca agacacgctg attagagcga   1860
agagagagaa agcccaggaa atccaggatg agtcagctgt gttatggttg gatgaaattc   1920
aaggtggaat ctggcagtcc aacaaagaca cccaagaagc acagaagttt gccttaggaa   1980
tctttgccat taatgaggca gtagaaagtg gtgatgttgg caaaacactg agtgcccttc   2040
gctcccctga tgttggcttg tatggagtca tccctgagtg tggtgaaact taccacagtg   2100
atcttgctga agccaagaag aaaaaactgg cagtaggaga taataacagc aagtgggtga   2160
agcactgggt aaaaggtgga tattattatt accacaatct ggagacccag aaggaggat    2220 gggatgaacc tccaaatttt gtgcaaaatt ctatgcagct ttctcgggag agatccaga    2280 gttctatctc tggggtgact gccgcatata accgagaaca gctgtggctg ccaatgaag    2340 gcctgatcac caggctgcag gctcgctgcc gtggatactt agttcgacag gaattccgat   2400
ccaggatgaa tttcctgaag aaacaaatcc ctgccatcac ctgcattcag tcacagtgga   2460
gaggatacaa gcagaagaag gcatatcaag atcggttagc ttacctgcgc tcccacaaag   2520
atgaagttgt aaagattcag tccctggcaa ggatgcacca agctcgaaag cgctatcgag   2580
atcgcctgca gtacttccgg gaccatataa atgacattat caaaatccag gcttttattc   2640
gggcaaacaa agctcgggat gactacaaga ctctcatcaa tgctgaggat cctcctatgg   2700
ttgtggtccg aaaatttgtc cacctgctgg accaaagtga ccaggatttt caggaggagc   2760 ttgacctta tgaagatgcgg gaagaggtta tcaccctcat tcgttctaac cagcagctgg   2820
agaatgacct caatctcatg gatatcaaaa ttggactgct agtgaaaaat aagattacgt   2880
tgcaggatgt ggtttcccac agtaaaaaac ttaccaaaaa aaataaggaa cagttgtctg   2940
atatgatgat gataaataaa cagaagggag gtctcaaggc tttgagcaag gagaagagag   3000
agaagttgga agcttaccag cacctgtttt atttattgca aaccaatccc acctatctgg   3060
ccaagctcat ttttcagatg ccccagaaca agtccaccaa gttcatggac tctgtaatct   3120
tcacactcta caactacgcg tccaaccagc gagaggagta cctgctcctg cggctcttta   3180
```

```
agacagcact ccaagaggaa atcaagtcga aggtagatca gattcaagag attgtgacag   3240
gaaatcctac ggttattaaa atggttgtaa gtttcaaccg tggtgcccgt ggccagaatg   3300
ccctgagaca gatcttggcc ccagtcgtga aggaaattat ggatgacaaa tctctcaaca   3360
tcaaaactga ccctgtggat atttacaaat cttgggttaa tcagatggag tctcagacag   3420
gagaggcaag caaactgccc tatgatgtga cccctgagca ggcgctagct catgaagaag   3480
tgaagacacg gctagacagc tccatcagga acatgcgggc tgtgacagac aagtttctct   3540
cagccattgt cagctctgtg gacaaaatcc cttatgggat gcgcttcatt gccaaagtgc   3600
tgaaggactc gttgcatgag aagttccctg atgctggtga ggatgagctg ctgaagatta   3660
ttggtaactt gctttattat cgatacatga atccagccat tgttgctcct gatgcctttg   3720
acatcattga cctgtcagca ggaggccagc ttaccacaga ccaacgccga aatctgggct   3780
ccattgcaaa aatgcttcag catgctgctt ccaataagat gtttctggga gataatgccc   3840
acttaagcat cattaatgaa tatctttccc agtcctacca gaaattcaga cggttttttcc   3900 aaactgcttg tgatgtccca gagcttcagg ataaatttaa tgtggatgag tactctgatt   3960
tagtaaccct caccaaacca gtaatctaca tttccattgg tgaaatcatc aacacccaca   4020
ctctcctgtt ggatcaccag gatgccattg ctccggagca caatgatcca atccacgaac   4080
tgctggacga cctcggcgag gtgcccacca tcgagtccct gataggggaa agctctggca   4140
atttaaatga cccaaataag gaggcactgg ctaagacgga agtgtctctc accctgacca   4200
acaagttcga cgtgcctgga gatgagaatg cagaaatgga tgctcgaacc atcttactga   4260
atacaaaacg tttaattgtg gatgtcatcc ggttccagcc aggagagacc ttgactgaaa   4320
tcctagaaac accagccacc agtgaacagg aagcagaaca tcagagagcc atgcagagac   4380
gtgctatccg tgatgccaaa acacctgaca agatgaaaaa gtcaaaatct gtaaaggaag   4440
acagcaacct cactcttcaa gagaagaaag agaagatcca gacaggttta agaagctaa   4500 cagagcttgg aaccgtggac ccaaagaaca ataccagga actgatcaac gacattgcca   4560
gggatattcg gaatcagcgg aggtaccgac agagggagaa aggccgaacta gtgaaactgc   4620 aacagacata cgctgctctg aactctaagg ccacctttta tggggagcag gtggattact   4680
ataaaagcta tatcaaaacc tgcttggata acttagccag caagggcaaa gtctccaaaa   4740
agcctaggga aatgaaagga aagaaaagca aaaagatttc tctgaaatat acagcagcaa   4800
gactacatga aaaaggagtt cttctggaaa ttgaggacct gcaagtgaat cagtttaaaa   4860
atgttatatt tgaaatcagt ccaacagaag aagttggaga cttcgaagtg aaagccaaat   4920
tcatgggagt tcaaatggag acttttatgt tacattatca ggacctgctg cagctacagt   4980
atgaaggagt tgcagtcatg aaattatttg atagagctaa agtaaatgtc aacctcctga   5040
tcttccttct caacaaaaag ttctacggga gtaattgat cgtttgctgc cagcccagaa   5100
ggatgaagga aagaagcacc tcacagctcc tttctaggtc cttctttcct cattggaagc   5160
aaagacctag ccaacaacag cacctcaatc tgatacactc ccgatgccac attttaact   5220 cctctcgctc tgatgggaca tttgttaccc tttttcata gtgaaattgt gtttcaggct   5280
tagtctgacc tttctggttt cttcattttc ttccattact taggaaagag tggaaactcc   5340
actaaaattt ctctgtgttg ttacagtctt agaggttgca gtactatatt gtaagctttg   5400
gtgtttgttt aattagcaat agggatggta ggattcaaat gtgtgtcatt tagaagtgga   5460
agctattagc accaatgaca taaatacata caagacacac aactaaaatg tcatgttatt   5520
```

-continued

| | |
|---|---|
| aacagttatt aggttgtcat ttaaaaataa agttccttta tatttctgtc ccatcaggaa | 5580 |
| aactgaagga tatggggaat cattggttat cttccattgt gtttttcttt atggacagga | 5640 |
| gctaatggaa gtgacagtca tgttcaaagg aagcatttct agaaaaaagg agataatgtt | 5700 |
| tttaaatttc attatcaaac ttgggcaatt ctgtttgtgt aactccccga ctagtggatg | 5760 |
| ggagagtccc attgctaaaa ttcagctact cagataaatt cagaatgggt caaggcacct | 5820 |
| gcctgttttt gttggtgcac agagattgac ttgattcaga gagacaattc actccatccc | 5880 |
| tatggcagag gaatgggtta gccctaatgt agaatgtcat tgttttttaaa actgttttat | 5940 |
| atcttaagag tgccttatta aagtatagat gtatgtctta aaatgtgggt gataggaatt | 6000 |
| ttaaagattt atataatgca tcaaaagcct tagaataaga aaagcttttt ttaaattgct | 6060 |
| ttatctgtat atctgaactc ttgaaactta tagctaaaac actaggattt atctgcagtg | 6120 |
| ttcagggaga taattctgcc tttaattgtc taaaacaaaa acaaaaccag ccaacctatg | 6180 |
| ttacacgtga gattaaaacc aattttttcc ccatttttc tcctttttc tcttgctgcc | 6240 |
| cacattgtgc ctttatttta tgagcccag ttttctgggc ttagtttaaa aaaaaaatca | 6300 |
| agtctaaaca ttgcatttag aaagcttttg ttcttggata aaagtcata cactttaaaa | 6360 |
| aaaaaaaaaa cttttttccag gaaaatatat tgaaatcatg ctgctgagcc tctatttttct | 6420 |
| ttctttgatg ttttgattca gtattctttt atcataaatt tttagcattt aaaaattcac | 6480 |
| tgatgtacat taagccaata aactgcttta atgaataaca aactatgtag tgtgtccta | 6540 |
| ttataaatgc attggagaag tattttttatg agactcttta ctcaggtgca tggttacagc | 6600 |
| ccacagggag gcatggagtg ccatggaagg attcgccact acccagacct tgttttttgt | 6660 |
| tgtatttttgg aagacaggtt tttttaaagaa acatttttcct cagattaaaa gatgatgcta | 6720 |
| ttacaactag cattgcctca aaactgggga ccaaccaaag tgtgtcaacc ctgtttcctt | 6780 |
| aaaagaggct atgaatccca aaggccacat ccaagacagg caataatgag cagagtttac | 6840 |
| agctccttta ataaaatgtg tcagtaattt taaggtttat agttccctca acacaattgc | 6900 |
| taatgcagaa tagtgtaaaa tgcgcttcaa gaatgttgat gatgatgata tagaattgtg | 6960 |
| gctttagtag cacagaggat gccccaacaa actcatggcg ttgaaaccac acagttctca | 7020 |
| ttactgttat ttattagctg tagcattctc tgtctcctct ctctcctcct ttgaccttct | 7080 |
| cctcgaccag ccatcatgac atttaccatg aatttacttc ctcccaagag tttggactgc | 7140 |
| ccgtcagatt gttgctgcac atagttgcct ttgtatctct gtatgaaata aaaggtcatt | 7200 |
| tgttcatgtt aaaaaaaaa | 7219 |

<210> SEQ ID NO 6
<211> LENGTH: 1657
<212> TYPE: PRT
<213> ORGANISM: Homo sapiens

<400> SEQUENCE: 6

Met Ser Ala Ala Asp Glu Val Asp Gly Leu Gly Val Ala Arg Pro His
1               5                   10                  15

Tyr Gly Ser Val Leu Asp Asn Glu Arg Leu Thr Ala Glu Glu Met Asp
            20                  25                  30

Glu Arg Arg Arg Gln Asn Val Ala Tyr Glu Tyr Leu Cys His Leu Glu
        35                  40                  45

Glu Ala Lys Arg Trp Met Glu Ala Cys Leu Gly Glu Asp Leu Pro Pro
    50                  55                  60

Thr Thr Glu Leu Glu Glu Gly Leu Arg Asn Gly Val Tyr Leu Ala Lys

```
                65                  70                  75                  80
Leu Gly Asn Phe Phe Ser Pro Lys Val Val Ser Leu Lys Lys Ile Tyr
                    85                  90                  95
Asp Arg Glu Gln Thr Arg Tyr Lys Ala Thr Gly Leu His Phe Arg His
                    100                 105                 110
Thr Asp Asn Val Ile Gln Trp Leu Asn Ala Met Asp Glu Ile Gly Leu
                    115                 120                 125
Pro Lys Ile Phe Tyr Pro Glu Thr Thr Asp Ile Tyr Asp Arg Lys Asn
                    130                 135                 140
Met Pro Arg Cys Ile Tyr Cys Ile His Ala Leu Ser Leu Tyr Leu Phe
145                 150                 155                 160
Lys Leu Gly Leu Ala Pro Gln Ile Gln Asp Leu Tyr Gly Lys Val Asp
                    165                 170                 175
Phe Thr Glu Glu Glu Ile Asn Asn Met Lys Thr Glu Leu Glu Lys Tyr
                    180                 185                 190
Gly Ile Gln Met Pro Ala Phe Ser Lys Ile Gly Gly Ile Leu Ala Asn
                    195                 200                 205
Glu Leu Ser Val Asp Glu Ala Ala Leu His Ala Ala Val Ile Ala Ile
            210                 215                 220
Asn Glu Ala Ile Asp Arg Arg Ile Pro Ala Asp Thr Phe Ala Ala Leu
225                 230                 235                 240
Lys Asn Pro Asn Ala Met Leu Val Asn Leu Glu Glu Pro Leu Ala Ser
                    245                 250                 255
Thr Tyr Gln Asp Ile Leu Tyr Gln Ala Lys Gln Asp Lys Met Thr Asn
                    260                 265                 270
Ala Lys Asn Arg Thr Glu Asn Ser Glu Arg Glu Arg Asp Val Tyr Glu
            275                 280                 285
Glu Leu Leu Thr Gln Ala Glu Ile Gln Gly Asn Ile Asn Lys Val Asn
                    290                 295                 300
Thr Phe Ser Ala Leu Ala Asn Ile Asp Leu Ala Leu Glu Gln Gly Asp
305                 310                 315                 320
Ala Leu Ala Leu Phe Arg Ala Leu Gln Ser Pro Ala Leu Gly Leu Arg
                    325                 330                 335
Gly Leu Gln Gln Gln Asn Ser Asp Trp Tyr Leu Lys Gln Leu Leu Ser
                    340                 345                 350
Asp Lys Gln Gln Lys Arg Gln Ser Gly Gln Thr Asp Pro Leu Gln Lys
                    355                 360                 365
Glu Glu Leu Gln Ser Gly Val Asp Ala Ala Asn Ser Ala Ala Gln Gln
            370                 375                 380
Tyr Gln Arg Arg Leu Ala Ala Val Ala Leu Ile Asn Ala Ala Ile Gln
385                 390                 395                 400
Lys Gly Val Ala Glu Lys Thr Val Leu Glu Leu Met Asn Pro Glu Ala
                    405                 410                 415
Gln Leu Pro Gln Val Tyr Pro Phe Ala Ala Asp Leu Tyr Gln Lys Glu
                    420                 425                 430
Leu Ala Thr Leu Gln Arg Gln Ser Pro Glu His Asn Leu Thr His Pro
                    435                 440                 445
Glu Leu Ser Val Ala Val Glu Met Leu Ser Ser Val Ala Leu Ile Asn
            450                 455                 460
Arg Ala Leu Glu Ser Gly Asp Val Asn Thr Val Trp Lys Gln Leu Ser
465                 470                 475                 480
Ser Ser Val Thr Gly Leu Thr Asn Ile Glu Glu Glu Asn Cys Gln Arg
                    485                 490                 495
```

```
Tyr Leu Asp Glu Leu Met Lys Leu Lys Ala Gln Ala His Ala Glu Asn
            500                 505                 510

Asn Glu Phe Ile Thr Trp Asn Asp Ile Gln Ala Cys Val Asp His Val
        515                 520                 525

Asn Leu Val Val Gln Glu Glu His Glu Arg Ile Leu Ala Ile Gly Leu
    530                 535                 540

Ile Asn Glu Ala Leu Asp Glu Gly Asp Ala Gln Lys Thr Leu Gln Ala
545                 550                 555                 560

Leu Gln Ile Pro Ala Ala Lys Leu Glu Gly Val Leu Ala Glu Val Ala
                565                 570                 575

Gln His Tyr Gln Asp Thr Leu Ile Arg Ala Lys Arg Glu Lys Ala Gln
            580                 585                 590

Glu Ile Gln Asp Glu Ser Ala Val Leu Trp Leu Asp Glu Ile Gln Gly
        595                 600                 605

Gly Ile Trp Gln Ser Asn Lys Asp Thr Gln Glu Ala Gln Lys Phe Ala
    610                 615                 620

Leu Gly Ile Phe Ala Ile Asn Glu Ala Val Glu Ser Gly Asp Val Gly
625                 630                 635                 640

Lys Thr Leu Ser Ala Leu Arg Ser Pro Asp Val Gly Leu Tyr Gly Val
                645                 650                 655

Ile Pro Glu Cys Gly Glu Thr Tyr His Ser Asp Leu Ala Glu Ala Lys
            660                 665                 670

Lys Lys Lys Leu Ala Val Gly Asp Asn Asn Ser Lys Trp Val Lys His
        675                 680                 685

Trp Val Lys Gly Gly Tyr Tyr Tyr His Asn Leu Glu Thr Gln Glu
    690                 695                 700

Gly Gly Trp Asp Glu Pro Pro Asn Phe Val Gln Asn Ser Met Gln Leu
705                 710                 715                 720

Ser Arg Glu Glu Ile Gln Ser Ser Ile Ser Gly Val Thr Ala Ala Tyr
                725                 730                 735

Asn Arg Glu Gln Leu Trp Leu Ala Asn Glu Gly Leu Ile Thr Arg Leu
            740                 745                 750

Gln Ala Arg Cys Arg Gly Tyr Leu Val Arg Gln Glu Phe Arg Ser Arg
        755                 760                 765

Met Asn Phe Leu Lys Lys Gln Ile Pro Ala Ile Thr Cys Ile Gln Ser
    770                 775                 780

Gln Trp Arg Gly Tyr Lys Gln Lys Lys Ala Tyr Gln Asp Arg Leu Ala
785                 790                 795                 800

Tyr Leu Arg Ser His Lys Asp Glu Val Val Lys Ile Gln Ser Leu Ala
                805                 810                 815

Arg Met His Gln Ala Arg Lys Arg Tyr Arg Asp Arg Leu Gln Tyr Phe
            820                 825                 830

Arg Asp His Ile Asn Asp Ile Ile Lys Ile Gln Ala Phe Ile Arg Ala
        835                 840                 845

Asn Lys Ala Arg Asp Asp Tyr Lys Thr Leu Ile Asn Ala Glu Asp Pro
    850                 855                 860

Pro Met Val Val Arg Lys Phe Val His Leu Leu Asp Gln Ser Asp
865                 870                 875                 880

Gln Asp Phe Gln Glu Glu Leu Asp Leu Met Lys Met Arg Glu Glu Val
                885                 890                 895

Ile Thr Leu Ile Arg Ser Asn Gln Gln Leu Glu Asn Asp Leu Asn Leu
            900                 905                 910
```

-continued

```
Met Asp Ile Lys Ile Gly Leu Leu Val Lys Asn Lys Ile Thr Leu Gln
            915                 920                 925

Asp Val Val Ser His Ser Lys Lys Leu Thr Lys Lys Asn Lys Glu Gln
930                 935                 940

Leu Ser Asp Met Met Met Ile Asn Lys Gln Lys Gly Gly Leu Lys Ala
945                 950                 955                 960

Leu Ser Lys Glu Lys Arg Glu Lys Leu Glu Ala Tyr Gln His Leu Phe
                965                 970                 975

Tyr Leu Leu Gln Thr Asn Pro Thr Tyr Leu Ala Lys Leu Ile Phe Gln
            980                 985                 990

Met Pro Gln Asn Lys Ser Thr Lys Phe Met Asp Ser Val Ile Phe Thr
            995                 1000                1005

Leu Tyr Asn Tyr Ala Ser Asn Gln Arg Glu Glu Tyr Leu Leu Leu
        1010                1015            1020

Arg Leu Phe Lys Thr Ala Leu Gln Glu Glu Ile Lys Ser Lys Val
        1025                1030            1035

Asp Gln Ile Gln Glu Ile Val Thr Gly Asn Pro Thr Val Ile Lys
        1040                1045            1050

Met Val Val Ser Phe Asn Arg Gly Ala Arg Gly Gln Asn Ala Leu
        1055                1060            1065

Arg Gln Ile Leu Ala Pro Val Lys Glu Ile Met Asp Asp Lys
        1070                1075            1080

Ser Leu Asn Ile Lys Thr Asp Pro Val Asp Ile Tyr Lys Ser Trp
        1085                1090            1095

Val Asn Gln Met Glu Ser Gln Thr Gly Glu Ala Ser Lys Leu Pro
        1100                1105            1110

Tyr Asp Val Thr Pro Glu Gln Ala Leu Ala His Glu Glu Val Lys
        1115                1120            1125

Thr Arg Leu Asp Ser Ser Ile Arg Asn Met Arg Ala Val Thr Asp
        1130                1135            1140

Lys Phe Leu Ser Ala Ile Val Ser Ser Val Asp Lys Ile Pro Tyr
        1145                1150            1155

Gly Met Arg Phe Ile Ala Lys Val Leu Lys Asp Ser Leu His Glu
        1160                1165            1170

Lys Phe Pro Asp Ala Gly Glu Asp Glu Leu Leu Lys Ile Ile Gly
        1175                1180            1185

Asn Leu Leu Tyr Tyr Arg Tyr Met Asn Pro Ala Ile Val Ala Pro
        1190                1195            1200

Asp Ala Phe Asp Ile Ile Asp Leu Ser Ala Gly Gly Gln Leu Thr
        1205                1210            1215

Thr Asp Gln Arg Arg Asn Leu Gly Ser Ile Ala Lys Met Leu Gln
        1220                1225            1230

His Ala Ala Ser Asn Lys Met Phe Leu Gly Asp Asn Ala His Leu
        1235                1240            1245

Ser Ile Ile Asn Glu Tyr Leu Ser Gln Ser Tyr Gln Lys Phe Arg
        1250                1255            1260

Arg Phe Phe Gln Thr Ala Cys Asp Val Pro Glu Leu Gln Asp Lys
        1265                1270            1275

Phe Asn Val Asp Glu Tyr Ser Asp Leu Val Thr Leu Thr Lys Pro
        1280                1285            1290

Val Ile Tyr Ile Ser Ile Gly Glu Ile Ile Asn Thr His Thr Leu
        1295                1300            1305

Leu Leu Asp His Gln Asp Ala Ile Ala Pro Glu His Asn Asp Pro
```

|  |  | 1310 |  |  |  | 1315 |  |  |  | 1320 |  |
| --- | --- | --- | --- | --- | --- | --- | --- | --- | --- | --- | --- |

Ile His Glu Leu Leu Asp Asp Leu Gly Glu Val Pro Thr Ile Glu
    1325                1330                1335

Ser Leu Ile Gly Glu Ser Ser Gly Asn Leu Asn Asp Pro Asn Lys
    1340                1345                1350

Glu Ala Leu Ala Lys Thr Glu Val Ser Leu Thr Leu Thr Asn Lys
    1355                1360                1365

Phe Asp Val Pro Gly Asp Glu Asn Ala Glu Met Asp Ala Arg Thr
    1370                1375                1380

Ile Leu Leu Asn Thr Lys Arg Leu Ile Val Asp Val Ile Arg Phe
    1385                1390                1395

Gln Pro Gly Glu Thr Leu Thr Glu Ile Leu Glu Thr Pro Ala Thr
    1400                1405                1410

Ser Glu Gln Glu Ala Glu His Gln Arg Ala Met Gln Arg Arg Ala
    1415                1420                1425

Ile Arg Asp Ala Lys Thr Pro Asp Lys Met Lys Lys Ser Lys Ser
    1430                1435                1440

Val Lys Glu Asp Ser Asn Leu Thr Leu Gln Glu Lys Lys Glu Lys
    1445                1450                1455

Ile Gln Thr Gly Leu Lys Lys Leu Thr Glu Leu Gly Thr Val Asp
    1460                1465                1470

Pro Lys Asn Lys Tyr Gln Glu Leu Ile Asn Asp Ile Ala Arg Asp
    1475                1480                1485

Ile Arg Asn Gln Arg Arg Tyr Arg Gln Arg Arg Lys Ala Glu Leu
    1490                1495                1500

Val Lys Leu Gln Gln Thr Tyr Ala Ala Leu Asn Ser Lys Ala Thr
    1505                1510                1515

Phe Tyr Gly Glu Gln Val Asp Tyr Tyr Lys Ser Tyr Ile Lys Thr
    1520                1525                1530

Cys Leu Asp Asn Leu Ala Ser Lys Gly Lys Val Ser Lys Lys Pro
    1535                1540                1545

Arg Glu Met Lys Gly Lys Lys Ser Lys Lys Ile Ser Leu Lys Tyr
    1550                1555                1560

Thr Ala Ala Arg Leu His Glu Lys Gly Val Leu Leu Glu Ile Glu
    1565                1570                1575

Asp Leu Gln Val Asn Gln Phe Lys Asn Val Ile Phe Glu Ile Ser
    1580                1585                1590

Pro Thr Glu Glu Val Gly Asp Phe Glu Val Lys Ala Lys Phe Met
    1595                1600                1605

Gly Val Gln Met Glu Thr Phe Met Leu His Tyr Gln Asp Leu Leu
    1610                1615                1620

Gln Leu Gln Tyr Glu Gly Val Ala Val Met Lys Leu Phe Asp Arg
    1625                1630                1635

Ala Lys Val Asn Val Asn Leu Leu Ile Phe Leu Leu Asn Lys Lys
    1640                1645                1650

Phe Tyr Gly Lys
    1655

<210> SEQ ID NO 7
<211> LENGTH: 847
<212> TYPE: DNA
<213> ORGANISM: Homo sapiens

<400> SEQUENCE: 7

```
acagagtaaa ctttttgctgg gctccaagtg accgcccata gtttattata aaggtgactg      60
caccctgcag ccaccagcac tgcctggctc cacgtgcctc ctggtctcag tatggcgctg     120
tcctgggttc ttacagtcct gagcctccta cctctgctgg aagcccagat cccattgtgt     180
gccaacctag taccggtgcc catcaccaac gccaccctgg accggatcac tggcaagtgg     240
ttttatatcg catcggcctt tcgaaacgag gagtacaata agtcggttca ggagatccaa     300
gcaaccttct tttacttcac ccccaacaag acagaggaca cgatctttct cagagagtac     360
cagacccgac aggaccagtg catctataac accacctacc tgaatgtcca gcgggaaaat     420
gggaccatct ccagatacgt gggaggccaa gagcatttcg ctcacttgct gatcctcagg     480
gacaccaaga cctacatgct tgcttttgac gtgaacgatg agaagaactg ggggctgtct     540
gtctatgctg acaagccaga gacgaccaag gagcaactgg gagagttcta cgaagctctc     600
gactgcttgc gcattcccaa gtcagatgtc gtgtacaccg attggaaaaa ggataagtgt     660
gagccactgg agaagcagca cgagaaggag aggaaacagg aggaggggga atcctagcag     720
gacacagcct tggatcagga cagagacttg ggggccatcc tgcccctcca acccgacatg     780
tgtacctcag cttttttccct cacttgcatc aataaagctt ctgtgtttgg aacagctaaa     840
aaaaaaa                                                                847
```

<210> SEQ ID NO 8
<211> LENGTH: 201
<212> TYPE: PRT
<213> ORGANISM: Homo sapiens

<400> SEQUENCE: 8

```
Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Arg Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
        115                 120                 125

Met Leu Ala Phe Asp Val Asn Asp Glu Lys Asn Trp Gly Leu Ser Val
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Val Val Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200
```

<210> SEQ ID NO 9

<211> LENGTH: 1447
<212> TYPE: DNA
<213> ORGANISM: Homo sapiens

<400> SEQUENCE: 9

```
tgtcactgag ggttgactga ctggagagct caagtgcagc aaagagaagt gtcagagcat    60
gagcgccaag tccagaacca tagggattat tggagctcct ttctcaaagg gacagccacg   120
aggaggggtg gaagaaggcc ctacagtatt gagaaaggct ggtctgcttg agaaacttaa   180
agaacaagag tgtgatgtga aggattatgg ggacctgccc tttgctgaca tccctaatga   240
cagtcccttt caaattgtga agaatccaag gtctgtggga aaagcaagcg agcagctggc   300
tggcaaggtg gcagaagtca agaagaacgg aagaatcagc ctggtgctgg gcggagacca   360
cagtttggca attggaagca tctctggcca tgccagggtc caccctgatc ttggagtcat   420
ctgggtggat gctcacactg atatcaacac tccactgaca accacaagtg gaaacttgca   480
tggacaacct gtatctttcc tcctgaagga actaaaagga aagattcccg atgtgccagg   540
attctcctgg gtgactccct gtatatctgc caaggatatt gtgtatattg gcttgagaga   600
cgtggaccct ggggaacact acattttgaa aactctaggc attaaatact tttcaatgac   660
tgaagtggac agactaggaa ttggcaaggt gatggaagaa acactcagct atctactagg   720
aagaaagaaa ggccaattc atctaagttt tgatgttgac ggactggacc catctttcac   780
accagctact ggcacaccag tcgtgggagg tctgacatac agaaaggtc tctacatcac   840
agaagaaatc tacaaaacag gctactctc aggattagat ataatggaag tgaacccatc   900
cctggggaag acaccagaag aagtaactcg aacagtgaac acagcagttg caataacctt   960
ggcttgtttc ggacttgctc gggagggtaa tcacaagcct attgactacc ttaacccacc  1020
taagtaaatg tggaaacatc cgatataaat ctcatagtta atggcataat tagaaagcta  1080
atcattttct taagcataga gttatccttc taaagacttg ttctttcaga aaaatgtttt  1140
tccaattagt ataaactcta caaattccct cttggtgtaa aattcaagat gtggaaattc  1200
taactttttt gaaatttaaa agcttatatt ttctaacttg gcaaaagact tatccttaga  1260
aagagaagtg tacattgatt tccaattaaa aatttgctgg cattaaaaat aagcacactt  1320
acataagccc ccatacatag agtgggactc ttggaatcag gagacaaagc taccacatgt  1380
ggaaaggtac tatgtgtcca tgtcattcaa aaaatgtgat tttttataat aaactcttta  1440
taacaag                                                            1447
```

<210> SEQ ID NO 10
<211> LENGTH: 322
<212> TYPE: PRT
<213> ORGANISM: Homo sapiens

<400> SEQUENCE: 10

Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
            85                  90                  95

Leu Gly Gly Asp His Ser Leu Ala Ile Gly Ser Ile Ser Gly His Ala
        100                 105                 110

Arg Val His Pro Asp Leu Gly Val Ile Trp Val Asp Ala His Thr Asp
    115                 120                 125

Ile Asn Thr Pro Leu Thr Thr Thr Ser Gly Asn Leu His Gly Gln Pro
130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys

<210> SEQ ID NO 11
<211> LENGTH: 619
<212> TYPE: DNA
<213> ORGANISM: Homo sapiens

<400> SEQUENCE: 11
agttaaatct tttctgctta ctgaaaagga agagtctgat gattagttac tgatcctctt       60
tgcatttgta aagctttgga gatattgaat catgttacca tttctgtttt tttccaccct      120
gttttcttcc atatttactg aagctcagaa gcagtattgg gtctgcaact catccgatgc      180
aagtatttca tacacctact gtgataaaat gcaataccca atttcaatta atgttaaccc      240
ctgtatagaa ttgaaaagat ccaaaggatt attgcacatt ttctacattc caaggagaga      300
tttaaagcaa ttatatttca atctctatat aactgtcaac accatgaatc ttccaaagcg      360
caaagaagtt atttgccgag atctgatga cgattactct ttttgcagag ctctgaaggg      420
agagactgtg aatacaacaa tatcattctc cttcaaggga ataaaatttt ctaagggaaa      480
atacaaatgt gttgttgaag ctatttctgg gagcccagaa gaaatgctct tttgcttgga      540
gtttgtcatc ctacaccaac ctaattcaaa ttagaataaa ttgagtattt aaaaaaaaaa      600
aaaaaaaaaa aaaaaaaa                                                   619

<210> SEQ ID NO 12

<211> LENGTH: 2387
<212> TYPE: DNA
<213> ORGANISM: Homo sapiens

<400> SEQUENCE: 12

| | | | | | |
|---|---|---|---|---|---|
| agacacctct | gccctcacca | tgagcctctg | gcagcccctg | gtcctggtgc | tcctggtgct | 60 |
| gggctgctgc | tttgctgccc | ccagacagcg | ccagtccacc | cttgtgctct | tccctggaga | 120 |
| cctgagaacc | aatctcaccg | acaggcagct | ggcagaggaa | tacctgtacc | gctatggtta | 180 |
| cactcgggtg | gcagagatgc | gtggagagtc | gaaatctctg | gggcctgcgc | tgctgcttct | 240 |
| ccagaagcaa | ctgtccctgc | ccgagaccgg | tgagctggat | agcgccacgc | tgaaggccat | 300 |
| gcgaacccca | cggtgcgggg | tcccagacct | gggcagattc | caaacctttg | agggcgacct | 360 |
| caagtggcac | caccacaaca | tcacctattg | gatccaaaac | tactcggaag | acttgccgcg | 420 |
| ggcggtgatt | gacgacgcct | tgcccgcgc | cttcgcactg | tggagcgcgg | tgacgccgct | 480 |
| caccttcact | cgcgtgtaca | gccgggacgc | agacatcgtc | atccagtttg | tgtcgcgga | 540 |
| gcacggagac | gggtatccct | tcgacgggaa | ggacgggctc | ctggcacacg | cctttcctcc | 600 |
| tggccccggc | attcagggag | acgcccattt | cgacgatgac | gagttgtggt | ccctgggcaa | 660 |
| gggcgtcgtg | gttccaactc | ggtttggaaa | cgcagatggc | gcggcctgcc | acttcccctt | 720 |
| catcttcgag | ggccgctcct | actctgcctg | caccaccgac | ggtcgctccg | acggcttgcc | 780 |
| ctggtgcagt | accacggcca | actacgacac | cgacgaccgg | tttggcttct | gccccagcga | 840 |
| gagactctac | acccaggacg | gcaatgctga | tgggaaaccc | tgccagtttc | cattcatctt | 900 |
| ccaaggccaa | tcctactccg | cctgcaccac | ggacggtcgc | tccgacggct | accgctggtg | 960 |
| cgccaccacc | gccaactacg | accgggacaa | gctcttcggc | ttctgcccga | cccgagctga | 1020 |
| ctcgacggtc | atggggggca | actcggcggg | ggagctgtgc | gtcttcccct | tcactttcct | 1080 |
| gggtaaggag | tactcgacct | gtaccagcga | gggccgcgga | gatgggcgcc | tctggtgcgc | 1140 |
| taccacctcg | aactttgaca | cgacaagaa | gtgggcttc | tgcccggacc | aaggatacag | 1200 |
| tttgttcctc | gtggcggcgc | atgagttcgg | ccacgcgctg | ggcttagatc | attcctcagt | 1260 |
| gccggaggcg | ctcatgtacc | ctatgtaccg | cttcactgag | gggcccccct | tgcataagga | 1320 |
| cgacgtgaat | ggcatccggc | acctctatgg | tcctcgccct | gaacctgagc | cacggcctcc | 1380 |
| aaccaccacc | acaccgcagc | ccacggctcc | ccgacggtc | tgccccaccg | gaccccccac | 1440 |
| tgtccacccc | tcagagcgcc | ccacagctgg | ccccacaggt | cccccctcag | ctggccccac | 1500 |
| aggtcccccc | actgctggcc | cttctacggc | cactactgtg | cctttgagtc | cggtggacga | 1560 |
| tgcctgcaac | gtgaacatct | tcgacgccat | cgcggagatt | gggaaccagc | tgtatttgtt | 1620 |
| caaggatggg | aagtactggc | gattctctga | gggcaggggg | agccggccgc | agggcccctt | 1680 |
| ccttatcgcc | gacaagtggc | ccgcgctgcc | ccgcaagctg | gactcggtct | ttgaggagcg | 1740 |
| gctctccaag | aagcttttct | tcttctctgg | gcgccaggtg | tgggtgtaca | caggcgcgtc | 1800 |
| ggtgctgggc | ccgaggcgtc | tggacaagct | gggcctggga | gccgacgtgg | cccaggtgac | 1860 |
| cggggccctc | cggagtggca | ggggaagat | gctgctgttc | agcgggcggc | gcctctggag | 1920 |
| gttcgacgtg | aagcgcgaga | tggtggatcc | cggagcgcc | agcgaggtgg | accgatgtt | 1980 |
| ccccgggtg | cctttggaca | cgcacgacgt | cttccagtac | cgagagaaag | cctatttctg | 2040 |
| ccaggaccgc | ttctactggc | gcgtgagttc | ccggagtgag | ttgaaccagg | tggaccaagt | 2100 |
| gggctacgta | acctatgaca | tcctgcagtg | ccctgaggac | tagggctccc | gtcctgcttt | 2160 |
| ggcagtgcca | tgtaaatccc | cactgggacc | aaccctgggg | aaggagccag | tttgccggat | 2220 |

```
acaaactggt attctgttct ggaggaaagg gaggagtgga ggtgggctgg gccctctctt    2280
ctcacctttg tttttgttg gagtgttct aataaacttg gattctctaa cctttaaaaa    2340
aaaaaaaaaa aaaaaaaaaa aaaaaaaaaa aaaaaaaaaa aaaaaaa                  2387

<210> SEQ ID NO 13
<211> LENGTH: 707
<212> TYPE: PRT
<213> ORGANISM: Homo sapiens

<400> SEQUENCE: 13

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
```

```
                340             345             350
Phe Leu Gly Lys Glu Tyr Ser Thr Cys Thr Ser Glu Gly Arg Gly Asp
            355                 360                 365
Gly Arg Leu Trp Cys Ala Thr Thr Ser Asn Phe Asp Ser Asp Lys Lys
        370                 375                 380
Trp Gly Phe Cys Pro Asp Gln Gly Tyr Ser Leu Phe Leu Val Ala Ala
385                 390                 395                 400
His Glu Phe Gly His Ala Leu Gly Leu Asp His Ser Ser Val Pro Glu
                405                 410                 415
Ala Leu Met Tyr Pro Met Tyr Arg Phe Thr Glu Gly Pro Pro Leu His
            420                 425                 430
Lys Asp Asp Val Asn Gly Ile Arg His Leu Tyr Gly Pro Arg Pro Glu
        435                 440                 445
Pro Glu Pro Arg Pro Pro Thr Thr Thr Pro Gln Pro Thr Ala Pro
    450                 455                 460
Pro Thr Val Cys Pro Thr Gly Pro Pro Thr Val His Pro Ser Glu Arg
465                 470                 475                 480
Pro Thr Ala Gly Pro Thr Gly Pro Pro Ser Ala Gly Pro Thr Gly Pro
                485                 490                 495
Pro Thr Ala Gly Pro Ser Thr Ala Thr Thr Val Pro Leu Ser Pro Val
            500                 505                 510
Asp Asp Ala Cys Asn Val Asn Ile Phe Asp Ala Ile Ala Glu Ile Gly
        515                 520                 525
Asn Gln Leu Tyr Leu Phe Lys Asp Gly Lys Tyr Trp Arg Phe Ser Glu
    530                 535                 540
Gly Arg Gly Ser Arg Pro Gln Gly Pro Phe Leu Ile Ala Asp Lys Trp
545                 550                 555                 560
Pro Ala Leu Pro Arg Lys Leu Asp Ser Val Phe Glu Glu Arg Leu Ser
                565                 570                 575
Lys Lys Leu Phe Phe Phe Ser Gly Arg Gln Val Trp Val Tyr Thr Gly
            580                 585                 590
Ala Ser Val Leu Gly Pro Arg Arg Leu Asp Lys Leu Gly Leu Gly Ala
        595                 600                 605
Asp Val Ala Gln Val Thr Gly Ala Leu Arg Ser Gly Arg Gly Lys Met
    610                 615                 620
Leu Leu Phe Ser Gly Arg Arg Leu Trp Arg Phe Asp Val Lys Ala Gln
625                 630                 635                 640
Met Val Asp Pro Arg Ser Ala Ser Glu Val Asp Arg Met Phe Pro Gly
                645                 650                 655
Val Pro Leu Asp Thr His Asp Val Phe Gln Tyr Arg Glu Lys Ala Tyr
            660                 665                 670
Phe Cys Gln Asp Arg Phe Tyr Trp Arg Val Ser Ser Arg Ser Glu Leu
        675                 680                 685
Asn Gln Val Asp Gln Val Gly Tyr Val Thr Tyr Asp Ile Leu Gln Cys
    690                 695                 700
Pro Glu Asp
705

<210> SEQ ID NO 14
<211> LENGTH: 160
<212> TYPE: PRT
<213> ORGANISM: Homo sapiens

<400> SEQUENCE: 14
```

Met Leu Pro Phe Leu Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
            35                  40                  45

Asn Pro Cys Ile Glu Leu Lys Arg Ser Lys Gly Leu Leu His Ile Phe
        50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
            115                 120                 125

Gly Lys Tyr Lys Cys Val Val Glu Ala Ile Ser Gly Ser Pro Glu Glu
            130                 135                 140

Met Leu Phe Cys Leu Glu Phe Val Ile Leu His Gln Pro Asn Ser Asn
145                 150                 155                 160

<210> SEQ ID NO 15
<211> LENGTH: 1165
<212> TYPE: DNA
<213> ORGANISM: Homo sapiens

<400> SEQUENCE: 15
cgctataaaa cccaggccgg caggatcgct gcacccgcgg cggcctcctc ggtgcgcgac      60
ccccggctca gaggactctt tgctgtcccg caagatgcgg atgctgctgg cgctcctggc     120
cctctccgcg gcgcggccat cggccagtgc agagtcacac tggtgctacg aggttcaagc     180
cgagtcctcc aactacccct gcttggtgcc agtcaagtgg ggtggaaact gccagaagga     240
ccgccagtcc cccatcaaca tcgtcaccac caaggcaaag gtggacaaaa actgggacg     300
cttcttcttc tctggctacg ataagaagca aacgtggact gtccaaaata cgggcactc     360
agtgatgatg ttgctggaga caaggccag catttctgga ggaggactgc ctgccccata     420
ccaggccaaa cagttgcacc tgcactggtc cgacttgcca tataagggct cggagcacag     480
cctcgatggg gagcactttg ccatggagat gcacatagta catgagaaag agaaggggac     540
atcgaggaat gtgaaagagg cccaggaccc tgaagacgaa attgcggtgc tggcctttct     600
ggtggaggct ggaacccagg tgaacgaggg cttccagcca ctggtggagg cactgtctaa     660
tatccccaaa cctgagatga gcactacgat ggcagagagc agcctgttgg acctgctccc     720
caaggaggag aaactgaggc actacttccg ctacctgggc tcactcacca caccgacctg     780
cgatgagaag gtcgtctgga ctgtgttccg ggagcccatt cagcttcaca gagaacagat     840
cctggcattc tctcagaagc tgtactacga caaggaacag acagtgagca tgaaggacaa     900
tgtcaggccc ctgcagcagc tgggcagcg cacggtgata aagtccgggg ccccgggtcg     960
gccgctgccc tgggccctgc ctgccctgct gggccccatg ctggcctgcc tgctggccgg    1020
cttcctgcga tgatggctca cttctgcacg cagcctctct gttgcctcag ctctccaagt    1080
tccaggcttc cggtccttag ccttcccagg tgggacttta ggcatgatta aatatggac     1140
atattttgg agaaaaaaaa aaaaa                                           1165

<210> SEQ ID NO 16
<211> LENGTH: 312
<212> TYPE: PRT
<213> ORGANISM: Homo sapiens

<400> SEQUENCE: 16

```
Met Arg Met Leu Leu Ala Leu Leu Ala Leu Ser Ala Ala Arg Pro Ser
1               5                   10                  15

Ala Ser Ala Glu Ser His Trp Cys Tyr Glu Val Gln Ala Glu Ser Ser
            20                  25                  30

Asn Tyr Pro Cys Leu Val Pro Val Lys Trp Gly Gly Asn Cys Gln Lys
        35                  40                  45

Asp Arg Gln Ser Pro Ile Asn Ile Val Thr Thr Lys Ala Lys Val Asp
    50                  55                  60

Lys Lys Leu Gly Arg Phe Phe Phe Ser Gly Tyr Asp Lys Lys Gln Thr
65                  70                  75                  80

Trp Thr Val Gln Asn Asn Gly His Ser Val Met Met Leu Leu Glu Asn
                85                  90                  95

Lys Ala Ser Ile Ser Gly Gly Leu Pro Ala Pro Tyr Gln Ala Lys
            100                 105                 110

Gln Leu His Leu His Trp Ser Asp Leu Pro Tyr Lys Gly Ser Glu His
        115                 120                 125

Ser Leu Asp Gly Glu His Phe Ala Met Glu Met His Ile Val His Glu
    130                 135                 140

Lys Glu Lys Gly Thr Ser Arg Asn Val Lys Glu Ala Gln Asp Pro Glu
145                 150                 155                 160

Asp Glu Ile Ala Val Leu Ala Phe Leu Val Glu Ala Gly Thr Gln Val
                165                 170                 175

Asn Glu Gly Phe Gln Pro Leu Val Glu Ala Leu Ser Asn Ile Pro Lys
            180                 185                 190

Pro Glu Met Ser Thr Thr Met Ala Glu Ser Ser Leu Leu Asp Leu Leu
        195                 200                 205

Pro Lys Glu Glu Lys Leu Arg His Tyr Phe Arg Tyr Leu Gly Ser Leu
    210                 215                 220

Thr Thr Pro Thr Cys Asp Glu Lys Val Val Trp Thr Val Phe Arg Glu
225                 230                 235                 240

Pro Ile Gln Leu His Arg Glu Gln Ile Leu Ala Phe Ser Gln Lys Leu
                245                 250                 255

Tyr Tyr Asp Lys Glu Gln Thr Val Ser Met Lys Asp Asn Val Arg Pro
            260                 265                 270

Leu Gln Gln Leu Gly Gln Arg Thr Val Ile Lys Ser Gly Ala Pro Gly
        275                 280                 285

Arg Pro Leu Pro Trp Ala Leu Pro Ala Leu Leu Gly Pro Met Leu Ala
    290                 295                 300

Cys Leu Leu Ala Gly Phe Leu Arg
305                 310
```

<210> SEQ ID NO 17
<211> LENGTH: 466
<212> TYPE: DNA
<213> ORGANISM: Homo sapiens

<400> SEQUENCE: 17

```
accactgctg gcttttttgct gtagctccac attcctgtgc attgaggggt taacattagg    60
ctgggaagat gacaaaactt gaagagcatc tggagggaat tgtcaatatc ttccaccaat   120
```

-continued

```
actcagttcg gaaggggcat tttgacaccc tctctaaggg tgagctgaag cagctgctta    180
caaaggagct tgcaaacacc atcaagaata tcaaagataa agctgtcatt gatgaaatat    240
tccaaggcct ggatgctaat caagatgaac aggtcgactt tcaagaattc atatccctgg    300
tagccattgc gctgaaggct gcccattacc acacccacaa agagtaggta gctctctgaa    360 ggcttttac ccagcaatgt cctcaatgag ggtcttttct ttccctcacc aaaacccagc     420
cttgcccgtg gggagtaaga gttaataaac acactcacga aaagtt                   466
```

<210> SEQ ID NO 18
<211> LENGTH: 92
<212> TYPE: PRT
<213> ORGANISM: Homo sapiens

<400> SEQUENCE: 18

```
Met Thr Lys Leu Glu Glu His Leu Glu Gly Ile Val Asn Ile Phe His
1               5                   10                  15

Gln Tyr Ser Val Arg Lys Gly His Phe Asp Thr Leu Ser Lys Gly Glu
            20                  25                  30

Leu Lys Gln Leu Leu Thr Lys Glu Leu Ala Asn Thr Ile Lys Asn Ile
        35                  40                  45

Lys Asp Lys Ala Val Ile Asp Glu Ile Phe Gln Gly Leu Asp Ala Asn
    50                  55                  60

Gln Asp Glu Gln Val Asp Phe Gln Glu Phe Ile Ser Leu Val Ala Ile
65                  70                  75                  80

Ala Leu Lys Ala Ala His Tyr His Thr His Lys Glu
                85                  90
```

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19

```
tttttttttt                                                            10
```